(12) United States Patent
Ritter et al.

(10) Patent No.: US 9,290,591 B2
(45) Date of Patent: Mar. 22, 2016

(54) IRON COMPLEXES AND METHODS FOR POLYMERIZATION

(75) Inventors: Tobias Ritter, Cambridge, MA (US); Jean B. Raynaud, Perigueux (FR); Jessica Yung Wu, Washington, DC (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/984,292

(22) PCT Filed: Feb. 8, 2012

(86) PCT No.: PCT/US2012/024315
§ 371 (c)(1),
(2), (4) Date: Sep. 25, 2013

(87) PCT Pub. No.: WO2012/109343
PCT Pub. Date: Aug. 16, 2012

(65) Prior Publication Data
US 2014/0011971 A1    Jan. 9, 2014

Related U.S. Application Data

(60) Provisional application No. 61/440,782, filed on Feb. 8, 2011.

(51) Int. Cl.
*C08F 136/08* (2006.01)
*C08F 36/08* (2006.01)
*C07F 15/02* (2006.01)
(Continued)

(52) U.S. Cl.
CPC ............ *C08F 136/08* (2013.01); *C07C 251/02* (2013.01); *C07F 15/02* (2013.01); *C07F 15/025* (2013.01); *C08F 36/08* (2013.01); *B01J 31/1815* (2013.01); *C08F 4/70* (2013.01); *C08F 4/7006* (2013.01); *C08F 4/80* (2013.01); *C08F 2410/03* (2013.01)

(58) Field of Classification Search
CPC ............ C08F 4/7006; C08F 4/70; C08F 4/80; B01J 31/1815; B01J 31/181; B01J 31/28; C07F 15/025; C07F 15/00
USPC ................ 526/172, 161, 169.1, 335; 556/138
See application file for complete search history.

(56) References Cited

U.S. PATENT DOCUMENTS 3,114,744 A * 12/1963 Lasky ............................ 526/116
3,900,456 A * 8/1975 Naylor .......................... 526/155

FOREIGN PATENT DOCUMENTS

CN          102039182 A  *  5/2011  ............... B01J 31/22
JP          10-324709          12/1998
(Continued)

OTHER PUBLICATIONS

Ricci et al. J. Mol. Catal. A: Chemical, 2003, 204-205, 287-293.*
(Continued)

*Primary Examiner* — Rip A Lee
(74) *Attorney, Agent, or Firm* — Wolf, Greenfield & Sacks, P.C.

(57) ABSTRACT

Provided are methods of preparing polymers, such as polyisoprene, polybutadiene, polypiperylene, polycyclohexadiene, poly-β-farnesene, or poly-β-myrcene, using iron complexes. Also provided are novel iron complexes, precatalysts, intermediates, and ligands useful in the inventive polymerization system.

32 Claims, 11 Drawing Sheets

(51) Int. Cl.
C07C 251/02 (2006.01)
C08F 4/80 (2006.01)
C08F 4/70 (2006.01)
B01J 31/18 (2006.01)

(56) References Cited

FOREIGN PATENT DOCUMENTS

| | | | | |
|---|---|---|---|---|
| JP | 2001-181333 A | * | 7/2001 | ............ C08F 4/645 |
| WO | WO 2004/020413 A1 | * | 3/2004 | ............ C07D 307/33 |

OTHER PUBLICATIONS

Nakayama et al. Macromolecules, 2003, 36, 7953-7958.*
Wu et al. Org. Letts., 2009, 131, 12915-12917.*
Moreau et al. Org. Letts., 2009, 11, 337-339.*
Miyasaka et al. Inorg. Chim. Acta (2005), 358(12), 3525-3535.*
Moreau, B.; Wu, J.Y.; Ritter, T. Organic Letters 2009, 11, 337-339.*
Wu, J.Y.; Stanzl, B.N.; Ritter, T. J. Am. Chem. Soc. 2010, 132, 13214-13216.*
Wu, J.Y.; Moreau, B.; Ritter, T. J. Am. Chem. Soc. 2009, 131, 12915-12917.*
International Search Report and Written Opinion for PCT/US2012/024315, mailed Sep. 21, 2012.
International Preliminary Report on Patentability for PCT/US2012/024315, mailed Aug. 22, 2013.
Bolm et al., Iron-catalyzed reactions in organic synthesis. Chem Rev. Dec. 2004;104(12):6217-54.
Britovsek et al., Iron catalyzed polyethylene chain growth on zinc: a study of the factors delineating chain transfer versus catalyzed chain growth in zinc and related metal alkyl systems. J Am Chem Soc. Sep. 1, 2004;126(34):10701-12.
Britovsek et al., Novel olefin polymerization catalysts based on iron and cobalt. Chem Comm. 1998;:849-50.
Brookhart et al., [(3,5-(CF3)2C6H3)4B]-[H(OEt2)2]+: a convenient reagent for generation and stabilization of cationic, highly electrophilic organometallic complexes. Organometallics 1992;11:3920-22.
Carballo et al., Iron(III)-promoted aza-Prins-cyclization: direct synthesis of six-membered azacycles. Org Lett. Aug. 17, 2006;8(17):3837-40.
Carril et al., Iron-catalyzed Sonogashira reactions. Angew Chem Int Ed Engl. 2008;47(26):4862-5. doi: 10.1002/anie.200801539.
Coates et al., Precise control of polyolefin stereochemistry using single-site metal catalysts. Chem Rev. Apr. 12, 2000;100(4):1223-52.
Finze et al., Trifluoromethylboranes and -borates: new synthetic strategies and applications. Angew Chem Int Ed Engl. 2007;46(48):9180-96.
Gao et al., Highly cis-1,4 selective polymerization of dienes with homogeneous Ziegler-Natta catalysts based on NCN-pincer rare earth metal dichloride precursors. J Am Chem Soc. Apr. 9, 2008;130(14):4984-91. doi:10.1021/ja711146t. Epub Mar. 14, 2008.
Gibson et al., Advances in Non-Metallocene Olefin Polymerization Catalysis. Chemical Reviews. 2002;103:283-315.
Glaser et al., Thermochemistry of the initial steps of methylaluminoxane formation. Aluminoxanes and cycloaluminoxanes by methane elimination from dimethylaluminum hydroxide and its dimeric aggregates. J Am Chem Soc. Aug. 31, 2011;133(34):13323-36.
Halasa et al., Process development of iron catalyzed 3,4 polyisoprene. Rubber World. Sep. 1, 2010. 8 pages.
Ittel et al., Late-metal catalysts for ethylene homo- and copolymerization. Chem Rev. Apr. 12, 2000;100(4):1169-203.
Li et al., β-Diketiminato Rare-Earth Metal Complexes. Structures, Catalysis, and Active Species for Highly cis-1,4-Selective Polymerization of Isoprene. Organometallics. 2010;29:2186-2193.
Moreau et al., Iron-catalyzed 1,4-addition of alpha-olefins to dienes. Org Lett. Jan. 15, 2009;11(2):337-9.
Nakayama et al., Stereospecific Polymerizations of Conjugated Dienes by Single Site Iron Complexes Having Chelating N, N, N-Donor Ligands. Macromolecules. 2003;36(21):7953-8.
Nishiura et al., Novel polymerization catalysts and hydride clusters from rare-earth metal dialkyls. Nat Chem. Apr. 2010;2(4):257-68.
Raynaud et al., Iron-catalyzed polymerization of isoprene and other 1,3-dienes. Angew Chem Int Ed Engl. Nov. 19, 2012;51(47):11805-8. doi:10.1002/anie.201205152. Epub Oct. 18, 2012.
Ricci et al. Polymerization of 1,3-dienes with iron complexes based catalysts: Influence of the ligand on catalyst activity and stereospecificity. J Mol Catal A: Chemical. 2003. 204-205:287-293.
Ricci et al., Well-defined transition metal complexes with phosphorus and nitrogen ligands for 1,3-dienes polymerization. Coord Chem Review 2010;254:661-76.
Sita et al., Ex uno plures ("out of one, many"): new paradigms for expanding the range of polyolefins through reversible group transfers. Angew Chem Int Ed Engl. 2009;48(14):2464-72.
Small et al., Highly Active Iron and Cobalt Catalysts for the Polymerization of Ethylene. J Am Chem Soc. 1998;120:4049-50.
Van Meurs et al., Polyethylene chain growth on zinc catalyzed by olefin polymerization catalysts: a comparative investigation of highly active catalyst systems across the transition series. J Am Chem Soc. Jul. 13, 2005;127(27):9913-23.
Wei et al., Aufbaureaktion redux: scalable production of precision hydrocarbons from AlR3 (R=Et or iBu) by dialkyl zinc mediated ternary living coordinative chain-transfer polymerization. Angew Chem Int Ed Engl. Mar. 1, 2010;49(10):1768-72.
Wu et al., A strategy for the synthesis of well-defined iron catalysts and application to regioselective diene hydrosilylation. J Am Chem Soc. Sep. 29, 2010;132(38):13214-6.
Wu et al., Iron-catalyzed 1,4-hydroboration of 1,3-dienes. J Am Chem Soc. Sep. 16, 2009;131(36):12915-7.
Zhang et al., Cationic alkyl rare-earth metal complexes bearing an ancillary bis(phosphinophenyl)amido ligand: a catalytic system for living cis-1,4-polymerization and copolymerization of isoprene and butadiene. Angew Chem Int Ed Engl. 2007;46(11):1909-13.
Zhang et al., Isoprene polymerization with yttrium amidinate catalysts: switching the regio- and stereoselectivity by addition of AlMe3. Angew Chem Int Ed Engl. 2008;47(14):2642-5.

* cited by examiner (i) oxidative addition
(ii) migratory insertion
(iii) π → σ rearrangement
(iv) migratory insertion
(v) π → σ rearrangement
(vi) reductive elimination and termination (i) reductive elimination and oxidative addition of initiator
(ii) migratory insertion
(iii) π → σ rearrangement
(iv) migratory insertion
(v) π → σ rearrangement
(vi) reductive elimination and termination

IRON COMPLEXES AND METHODS FOR POLYMERIZATION

RELATED APPLICATIONS

The present application is a national stage filing under 35 U.S.C. §371 of international PCT application, PCT/US2012/024315, filed Feb. 8, 2012, which claims priority under 35 U.S.C. §119(e) to U.S. provisional application, U.S. Ser. No. 61/440,782, filed Feb. 8, 2011, each of which is incorporated herein by reference.

GOVERNMENT SUPPORT

This invention was made with Government support under grant no. FA9550-10-1-0170-DOD35CAP awarded by U.S. Air Force Office of Scientific Research (AFOSR). The Government has certain rights in the invention.

BACKGROUND OF THE INVENTION

Polyisoprene is a naturally occurring unsaturated hydrocarbon polymer isolated from the latex of rubber trees, the primary source of natural rubber. Polyisoprene biosynthesis can selectively yield two geometrical isomers of polyisoprene, cis-1,4-polyisoprene (from *Hevea brasiliensis*) and trans-1,4-polyisoprene (from *Gutta percha*). Over ten million tons of the natural elastomers are harvested annually to manufacture materials such as tires and gloves. Rubber tree plantations are restricted to tropical climate, e.g. Southeast Asia and West Africa, where extensive farming supplants food crops and contaminates soils due to heavy use of arsenic-based pesticides, with severe geopolitical consequences.

About 15 million tons of synthetic rubber are produced annually. Because chemists have not yet found a satisfactory and practical way to produce rubber with appropriate control of the double bond geometry, natural rubber is still the preferred material when high quality rubber is needed, such as in airplane tires. Natural rubber does not become brittle even at low temperatures due to a high 1,4-microstructure content which allows for a low glass transition temperature (less than −65° C.). A high 1,4-microstructure content, such as pure 1,4-cis or pure trans, also allows natural rubber to undergo strain crystallization, providing an elastomeric material with enhanced mechanical properties. Generation of a polymer with a high cis-1,4 or trans-1,4 microstructure content is one way of obtaining elastomers with optimal properties. On the other hand, a reasonable 3,4-microstructure content (from 5-15%) can allow for further chemical modification of the synthetic rubber produced as an alternative to natural rubber. Moreover, the side-chain olefin can be modified post-polymerization, or serve as an anchoring group for the cationic polymerization of isobutylene, providing a potential access to novel materials with elastic properties and very low permeability to gases. See, e.g., De and White, *Rubber Technologist's Handbook*, Smithers Rapra Technology Limited: Shawbury, UK, 2011.

Industrial production of polyisoprene has mainly focused on anionic polymerization of the isoprene monomer, which controls the resulting polyisoprene double bond geometry to about a 5 to 1 (1,4-cis to 1,4-trans ratio). See, e.g., Matyjaszewski and Müller, *Controlled and Living Polymerizations: From Mechanisms to Applications*, Wiley-VCH, 2009. Catalysts based on rare earth metals such as neodymium afford ratios up to 50 to 1 (1,4-cis to 1,4-trans). See, e.g., Zhang et al., *Angew. Chem. Int. Ed.* (2007) 46:1909-1913; Zhang et al., Hou, *Angew. Chem. Int. Ed.* (2008) 47:2642-2645; Gao and Cui, *J. Am. Chem. Soc.* (2008) 130, 4984-4991; Ricci et al., *Coord. Chem. Rev.* (2010) 254:661-676; Nishiura and Hou, *Nat. Chem.* (2010) 2:257-268; and Li et al., *Organometallics* (2010) 29:2186. However, rare Earth metals are expensive and are only obtained by mining. Therefore, there is a need for a better, less expensive, way of making polymers from 1,3-dienes, such as polyisoprene, with a high selectivity, e.g., a selectivity for either 1,4-cis double bonds, 1,4-trans double bonds, 3,4-selectivity, or 1,2-selectivity, with less of an impact on the environment.

SUMMARY OF THE INVENTION

The present invention is based on the finding that polymers, e.g., homopolymers, co-polymers, etc., may be efficiently and selectively prepared from one or more alkenes in the presence of iron complexes, e.g., as described herein. Provided herein are methods of preparing a polymer from one or more alkene monomers in the presence of an iron complex, optionally with a high selectivity. Also provided are novel iron complexes, ligands, compositions, kits, and systems useful in the polymerization reactions.

In certain embodiments, the alkene useful in the polymerization reaction is a diene. In certain embodiments, the diene is a 1,3-diene. In certain embodiments, the diene is an optionally substituted 1,3-diene of formula (i):

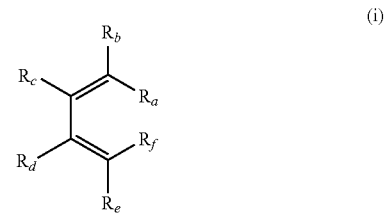

(i)

wherein each instance of $R_a$, $R_b$, $R_c$, $R_d$, $R_e$, and $R_f$ are independently selected from the group consisting of hydrogen, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R_a$ and $R_f$ are joined to form an optionally substituted heterocycyl or carbocyclyl ring.

In certain embodiments, the polymer provided from the polymerization of the optionally substituted 1,3-diene is provided with a high selectivity, e.g., 1,4-cis, 1,4-trans-, 3,4-, or 1,2-selectivity.

In certain embodiments, the diene is selected from the group consisting of isoprene, 1,3-pentadiene (piperylene), 1,3-butadiene, cyclohexa-1,3-diene, trans-β-farnesene, and β-myrcene.

In one aspect, provided is a method of preparing polybutadiene comprising polymerizing 1,3-butadiene in the presence of an iron complex to provide poly 1,3-butadiene.

In another aspect, provided is a method of preparing polyperylene comprising polymerizing 1,3-pentadiene (piperylene) in the presence of an iron complex.

In another aspect, provided are methods of preparing polycyclohexadiene comprising polymerizing cyclohexa-1,3-diene in the presence of an iron complex.

In another aspect, provided are methods of preparing poly-β-farnesene comprising polymerizing trans-β-farnesene in the presence of an iron complex.

In another aspect, provided are methods of preparing poly-β-myrcene comprising polymerizing β-myrcene in the presence of an iron complex.

In yet another aspect, provided are methods of preparing polyisoprene comprising polymerizing isoprene in the presence of an iron complex.

In certain embodiments, the polyisoprene is at least 50% 1,4-polyisoprene. In certain embodiments, the 1,4-polyisoprene preferably formed is 1,4-cis-polyisoprene. For example, in certain embodiments, the polyisoprene is at least 50% 1,4-cis-polyisoprene. In certain embodiments, the polyisoprene is between about 50% to about 100% 1,4-cis-polyisoprene. In certain embodiments, the polyisoprene is less than 5% 1,4-trans-polyisoprene. In certain embodiments, the polyisoprene is between about 0.5% to about 5% 1,4-trans-polyisoprene. In certain embodiments, the polyisoprene comprises 1,4-cis-polyisoprene and 1,4-trans-polyisoprene in a ratio of between about 95:5 to about 100:0 1,4-cis-polyisoprene to 1,4-trans-polyisoprene. Alternatively, in certain embodiments, the 1,4-polyisoprene preferably formed is 1,4-trans-polyisoprene. For example, in certain embodiments, the polyisoprene is at least 50% 1,4-trans-polyisoprene. In certain embodiments, the polyisoprene is between about 50% to about 100% 1,4-trans-polyisoprene. In certain embodiments, the polyisoprene is less than 5% 1,4-cis-polyisoprene. In certain embodiments, the polyisoprene is between about 0.5% to about 5% 1,4-cis-polyisoprene. In certain embodiments, the polyisoprene comprises 1,4-trans-polyisoprene and 1,4-cis-polyisoprene in a ratio of between about 95:5 to about 100:0 1,4-trans-polyisoprene to 1,4-cis-polyisoprene. In certain embodiments, the polyisoprene is less than 35% 3,4-polyisoprene. In certain embodiments, the polyisoprene is less than 5% 1,2-polyisoprene.

In certain embodiments, the step of polymerizing further comprises an initiator. In certain embodiments, the step of polymerizing comprises mixing the initiator and complex prior to adding the isoprene. In certain embodiments, the step of polymerizing comprises mixing the isoprene and the complex prior to adding the initiator.

In certain embodiments, the initiator is a compound of the formula A-Z, wherein one of A and Z is independently silyl and boronyl, and one of A and Z is independently selected from group consisting of boronyl, halogen, and silyl. In certain embodiments, the initiator is selected from the group consisting of dimethyl(phenyl)(4,4,5,5-tetramethyl-1,3,2-dioxaborolan-2-yl)silane, hexaphenyldisilane, hexamethyldisilane, 1,1,2,2-tetramethyl-1,2-diphenyldisilane, chlorotrimethylsilane, silaboranes, and diboranes.

In certain embodiments, the reaction comprises an alkylating agent, e.g., to activate the iron (II) complex, and a dealkylating agent, e.g., in order to allow polymerization. Exemplary alkylating agents include, but are not limited to, trialkylaluminum reagents (e.g., $AlR_3$, wherein R is optionally substituted alkyl, e.g., tri-isobutylaluminum, tri-ethylaluminum), dialkylzinc reagents, dialkylmagnesium reagents, calcium reagents, and Grignard reagents. Exemplary dealkylating reagents include, aluminates and borates, e.g., borates such as triphenylmethyl(trityl)tetrakispentafluoroborate ($BArF_{20}$). $BArF_{20}$ comprises a carbocation able to abstract the alkyl group from the complex in order to form an active cationic complex and a non-coordinating anion.

In certain embodiments, the reaction comprises methylaluminoxane (MAO). Methylaluminoxane (MAO) serves both the role of alkylating reagent and dealkylating reagent in order to activate the iron(II) chloride complex and allow polymerization.

In certain embodiments, the step of polymerizing further comprises an organic solvent. In certain embodiments, the organic solvent comprises an ether, a polar aprotic solvent, an aromatic solvent, a chlorinated hydrocarbon solvent, a hydrocarbon solvent, or a mixture thereof. In certain embodiments, the organic solvent comprises an aromatic solvent, a hydrocarbon solvent, or a mixture thereof.

In certain embodiments, the step of polymerizing is conducted at a temperature of between about −80° C. to about 100° C. In certain embodiments, the step of polymerizing is conducted at a temperature of between about −80° C. to about 30° C. In certain embodiments, the step of polymerizing is conducted at a temperature of about −78° C. In certain embodiments, the step of polymerizing is conducted at a temperature of about 25° C.

In certain embodiments, the number-average molar mass ($M_n$) of the polyisoprene is between about 2,000 g/mol to about 5,000,000 g/mol.

In certain embodiments, the dispersity of the polyisoprene is between about 1 to about 20.

In certain embodiments, the iron of the metal complex has a valency of (0). In certain embodiments, the iron of the metal complex has a valency of (II).

A complex useful in any of the inventive methods and processes, as described herein, is a complex comprising iron and a ligand of the Formula (A):

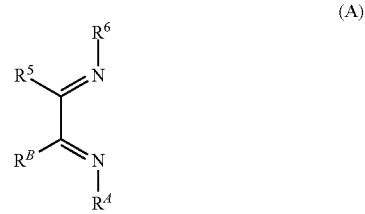

(A)

wherein:

$R^5$ selected from the group consisting of hydrogen, halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, phosphino, boronyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;

$R^6$ is selected from the group consisting of substituted hydroxyl, substituted thiol, monosubstituted amino, disubstituted amino, trisubstituted amino, sulfonyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^5$ and $R^6$ are joined to form a ring selected from optionally substituted heterocyclyl or optionally substituted heteroaryl;

$R^A$ is selected from optionally substituted alkyl, optionally substituted alkenyl, optionally substituted alkynyl, optionally substituted carbocyclyl, optionally substituted heterocyclyl, optionally substituted aryl, and optionally substituted heteroaryl; and $R^B$ is selected from hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^A$ and $R^B$ are joined to form a ring selected from optionally substituted heterocyclyl and optionally substituted heteroaryl; or $R^B$ and $R^5$ are joined to form a ring selected from an optionally substituted carbocyclyl, optionally substituted heterocyclyl, optionally substituted aryl, or optionally substituted heteroaryl ring; or $R^B$ is joined to both $R^A$ and $R^5$ in order to form a fused heterocyclic or heteroaryl ring system.

In certain embodiments, the iron complex useful any of the inventive methods and processes is of the Formula (A-II):

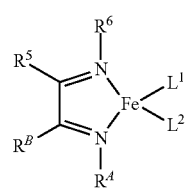

(A-II)

wherein $R^A$, $R^B$, $R^5$, and $R^6$ are as defined herein; and $L^1$ and $L^2$ are monodentate ligands independently selected from the group consisting of hydrogen, $H_2O$, —$NH_3$, —SCN, —$N_3$, —$N_2$, —$ONO_3$, —$NO_2$, —ONO, —$NCCH_3$, —NC, —CN, —CO, halogen, amino, monosubstituted amino, disubstituted amino, trisubstituted amino, hydroxyl, substituted hydroxyl, thiol, substituted thiol, phosphino, phosphono, phosphoramido, silyl, boronyl, stannyl, germyl, arsenyl, carbonyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $L^1$ and $L^2$ are a bidentate ligand independently selected from —$NH_2$, monosubstituted amino, disubstituted amino, phosphino, silyl, boronyl, —OH, —O—, —CN, optionally substituted alkyl, optionally substituted alkenyl, optionally substituted alkynyl, optionally substituted carbocyclyl, optionally substituted heterocyclyl, optionally substituted aryl, and optionally substituted heteroaryl, wherein $L^1$ and $L^2$ are joined by one or more bonds or divalent groups selected from divalent alkyl, divalent alkenyl, divalent alkynyl, divalent carbocyclyl, divalent heterocyclyl, divalent aryl, and divalent heteroaryl.

FIGS. 1 and 2 depict the proposed mechanism of the iron catalyzed polymerization of isoprene following General Methods I or II of the Examples. FIG. 3 depicts the proposed mechanism of the iron catalyzed polymerization of isoprene following General Method III of the Examples. Various ligands useful in the inventive method are described herein. Certain ligands have been found to preferentially generate trans-1,4-polyisoprene, e.g., such as ligand (L-97) following methods described herein, e.g., see General Method III. Other ligands have been found to preferentially generate cis-1,4-polyisoprene, e.g., such as ligand (L-29) following methods described herein, e.g., see General Method I or II, or ligand (L-70) following methods described herein, e.g., see General Method III.

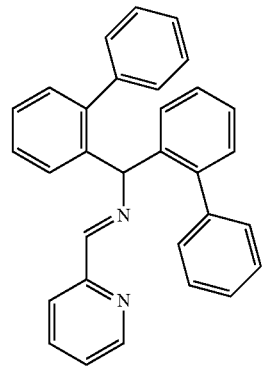

(L-29)

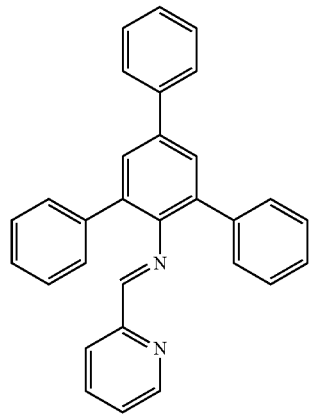

(L-70)

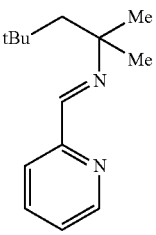

(L-97)

In yet another aspect, the present invention is directed to intermediates formed in the catalytic cycle.

The details of one or more embodiments of the invention are set forth in the accompanying Detailed Description, Examples, Claims, and Figures. Other features, objects, and advantages of the invention will be apparent from the description and from the claims.

BRIEF DESCRIPTION OF THE DRAWINGS

FIG. 5A depicts the SEC trace of polyisoprene (PI) obtained following the procedure of Example 1 (detected at 212 nm, using THF as eluent, and polystyrene (PS) standards for calibration). A correction factor was applied to account for the difference in hydrodynamic volumes between identical molar mass of PS and PI.

FIG. 5B depicts the SEC trace of trans-1,4-polyisoprene $M_w$=125,000 g/mol, Đ=2.0 following the procedure of Example 4.

FIG. 5C depicts the SEC trace of cis-1,4-polyisoprene $M_w$=140,000 g/mol, Đ=1.7 following the procedure of Example 8.

FIG. 5D depicts the SEC-$M_n$ trace (curve b) of chain extension of a pre-existing polyisoprene polymer of lower molar masses (curve a) following the procedure of Example 4. Similarly, the SEC-$M_n$ trace (curve d) represents the chain extension to higher molar masses of a pre-existing polyisoprene polymer of medium molar masses (curve c) following the procedure of Example 7.

FIG. 5E depicts the accessible molar masses obtained from the various polymerization reactions reported above varying the ratio [monomer]/[Fe]. Curves (e) and (f) were obtained with a [isoprene] to [Fe] ratio of 5000. Curve (c) was obtained with a [isoprene] to [Fe] ratio of 2000. Curve (a) was obtained with a [isoprene] to [Fe] ratio of 1000. Curve (d) represents an aliquot of Example 4 after 1 hour of polymerization. Curve (b) represents an aliquot of Example 11 after 1 hour of polymerization.

DEFINITIONS

Figure 1:
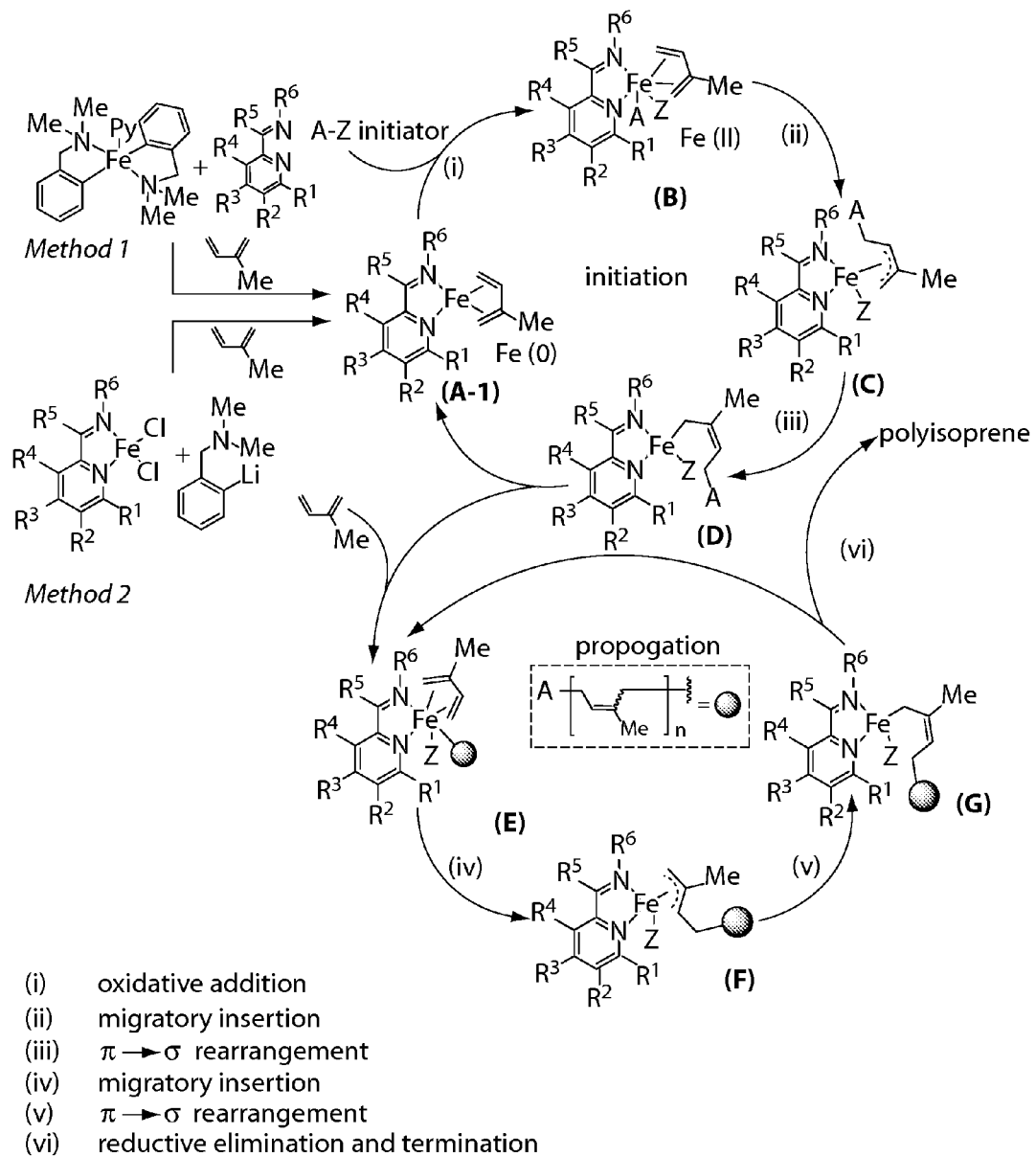
FIGS. 1 to 3 depict proposed mechanisms of the iron-catalyzed polymerization of isoprene following the methods described in the Examples.

Definitions of specific functional groups and chemical terms are described in more detail below. The chemical elements are identified in accordance with the Periodic Table of the Elements, CAS version, Handbook of Chemistry and Physics, 75$^{th}$. Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; and S. K. De and J. R. White, *Rubber Technologist's Handbook*, Rapra Technology Limited, Shawbury, Shrewsbury, Shropshire, SY4 4NR, UK, 2001, each of which is incorporated herein by reference.

Ligands and complexes described herein can comprise one or more asymmetric centers, and thus can exist in various isomeric forms, e.g., enantiomers and/or diastereomers. For example, the ligands and/or complexes described herein can be in the form of an individual enantiomer, diastereomer or geometric isomer, or can be in the form of a mixture of stereoisomers, including racemic mixtures and mixtures enriched in one or more stereoisome. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses ligands and complexes as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —CH$_3$). In certain embodiments, the alkyl group is a substituted $C_{1-10}$ alkyl.

"Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —CF$_3$, —CF$_2$CF$_3$, —CF$_2$CF$_2$CF$_3$, —CCl$_3$, —CFCl$_2$, —CF$_2$Cl, and the like.

As used herein, "alkenyl" refers to a radical of a straight-chain or branched hydrocarbon group having from 2 to 20 carbon atoms and one or more carbon-carbon double bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "alkynyl" refers to a radical of a straight-chain or branched hydrocarbon group having from 2 to 20 carbon atoms and one or more carbon-carbon triple bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "carbocyclyl" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted. (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic or tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, a "bond" refers to a single bond, a double bond or a triple bond. As used herein a "direct bond" or "covalent bond" refers to a single bond joining two groups.

Alkyl, alkenyl, alkynyl, carbocyclyl, heterocyclyl, aryl and heteroaryl, referred to without the prefix "divalent," describe a monoradical of alkyl, alkenyl, alkynyl, carbocyclyl, heterocyclyl, aryl, or heteroaryl, respectively, and as defined herein, wherein the monoradical is attached to another group by only one single bond.

"Divalent" used as a prefix, such as divalent alkyl, divalent alkenyl, divalent alkynyl, divalent carbocyclyl, divalent heterocyclyl, divalent aryl and divalent heteroaryl groups, describe a diradical of alkyl, alkenyl, alkynyl, carbocyclyl, heterocyclyl, aryl, or heteroaryl, respectively, and as defined herein, wherein the diradical is attached to one or two groups by two single bonds.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O) (NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —P(R$^{cc}$)$_3$, —OP(R$^{cc}$)$_2$, —OP(R$^{cc}$)$_3$, —B($R^{aa}$)$_2$, —B(O$R^{cc}$)$_2$, —B$R^{aa}$(O$R^{cc}$), $C_{1-10}$ alkyl, $C_{1-10}$ perhaloalkyl, $C_{2-10}$ alkenyl, $C_{2-10}$ alkynyl, $C_{3-14}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3^+X^-$, —N(O$R^{ee}$)$R^{ff}$, —N=C=$R^{ee}$, —SH, —S$R^{ee}$, —SS$R^{ee}$, —C(=O)$R^{ee}$, —CO$_2$H, —CO$_2R^{ee}$, —OC(=O)$R^{ee}$, —OCO$_2R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2R^{ee}$, —SO$_2$N($R^{ff}$)$_2$, —SO$_2R^{ee}$, —SO$_2$O$R^{ee}$, —OSO$_2R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)$_2R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+X^-$, —NH(C$_{1-6}$ alkyl)$_2^+X^-$, —NH$_2$(C$_{1-6}$ alkyl)$^+X^-$, —NH$_3^+X^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S;

wherein $X^-$ is a counterion.

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —O$R^{aa}$, —ON($R^{bb}$)$_2$, —OC(=O)S$R^{aa}$, —OC(=O)$R^{aa}$, —OCO$_2R^{aa}$, —OC(=O)N($R^{bb}$)$_2$, —OC(=NR$^{bb}$)$R^{aa}$, —OC(=N$R^{bb}$)O$R^{aa}$, —OC(=N$R^{bb}$)N($R^{bb}$)$_2$, —OS(=O)$R^{aa}$, —OSO$_2R^{aa}$, —OSi($R^{aa}$)$_3$, —OP($R^{cc}$)$_2$, —OP($R^{cc}$)$_3$, —OP(=O)$_2R^{aa}$, —OP(=O)($R^{aa}$)$_2$, —OP(=O)(O$R^{cc}$)$_2$, —OP(=O)$_2$N($R^{bb}$)$_2$, and —OP(=O)(N$R^{bb}$)$_2$, wherein $R^{aa}$, $R^{bb}$, and $R^{cc}$ are as defined herein. In the case wherein "substituted hydroxyl" is a ligand $L_1$ or $L_2$, "substituted hydroxyl" also refers to the group ($R^{aa}$)$_2$O, wherein $R^{aa}$ is as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —S$R^{aa}$, —S=S$R^{cc}$, —SC(=S)S$R^{aa}$, —SC(=O)S$R^{aa}$, —SC(=O)O$R^{aa}$, and —SC(=O)$R^{aa}$, wherein $R^{aa}$ and $R^{cc}$ are as defined herein.

As used herein, the term, "amino" refers to the group —NH$_2$.

As used herein, the term "monosubstituted amino" refers to an amino group wherein the nitrogen atom directly attached to the parent molecule, or coordinated to an iron atom, is substituted with one hydrogen and one group other than hydrogen, and includes groups selected from —NH($R^{bb}$), —NHC(=O)$R^{aa}$, —NHCO$_2R^{aa}$, —NHC(=O)N($R^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule, or coordinated to an iron atom, is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule, or coordinated to an iron atom, is substituted with three groups, and includes groups selected from —N(R$^{bb}$)$_3$ and —N(R$^{bb}$)$_3$$^+$X$^-$, wherein R$^{bb}$ and X$^-$ are as defined herein.

As used herein, the term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

As used herein, the term "sulfinyl" refers to the group —S(=O)R$^{aa}$, wherein R$^{aa}$ is as defined herein.

As used herein, the term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$—C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$, and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

As used herein, the term "silyl" refers to the group —Si(R$^{aa}$)$_3$, wherein R$^{aa}$ is as defined herein.

As used herein, the term "boronyl" refers to boranes, boronic acids, boronic esters, borinic acids, and borinic esters, e.g., boronyl groups of the formula —B(R$^{aa}$)$_2$, —B(OR$^{cc}$)$_2$, and —BR$^{aa}$(OR$^{cc}$), wherein R$^{aa}$ and R$^{cc}$ are as defined herein.

As used herein, the term "phosphino" refers to the group —P(R$^{cc}$)$_3$, wherein R$^{cc}$ is as defined herein. An exemplary phosphino group is triphenylphosphine.

As used herein, the term "phosphono" refers to the group —O(P=O)(OR$^{cc}$)R$^{aa}$, wherein R$^{aa}$ and R$^{cc}$ are as defined herein.

As used herein, the term "phosphoramido" refers to the group —O(P=O)(NR$^{bb}$)$_2$, wherein each R$^{bb}$ is as defined herein.

As used herein, the term "stannyl" refers to the group —Sn(R$^{cc}$)$_3$, wherein R$^{cc}$ is as defined herein.

As used herein, the term "germyl" refers to the group —Ge(R$^{cc}$)$_3$, wherein R$^{cc}$ is as defined herein.

As used herein, the term "arsenyl" refers to the group —As(R$^{cc}$)$_3$, wherein R$^{cc}$ is as defined herein.

As used herein, the term "halo" or "halogen" refers to fluorine (fluoro, —F) chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an amino protecting group. Amino protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, amino protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Amino protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)carbonyl derivative, N'-p-toluenesulfonylaminocarbonyl derivative, N'-phenylaminothiocarbonyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

These and other exemplary substituents are described in more detail in the Detailed Description, Examples, Claims, and Figures. The invention is not intended to be limited in any manner by the above exemplary listing of substituents.

As used herein, when the reaction "selectively" or "preferentially" generates a polymer, or a polymer "predominately comprises" a particular unit, it is meant to indicate that the polymer comprises at least 50% of a particular unit, e.g., cis-1,4, trans-1,4, 1,2, or 3,4-units, along the polymer backbone. As used herein, the percentage of a particular geometry of the polymerized residues refers to the relative amount (w/w) of that geometry provided in the polymer (e.g., as determined by NMR).

As used herein, "polyisoprene" refers to a polymer of isoprene (i.e., 2-methyl-1,3-butadiene). In certain embodiments, the microstructure of the polyisoprene comprises a mixture of one or more polymerized isoprene residues (isoprene units) along the backbone of the polyisoprene chain selected from 1,4-polyisoprene, 3,4-polyisoprene, and 1,2-polyisoprene units. As used herein, the percentage of a particular geometry of the polymerized isoprene residues (units) refers to the relative amount (w/w) of that geometry provided in the polyisoprene (e.g., as determined by NMR). As used herein, "1,4-polyisoprene" refers to 1,4-cis-polyisoprene, 1,4-trans-polyisoprene, or a mixture thereof. In certain embodiments, the polyisoprene comprises a mixture of one or more polymerized isoprene residues (units) along the backbone of the polyisoprene chain selected from 1,4-cis-polyisoprene, 1,4-trans-polyisoprene, 3,4-polyisoprene and 1,2-polyisoprene. Likewise, the percentage of a particular geometry of any polymer as describe herein refers to the relative amount (w/w) of that geometry of polymerized residues (units) along the backbone of the polymer chain, e.g., selected from any one of "1,4", "1,2", or "3,4", or a mixture thereof.

"Molar mass averages": Different average values (e.g., $M_n$, $M_w$, $M_v$ and $M_z$) can be defined depending upon the statistical method that is applied. The weighted mean can be taken with the weight fraction, the mole fraction or the volume fraction (see, e.g., R. J. Young and P. A. Lovell, *Introduction to Polymers*, 1991, incorporated herein by reference).

| Dispersity (D) | $M_w/M_n$ |
| --- | --- |
| Number average molar mass ($M_n$) | $M_n = \dfrac{\Sigma M_i N_i}{\Sigma N_i}$ |
| Weight average molar mass ($M_w$) | $M_w = \dfrac{\Sigma M_i^2 N_i}{\Sigma M_i N_i}$ |
| Z average molar mass ($M_z$) | $M_z = \dfrac{\Sigma M_i^3 N_i}{\Sigma M_i^2 N_i}$ |
| Viscosity average molar mass ($M_v$) | $M_v = \left[\dfrac{\Sigma M_i^{1+a} N_i}{\Sigma M_i N_i}\right]^{1/a}$ |
| | wherein "a" is the exponent in the Mark-Houwink equation |

In linear polymers, the individual polymer chains rarely have exactly the same degree of polymerization and molar mass, and there is always a distribution around an average value. The molar mass distribution (or molecular weight distribution) in a polymer describes the relationship between the number of moles of each polymer species ($N_i$) and the molar mass ($M_i$) of that species.

"Size exclusion chromatography": The most common technique for measuring molecular weight is a variant of high pressure liquid chromatography (HPLC), known by the interchangeable terms of size exclusion chromatography (SEC) and gel permeation chromatography (GPC). These techniques involve forcing the polymer solution through a maxtrix of cross-linked polymer particles at a pressure of up to several thousand psi. The most common detectors used for SEC is a differential refractive index detector which measures the change in refractive index of the solvent.

"Dispersity": Dispersity (D) is a measure of the distribution of molecular mass in a given polymer sample and is calculated by dividing the weight average molar mass ($M_w$) by the number average molar mass ($M_n$). The dispersity of a given sample can have a value equal to or greater than 1. As the polymer chains approach uniform chain length, the dispersity approaches unity (1). The dispersity of a polymer can be modified, for example, using polymer fractionation (e.g., preparative SEC, Baker-Williams fractionation, continuous spin fractionation), or modifying the work-up procedure (e.g., by partially dissolving a polymer, an insoluble high molar mass fraction may be filtered off resulting in a large reduction in $M_w$ and a small reduction in $M_n$, thus reducing polydispersity).

DETAILED DESCRIPTION OF CERTAIN EMBODIMENTS OF THE INVENTION

Iron complexes have been shown to effect a variety of regioselective and stereoselective addition reactions with 1,3-dienes as substrates. See, e.g., Moreau et al., *Org. Lett.* (2009) 11:337-339; Wu et al., *J. Am. Chem. Soc.* (2009) 131:12915-12917; and Wu et al., *J. Am. Chem. Soc.* (2010) 132:13214-13216. It has now been discovered that such iron complexes are capable of catalyzing the polymerization of a variety of alkenes, such as isoprene, in a selective manner. For example, it has been discovered that polymerization of isoprene in the presence of an iron complex selectively provides a 1,4-polyisoprene polymer. Depending upon the reaction conditions, e.g., such as temperature, reagents, and ligand used, it has been discovered that the reaction can selectively provide either 1,4-cis-polyisoprene or 1,4-trans-polyisoprene. Other alkenes, such as 1,3-pentadiene (piperylene), 1,3-butadiene, cyclohexa-1,3-diene, trans-β-farnesene, and β-myrcene, behave similarly under similar polymerization conditions and afford the corresponding polymers. Thus, provided herein are methods of preparing a polymer comprising polymerizing an alkene in the presence of an iron complex. Also provided are novel iron complexes, ligands, compositions, kits, and systems useful in this polymerization reaction.

Polymers

In certain embodiments, the alkene is a diene. In certain embodiments, the diene is a 1,3-diene. In certain embodiments, the diene is an optionally substituted 1,3-diene of Formula (i), as provided below, and the polymerization of the 1,3-diene of Formula (i) results in a polymer comprising one or more cis-1,4, trans-1,4, 1,2-, and/or 3,4-units:

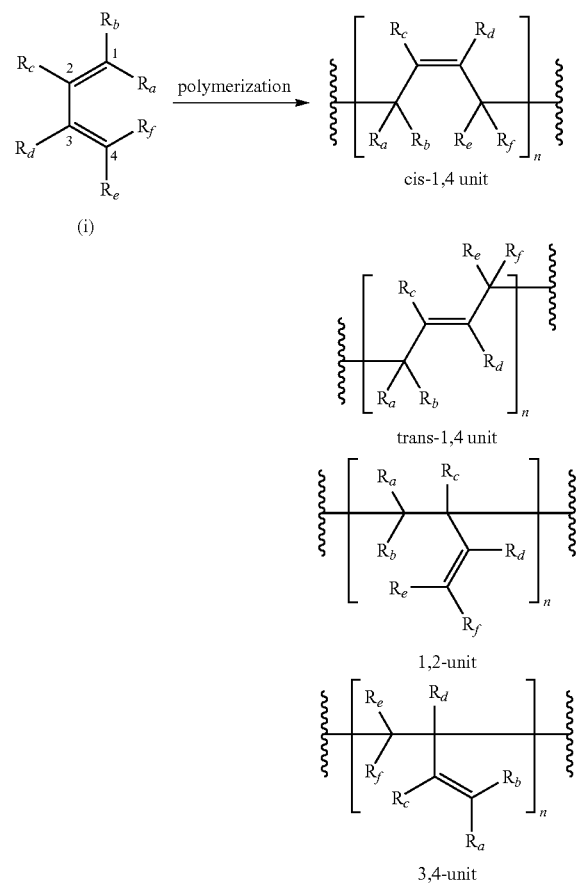

Scheme 1.

wherein:
each instance of $R_a$, $R_b$, $R_c$, $R_d$, $R_e$, and $R_f$ are independently selected from the group consisting of hydrogen, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R_a$ and $R_f$ are joined to form an optionally substituted heterocycyl or carbocyclyl ring; and
n is an integer of between 1 and 100,000, inclusive.

Polymerization of a 1,3-diene of Formula (i) generates a polymer comprising one or more 1,4-cis, 1,4-trans-, 3,4-, or 1,2-units present along the polymer backbone, as depicted in Scheme 1, e.g., 1 to 100,000, 1 to 50,000, 1 to 25,000, 1 to 10,000, 1 to 5,000, 1 to 2,000, 1 to 1,000, 1 to 500, 1 to 400, 1 to 300, 1 to 200, 1 to 100, 1 to 50, 1 to 25, 1 to 10, 1 to 5, 1 to 3, or 1 to 2, of 1,4-cis, 1,4-trans-, 3,4-, or 1,2-units along the polymer backbone. In certain embodiments, the polymer is provided with a high selectivity, e.g., 1,4-cis, 1,4-trans-, 3,4-, or 1,2-selectivity.

In certain embodiments, each instance of $R_a$, $R_b$, $R_c$, $R_d$, $R_e$, and $R_f$ are independently selected from the group consisting of hydrogen, silyl, optionally substituted alkyl, optionally substituted alkenyl, optionally substituted carbocyclyl, optionally substituted heterocyclyl, optionally substituted aryl, and optionally substituted heteroaryl; or $R_a$ and $R_f$ are joined to form an optionally substituted heterocycyl or carbocyclyl ring. In certain embodiments, each instance of $R_a$, $R_b$, $R_c$, $R_d$, $R_e$, and $R_f$ are independently selected from the group consisting of hydrogen, optionally substituted alkyl, and optionally substituted alkenyl, or $R_a$ and $R_f$ are joined to form an optionally substituted carbocyclyl ring.

In certain embodiments, $R_a$ is hydrogen. In certain embodiments, $R_b$ is hydrogen. In certain embodiments, $R_c$ is hydrogen. In certain embodiments, $R_d$ is hydrogen. In certain embodiments, $R_e$ is hydrogen. In certain embodiments, $R_f$ is hydrogen.

In certain embodiments, $R_a$ and $R_f$ are hydrogen. In certain embodiments, $R_a$ and $R_b$ are hydrogen. In certain embodiments, $R_a$ and $R_c$ are hydrogen. In certain embodiments, $R_a$ and $R_d$ are hydrogen. In certain embodiments, $R_a$ and $R_e$ are hydrogen. In certain embodiments, $R_b$ and $R_c$ are hydrogen. In certain embodiments, $R_b$ and $R_d$ are hydrogen. In certain embodiments, $R_b$ and $R_e$ are hydrogen. In certain embodiments, $R_b$ and $R_f$ are hydrogen. In certain embodiments, $R_c$ and $R_d$ are hydrogen. In certain embodiments, $R_c$ and $R_e$ are hydrogen. In certain embodiments, $R_c$ and $R_f$ are hydrogen. In certain embodiments, $R_d$ and $R_e$ are hydrogen. In certain embodiments, $R_d$ and $R_f$ are hydrogen. In certain embodiments, $R_e$ and $R_f$ are hydrogen.

In certain embodiments, $R_a$, $R_b$, $R_e$ and $R_f$ are hydrogen. In certain embodiments, each instance of $R_a$, $R_b$, $R_c$, $R_d$, $R_e$, and $R_f$ are hydrogen. Polymerization of a 1,3-diene of Formula (i), wherein each instance of $R_a$, $R_b$, $R_c$, $R_d$, $R_e$, and $R_f$ are hydrogen, i.e., 1,3-butadiene, generates polybutadiene comprising one or more 1,4-cis, 1,4-trans-, or 1,2-units present along the polymer backbone, as depicted in Scheme 2. Thus, in one aspect, provided is a method of preparing polybutadiene comprising polymerizing 1,3-butadiene in the presence of an iron complex, optionally wherein the polybutadiene, so generated, is provided with a high selectivity, e.g., 1,4-cis, 1,4-trans-, or 1,2-selectivity.

Scheme 2.

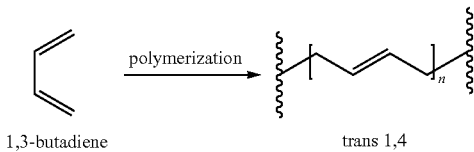

1,3-butadiene     trans 1,4

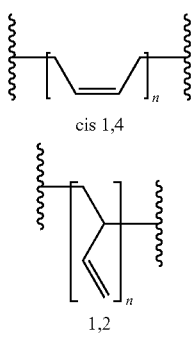

cis 1,4

1,2

In certain embodiments, $R_a$, $R_b$, $R_c$, $R_d$, and $R_e$ are hydrogen. In certain embodiments, $R_a$, $R_b$, $R_c$, $R_d$, and $R_e$ are hydrogen, and $R_f$ is optionally substituted alkyl (e.g., optionally substituted $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, or $C_{10}$alkyl). In certain embodiments, $R_f$ is optionally substituted $C_1$alkyl, e.g., methyl. In certain embodiments, the diene is 1,3-pentadiene. Polymerization of a 1,3-diene of Formula (i), wherein each instance of $R_a$, $R_b$, $R_c$, $R_d$, and $R_e$ are hydrogen and $R_f$ is methyl, i.e., 1,3-pentadiene, generates polypiperylene comprising one or more 1,4-cis, 1,4-trans-, 3,4- or 1,2-units present along the polymer backbone, as depicted in Scheme 3. Thus, in another aspect, provided is a method of preparing polypiperylene comprising polymerizing 1,3-pentadiene in the presence of an iron complex, optionally wherein the polypiperylene, so generated, is provided with a high selectivity, e.g., 1,4-cis, 1,4-trans-, 3,4-, or 1,2-selectivity.

Scheme 3.

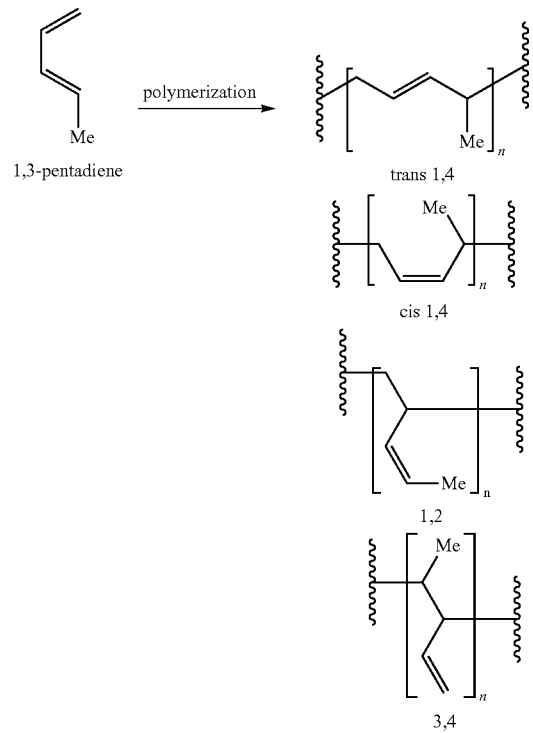

In certain embodiments, $R_c$ is hydrogen, and $R_d$ is optionally substituted alkenyl (e.g., optionally substituted $C_2$alkenyl, $C_3$alkenyl, $C_4$alkenyl, $C_5$alkenyl, $C_6$alkenyl, $C_7$alkenyl, $C_8$alkenyl, $C_9$alkenyl, or $C_{10}$alkenyl). In certain embodiments, $R_a$, $R_b$, $R_c$, $R_e$ and $R_f$ are hydrogen and $R_d$ is optionally substituted alkenyl.

In certain embodiments, $R_a$, $R_b$, $R_c$, $R_e$ and $R_f$ are hydrogen and $R_d$ is optionally substituted $C_5$alkenyl. Polymerization of a 1,3-diene of Formula (i), wherein each instance of $R_a$, $R_b$, $R_c$, $R_e$ and $R_f$ are hydrogen and $R_d$ is optionally substituted $C_5$alkenyl, e.g., β-myrcene, generates poly-β-myrcene comprising one or more 1,4-cis, 1,4-trans-, 3,4-, or 1,2-units present along the polymer backbone, as depicted in Scheme 4. Thus, in another aspect, provided is a method of preparing poly-β-myrcene comprising polymerizing β-myrcene in the presence of an iron complex, optionally wherein the poly-β-myrcene, so generated, is provided with a high selectivity, e.g., 1,4-cis, 1,4-trans-, 3,4-, or 1,2-selectivity.

trans-β-farnesene. In certain embodiments, $R_a$, $R_b$, $R_c$, $R_e$ and $R_f$ are hydrogen and $R_d$ is optionally substituted $C_9$alkenyl. Polymerization of a 1,3-diene of Formula (i), wherein each instance of $R_a$, $R_b$, $R_c$, $R_e$ and $R_f$ are hydrogen and $R_d$ is optionally substituted $C_9$ alkenyl, e.g., trans-β-farnesene, generates poly-β-farnesene comprising one or more 1,4-cis, 1,4-trans-, 3,4-, or 1,2-units present along the polymer backbone, as depicted in Scheme 5. Thus, in another aspect, provided is a method of preparing poly-β-farnesene comprising polymerizing trans-β-farnesene in the presence of an iron complex, optionally wherein the poly-β-farnesene, so generated, is provided with a high selectivity, e.g., 1,4-cis, 1,4-trans-, 3,4-, or 1,2-selectivity.

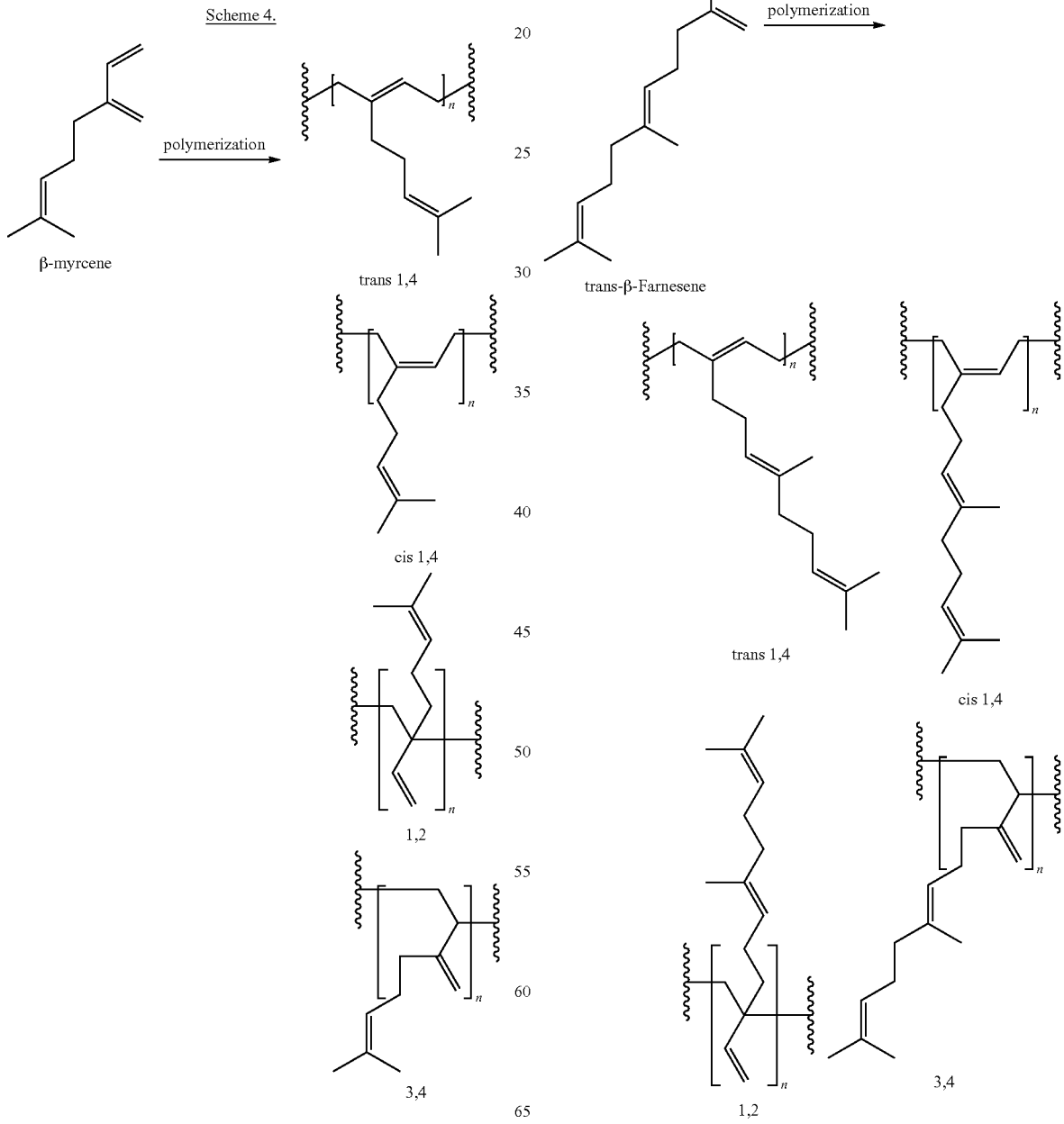

In certain embodiments, $R_a$, $R_b$, $R_c$, $R_e$ and $R_f$ are hydrogen and $R_d$ is optionally substituted $C_9$alkenyl, e.g., the diene is In certain embodiments, $R_c$ is hydrogen, and $R_d$ is optionally substituted alkyl (e.g., optionally substituted $C_1$alkyl, $C_2$alkyl, $C_3$alkyl, $C_4$alkyl, $C_5$alkyl, $C_6$alkyl, $C_7$alkyl, $C_8$alkyl, $C_9$alkyl, or $C_{10}$alkyl). In certain embodiments, $R_c$ is hydrogen, and $R_d$ is optionally substituted $C_1$alkyl, e.g., methyl. In certain embodiments, $R_a$, $R_b$, $R_c$, $R_e$, and $R_f$ are hydrogen, and $R_d$ is optionally substituted $C_1$alkyl. Polymerization of a 1,3-diene of Formula (i), wherein each instance of $R_a$, $R_b$, $R_c$, $R_e$, and $R_f$ are hydrogen and $R_d$ is methyl, i.e., isoprene, generates polyisoprene comprising one or more 1,4-cis, 1,4-trans-, 3,4-, or 1,2-units present along the polymer backbone, as depicted in Scheme 6. Thus, in another aspect, provided is a method of preparing polyisoprene comprising polymerizing isoprene in the presence of an iron complex, optionally wherein the polyisoprene, so generated, is provided with a high selectivity, e.g., 1,4-cis, 1,4-trans-, 3,4-, or 1,2-selectivity.

Scheme 6.

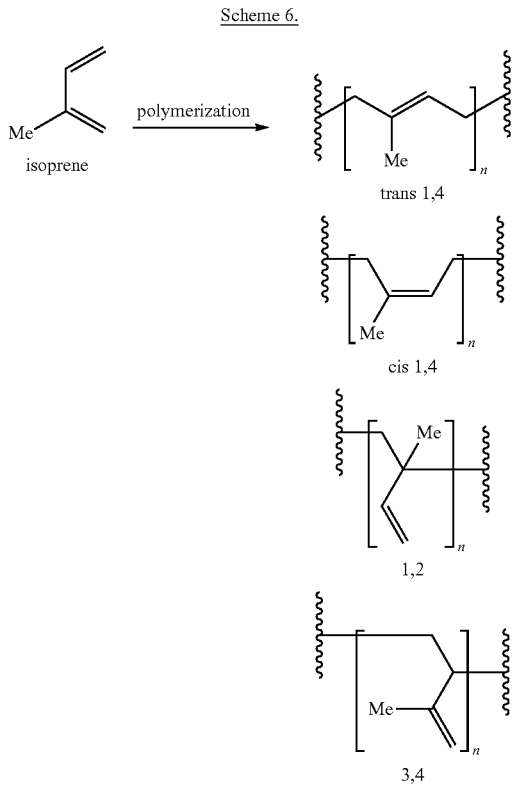

In certain embodiments, $R_a$ and $R_f$ are joined to form an optionally substituted heterocycyl or carbocyclyl ring. In certain embodiments, $R_a$ and $R_f$ are joined to form an optionally substituted carbocyclyl ring (e.g., an optionally substituted 6-membered carbocyclyl ring, e.g., cyclohexyl). In certain embodiments, the diene is cyclohexa-1,3-diene. Polymerization of a 1,3-diene of Formula (i), wherein each instance of $R_b$, $R_c$, $R_d$, and $R_e$ are hydrogen and $R_a$ and $R_f$ are joined to form an cyclohexyl, i.e., cyclohexa-1,3-diene, generates polycyclohexadiene comprising one or more 1,4- or 1,2-units present along the polymer backbone, as depicted in Scheme 7. Thus, in another aspect, provided is a method of preparing polycyclohexadiene comprising polymerizing cyclohexa-1,3-diene in the presence of an iron complex, optionally wherein the polycyclohexadiene, so generated, is provided with a high selectivity, e.g., 1,4- or 1,2-selectivity.

Scheme 7.

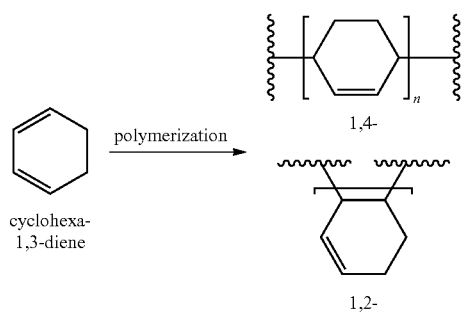

In certain embodiments, the inventive method selectively produces a 1,4-polymer.

For example, in certain embodiments, the polymer produced by the inventive method is at least 50% 1,4. In certain embodiments, the polyisoprene is at least 60% 1,4-polymer. In certain embodiments, the polymer is at least 70% 1,4-polymer. In certain embodiments, the polymer is at least 75% 1,4-polymer. In certain embodiments, the polymer is at least 80% 1,4-polymer. In certain embodiments, the polymer is at least 85% 1,4-polymer. In certain embodiments, the polymer is at least 90% 1,4-polymer. In certain embodiments, the polymer is at least 95% 1,4-polymer. In certain embodiments, the polymer is at least 97% 1,4-polymer. In certain embodiments, the polymer is at least 98% 1,4-polymer. In certain embodiments, the polymer is at least 99% 1,4-polymer. In certain embodiments, the polymer is at least 99.9% 1,4-polymer. In certain embodiments, the polymer is at least 99.99% 1,4-polymer. In certain embodiments, the polymer is greater than 99.99% 1,4-polymer. In certain embodiments, the polymer is 100% 1,4-polymer.

In certain embodiments, the polymer produced by the inventive method is between about 50% to about 100% 1,4-polymer. In certain embodiments, the polymer is between about 60% to about 100% 1,4-polymer. In certain embodiments, the polymer is between about 70% to about 100% 1,4-polymer. In certain embodiments, the polymer is between about 75% to about 100% 1,4-polymer. In certain embodiments, the polymer is between about 80% to about 100% 1,4-polymer. In certain embodiments, the polymer is between about 85% to about 100% 1,4-polymer. In certain embodiments, the polymer is between about 90% to about 100% 1,4-polymer. In certain embodiments, the polymer is between about 95% to about 100% 1,4-polymer. In certain embodiments, the polymer is between about 97% to about 100% 1,4-polymer. In certain embodiments, the polymer is between about 98% to about 100% 1,4-polymer. In certain embodiments, the polymer is between about 99% to about 100% 1,4-polymer. In certain embodiments, the polymer is between about 99.9% to about 100% 1,4-polymer. In certain embodiments, the polymer is between about 99.99% to about 100% 1,4-polymer.

In certain embodiments, the polymer produced by the inventive method comprises a mixture of 1,4-cis-polymer and 1,4-trans-polymer.

In certain embodiments, the polymer predominately comprises 1,4-cis-polymer. For example, in certain embodiments, the polymer comprises 1,4-cis-polymer and 1,4-trans-polymer in a ratio of between about 60:40 to about 100:0 1,4-cis-polymer to 1,4-trans-polymer. In certain embodiments, the polymer comprises 1,4-cis-polymer and 1,4-trans-polymer in a ratio of between about 70:30 to about 100:0 1,4-cis-polymer to 1,4-trans-polymer. In certain embodiments, the polymer comprises 1,4-cis-polymer and 1,4-trans-polymer in a ratio of between about 80:20 to about 100:0 1,4-cis-polymer to 1,4-trans-polymer. In certain embodiments, the polymer comprises 1,4-cis-polymer and 1,4-trans-polymer in a ratio of between about 85:15 to about 100:0 1,4-cis-polymer to 1,4-trans-polymer. In certain embodiments, the polymer comprises 1,4-cis-polymer and 1,4-trans-polymer in a ratio of between about 90:10 to about 100:0 1,4-cis-polymer to 1,4-trans-polymer. In certain embodiments, the polymer comprises 1,4-cis-polymer and 1,4-trans-polymer in a ratio of between about 95:5 to about 100:0 1,4-cis-polymer to 1,4-trans-polymer. In certain embodiments, the polymer comprises 1,4-cis-polymer and 1,4-trans-polymer in a ratio of between about 99:1 to about 100:0 1,4-cis-polymer to 1,4-trans-polymer.

In certain embodiments, the polymer produced by the inventive method is at least 50% 1,4-cis-polymer. In certain embodiments, the polymer is at least 60% 1,4-cis-polymer. In certain embodiments, the polymer is at least 70% 1,4-cis-polymer. In certain embodiments, the polymer is at least 75% 1,4-cis-polymer. In certain embodiments, the polymer is at least 80% 1,4-cis-polymer. In certain embodiments, the polymer is at least 85% 1,4-cis-polymer. In certain embodiments, the polymer is at least 90% 1,4-cis-polymer. In certain embodiments, the polymer is at least 95% 1,4-cis-polymer. In certain embodiments, the polymer is at least 97% 1,4-cis-polymer. In certain embodiments, the polymer is at least 98% 1,4-cis-polymer. In certain embodiments, the polymer is at least 99% 1,4-cis-polymer. In certain embodiments, the polymer is at least 99.9% 1,4-cis-polymer. In certain embodiments, the polymer is at least 99.99% 1,4-cis-polymer. In certain embodiments, the polymer is greater than 99.99% 1,4-cis-polymer.

In certain embodiments, the polymer produced by the inventive method is between about 50% to about 100% 1,4-cis-polymer. In certain embodiments, the polymer is between about 60% to about 100% 1,4-cis-polymer. In certain embodiments, the polymer is between about 70% to about 100% 1,4-cis-polymer. In certain embodiments, the polymer is between about 75% to about 100% 1,4-cis-polymer. In certain embodiments, the polymer is between about 80% to about 100% 1,4-cis-polymer. In certain embodiments, the polymer is between about 85% to about 100% 1,4-cis-polymer. In certain embodiments, the polymer is between about 90% to about 100% 1,4-cis-polymer. In certain embodiments, the polymer is between about 95% to about 100% 1,4-cis-polymer. In certain embodiments, the polymer is between about 97% to about 100% 1,4-cis-polymer. In certain embodiments, the polymer is between about 98% to about 100% 1,4-cis-polymer. In certain embodiments, the polymer is between about 99% to about 100% 1,4-cis-polymer. In certain embodiments, the polymer is between about 99.9% to about 100% 1,4-cis-polymer. In certain embodiments, the polymer is between about 99.99% to about 100% 1,4-cis-polymer.

In certain embodiments, wherein the polymer produced by the inventive method comprises predominately cis-1,4-polymer, the polymer is less than 5% 1,4-trans-polymer. In certain embodiments, the polymer is less than 4% 1,4-trans-polymer. In certain embodiments, the polymer is less than 3% 1,4-trans-polymer. In certain embodiments, the polymer is less than 2% 1,4-trans-polymer. In certain embodiments, the polymer is less than 1% 1,4-trans-polymer. In certain embodiments, the polymer is less than 0.5% 1,4-trans-polymer. In certain embodiments, the polymer is less than 0.1% 1,4-trans-polymer. In certain embodiments, the polymer is less than 0.01% 1,4-trans-polymer.

In certain embodiments, wherein the polymer produced by the inventive method comprises predominately cis-1,4-polymer, the polymer is between about 0% to about 5% 1,4-trans-polymer. In certain embodiments, the polymer is between about 0% to about 5% 1,4-trans-polymer. In certain embodiments, the polymer is between about 0% to about 4% 1,4-trans-polymer. In certain embodiments, the polymer is between about 0% to about 3% 1,4-trans-polymer. In certain embodiments, the polymer is between about 0% to about 1% 1,4-trans-polymer. In certain embodiments, the polymer is between about 1% to about 5% 1,4-trans-polymer.

In certain embodiments, the polymer predominately comprises 1,4-trans-polymer. For example, in certain embodiments, the polymer comprises 1,4-trans-polymer and 1,4-cis-polymer in a ratio of between about 60:40 to about 100:0 1,4-trans-polymer to 1,4-cis-polymer. In certain embodiments, the polymer comprises 1,4-trans-polymer and 1,4-cis-polymer in a ratio of between about 70:30 to about 100:0 1,4-trans-polymer to 1,4-cis-polymer. In certain embodiments, the polymer comprises 1,4-trans-polymer and 1,4-cis-polymer in a ratio of between about 80:20 to about 100:0 1,4-trans-polymer to 1,4-cis-polymer. In certain embodiments, the polymer comprises 1,4-trans-polymer and 1,4-cis-polymer in a ratio of between about 85:15 to about 100:0 1,4-trans-polymer to 1,4-cis-polymer. In certain embodiments, the polymer comprises 1,4-trans-polymer and 1,4-cis-polymer in a ratio of between about 90:10 to about 100:0 1,4-trans-polymer to 1,4-cis-polymer. In certain embodiments, the polymer comprises 1,4-trans-polymer and 1,4-cis-polymer in a ratio of between about 95:5 to about 100:0 1,4-trans-polymer to 1,4-cis-polymer. In certain embodiments, the polymer comprises 1,4-trans-polymer and 1,4-cis-polymer in a ratio of between about 99:1 to about 100:0 1,4-trans-polymer to 1,4-cis-polymer.

In certain embodiments, the polymer produced by the inventive method is at least 50% 1,4-trans-polymer. In certain embodiments, the polymer is at least 60% 1,4-trans-polymer. In certain embodiments, the polymer is at least 70% 1,4-trans-polymer. In certain embodiments, the polymer is at least 75% 1,4-trans-polymer. In certain embodiments, the polymer is at least 80% 1,4-trans-polymer. In certain embodiments, the polymer is at least 85% 1,4-trans-polymer. In certain embodiments, the polymer is at least 90% 1,4-trans-polymer. In certain embodiments, the polymer is at least 95% 1,4-trans-polymer. In certain embodiments, the polymer is at least 97% 1,4-trans-polymer. In certain embodiments, the polymer is at least 98% 1,4-trans-polymer. In certain embodiments, the polymer is at least 99% 1,4-trans-polymer. In certain embodiments, the polymer is at least 99.9% 1,4-trans-polymer. In certain embodiments, the polymer is at least 99.99% 1,4-trans-polymer. In certain embodiments, the polymer is greater than 99.99% 1,4-trans-polymer.

In certain embodiments, the polymer produced by the inventive method is between about 50% to about 100% 1,4-trans-polymer. In certain embodiments, the polymer is between about 60% to about 100% 1,4-trans-polymer. In certain embodiments, the polymer is between about 70% to about 100% 1,4-trans-polymer. In certain embodiments, the polymer is between about 75% to about 100% 1,4-trans-polymer. In certain embodiments, the polymer is between about 80% to about 100% 1,4-trans-polymer. In certain embodiments, the polymer is between about 85% to about 100% 1,4-trans-polymer. In certain embodiments, the polymer is between about 90% to about 100% 1,4-trans-polymer. In certain embodiments, the polymer is between about 95% to about 100% 1,4-trans-polymer. In certain embodiments, the polymer is between about 97% to about 100% 1,4-trans-polymer. In certain embodiments, the polymer is between about 98% to about 100% 1,4-trans-polymer. In certain embodiments, the polymer is between about 99% to about 100% 1,4-trans-polymer. In certain embodiments, the polymer is between about 99.9% to about 100% 1,4-trans-polymer. In certain embodiments, the polymer is between about 99.99% to about 100% 1,4-trans-polymer.

In certain embodiments, wherein the polymer produced by the inventive method comprises predominately trans-1,4-polymer, the polymer is less than 5% 1,4-cis-polymer. In certain embodiments, the polymer is less than 4% 1,4-cis-polymer. In certain embodiments, the polymer is less than 3% 1,4-cis-polymer. In certain embodiments, the polymer is less than 2% 1,4-cis-polymer. In certain embodiments, the polymer is less than 1% 1,4-cis-polymer. In certain embodiments, the polymer is less than 0.5% 1,4-cis-polymer. In certain embodiments, the polymer is less than 0.1% 1,4-cis-polymer. In certain embodiments, the polymer is less than 0.01% 1,4-cis-polymer.

In certain embodiments, wherein the polymer produced by the inventive method comprises predominately trans-1,4-polymer, the polymer is between about 0% to about 5% 1,4-cis-polymer. In certain embodiments, the polymer is between about 0% to about 5% 1,4-cis-polymer. In certain embodiments, the polymer is between about 0% to about 4% 1,4-cis-polymer. In certain embodiments, the polymer is between about 0% to about 3% 1,4-cis-polymer. In certain embodiments, the polymer is between about 0% to about 1% 1,4-cis-polymer. In certain embodiments, the polymer is between about 1% to about 5% 1,4-cis-polymer.

In certain embodiments, the polymer produced by the inventive method is less than 40% 3,4-polymer. In certain embodiments, the polymer is less than 35% 3,4-polymer. In certain embodiments, the polymer is less than 30% 3,4-polymer. In certain embodiments, the polymer is less than 25% 3,4-polymer. In certain embodiments, the polymer is less than 20% 3,4-polymer. In certain embodiments, the polymer is less than 15% 3,4-polymer. In certain embodiments, the polymer is less than 10% 3,4-polymer. In certain embodiments, the polymer is less than 5% 3,4-polymer. In certain embodiments, the polymer is less than 3% 3,4-polymer. In certain embodiments, the polymer is less than 1% 3,4-polymer.

In certain embodiments, the polymer produced by the inventive method is between about 0% to about 40% 3,4-polymer. In certain embodiments, the polymer is between about 0% to about 35% 3,4-polymer. In certain embodiments, the polymer is between about 0% to about 30% 3,4-polymer. In certain embodiments, the polymer is between about 0% to about 25% 3,4-polymer. In certain embodiments, the polymer is between about 0% to about 20% 3,4-polymer. In certain embodiments, the polymer is between about 0% to about 15% 3,4-polymer. In certain embodiments, the polymer is between about 0% to about 10% 3,4-polymer. In certain embodiments, the polymer is between about 0% to about 5% 3,4-polymer. In certain embodiments, the polymer is between about 0% to about 3% 3,4-polymer. In certain embodiments, the polymer is between about 0% to about 1% 3,4-polymer. In certain embodiments, the polymer is between about 0% to about 0.1% 3,4-polymer. In certain embodiments, the polymer does not comprise 3,4-polymer.

In certain embodiments, the polymer produced by the inventive method is less than 10% 1,2-polymer. In certain embodiments, the polymer is less than 5% 1,2-polymer. In certain embodiments, the polymer is less than 4% 1,2-polymer. In certain embodiments, the polymer is less than 3% 1,2-polymer. In certain embodiments, the polymer is less than 2% 1,2-polymer. In certain embodiments, the polymer is less than 1% 1,2-polymer.

In certain embodiments, the polymer produced by the inventive method is between about 0% to about 10% 1,2-polymer. In certain embodiments, the polymer is between about 0% to about 5% 1,2-polymer. In certain embodiments, the polymer is between about 0% to about 4% 1,2-polymer. In certain embodiments, the polymer is between about 0% to about 3% 1,2-polymer. In certain embodiments, the polymer is between about 0% to about 2% 1,2-polymer. In certain embodiments, the polymer is between about 0% to about 1% 1,2-polymer. In certain embodiments, the polymer is between about 0% to about 0.1% 1,2-polymer. In certain embodiments, the does not comprise 1,2-polymer.

However, in certain embodiments, the inventive produces 3,4-polymer selectively. For example, in certain embodiments, the polymer produced by the inventive method is at least 50% 3,4-polymer. In certain embodiments, the polymer is at least 60% 3,4-polymer. In certain embodiments, the polymer is at least 70% 3,4-polymer. In certain embodiments, the polymer is at least 75% 3,4-polymer. In certain embodiments, the polymer is at least 80% 3,4-polymer. In certain embodiments, the polymer is at least 85% 3,4-polymer. In certain embodiments, the polymer is at least 90% 3,4-polymer. In certain embodiments, the polymer is at least 95% 3,4-polymer. In certain embodiments, the polymer is at least 97% 3,4-polymer. In certain embodiments, the polymer is at least 98% 3,4-polymer. In certain embodiments, the polymer is at least 99% 3,4-polymer. In certain embodiments, the polymer is at least 99.9% 3,4-polymer. In certain embodiments, the polymer is at least 99.99% 3,4-polymer. In certain embodiments, the polymer is greater than 99.99% 3,4-polymer. In certain embodiments, the polymer is 100% 3,4-polymer.

Alternatively, in certain embodiments, the inventive produces 1,2-polymer selectively. For example, in certain embodiments, the polymer produced by the inventive method is at least 50% 1,2-polymer. In certain embodiments, the polymer is at least 60% 1,2-polymer. In certain embodiments, the polymer is at least 70% 1,2-polymer. In certain embodiments, the polymer is at least 75% 1,2-polymer. In certain embodiments, the polymer is at least 80% 1,2-polymer. In certain embodiments, the polymer is at least 85% 1,2-polymer. In certain embodiments, the polymer is at least 90% 1,2-polymer. In certain embodiments, the polymer is at least 95% 1,2-polymer. In certain embodiments, the polymer is at least 97% 1,2-polymer. In certain embodiments, the polymer is at least 98% 1,2-polymer. In certain embodiments, the polymer is at least 99% 1,2-polymer. In certain embodiments, the polymer is at least 99.9% 1,2-polymer. In certain embodiments, the polymer is at least 99.99% 1,2-polymer. In certain embodiments, the polymer is greater than 99.99% 1,2-polymer. In certain embodiments, the polymer is 100% 1,2-polymer.

In certain embodiments, the number average molar mass distribution ($M_n$) of the polymer produced by the inventive method is between about 2,000 g/mol to about 5,000,000 g/mol. In certain embodiments, the number average molar mass distribution of the polymer is between about 2,000 g/mol to about 1,000,000 g/mol. In certain embodiments, the number average molar mass distribution of the polymer is between about 2,000 g/mol to about 50,000 g/mol. In certain embodiments, the number average molar mass distribution of the polymer is between about 2,000 g/mol to about 30,000 g/mol. In certain embodiments, the number average molar mass distribution of the polymer is between about 2,000 g/mol to about 10,000 g/mol. In certain embodiments, the number average molar mass distribution of the polymer is between about 50,000 g/mol to about 5,000,000 g/mol. In certain embodiments, the number average molar mass distribution of the polymer is between about 50,000 g/mol to about 2,000,000 g/mol. In certain embodiments, the number average molar mass distribution of the polymer is between about 50,000 g/mol to about 1,000,000 g/mol.

In certain embodiments, the polymer produced by the inventive method is at least 50% 1,4-cis, and has a number average molar mass distribution of between about 2,000 g/mol to about 1,000,000 g/mol. Alternatively, in certain embodiments, the polymer produced by the inventive method is at least 50% 1,4-trans, and has a number average molar mass distribution of between about 2,000 g/mol to about 1,000,000 g/mol.

In certain embodiments, the dispersity of the polymer produced by the inventive method is between about 1 to about 20. In certain embodiments, the dispersity of the polymer is between about 1 to about 10. In certain embodiments, the dispersity of the polymer is between about 1 to about 5. In certain embodiments, the dispersity of the polymer is between about 1 to about 2.

In certain embodiments, the polymer produced by the inventive method is at least 50% 1,4-cis, and has a dispersity of between about 1 to about 2. Alternatively, in certain embodiments, the polymer produced by the inventive method is at least 50% 1,4-trans-, and has a dispersity of between about 1 to about 2.

Polyisoprene

In certain embodiments, the inventive method selectively produces 1,4-polyisoprene.

For example, in certain embodiments, the polyisoprene produced by the inventive method is at least 50% 1,4-polyisoprene. In certain embodiments, the polyisoprene is at least 60% 1,4-polyisoprene. In certain embodiments, the polyisoprene is at least 70% 1,4-polyisoprene. In certain embodiments, the polyisoprene is at least 75% 1,4-polyisoprene. In certain embodiments, the polyisoprene is at least 80% 1,4-polyisoprene. In certain embodiments, the polyisoprene is at least 85% 1,4-polyisoprene. In certain embodiments, the polyisoprene is at least 90% 1,4-polyisoprene. In certain embodiments, the polyisoprene is at least 95% 1,4-polyisoprene. In certain embodiments, the polyisoprene is at least 97% 1,4-polyisoprene. In certain embodiments, the polyisoprene is at least 98% 1,4-polyisoprene. In certain embodiments, the polyisoprene is at least 99% 1,4-polyisoprene. In certain embodiments, the polyisoprene is at least 99.9% 1,4-polyisoprene. In certain embodiments, the polyisoprene is at least 99.99% 1,4-polyisoprene. In certain embodiments, the polyisoprene is greater than 99.99% 1,4-polyisoprene. In certain embodiments, the polyisoprene is 100% 1,4-polyisoprene.

In certain embodiments, the polyisoprene produced by the inventive method is between about 50% to about 100% 1,4-polyisoprene. In certain embodiments, the polyisoprene is between about 60% to about 100% 1,4-polyisoprene. In certain embodiments, the polyisoprene is between about 70% to about 100% 1,4-polyisoprene. In certain embodiments, the polyisoprene is between about 75% to about 100% 1,4-polyisoprene. In certain embodiments, the polyisoprene is between about 80% to about 100% 1,4-polyisoprene. In certain embodiments, the polyisoprene is between about 85% to about 100% 1,4-polyisoprene. In certain embodiments, the polyisoprene is between about 90% to about 100% 1,4-polyisoprene. In certain embodiments, the polyisoprene is between about 95% to about 100% 1,4-polyisoprene. In certain embodiments, the polyisoprene is between about 97% to about 100% 1,4-polyisoprene. In certain embodiments, the polyisoprene is between about 98% to about 100% 1,4-polyisoprene. In certain embodiments, the polyisoprene is between about 99% to about 100% 1,4-polyisoprene. In certain embodiments, the polyisoprene is between about 99.9% to about 100% 1,4-polyisoprene. In certain embodiments, the polyisoprene is between about 99.99% to about 100% 1,4-polyisoprene.

In certain embodiments, the polyisoprene produced by the inventive method comprises a mixture of 1,4-cis-polyisoprene and 1,4-trans-polyisoprene.

In certain embodiments, the polyisoprene predominately comprises 1,4-cis-polyisoprene. For example, in certain embodiments, the polyisoprene comprises 1,4-cis-polyisoprene and 1,4-trans-polyisoprene in a ratio of between about 60:40 to about 100:0 1,4-cis-polyisoprene to 1,4-trans-polyisoprene. In certain embodiments, the polyisoprene comprises 1,4-cis-polyisoprene and 1,4-trans-polyisoprene in a ratio of between about 70:30 to about 100:0 1,4-cis-polyisoprene to 1,4-trans-polyisoprene. In certain embodiments, the polyisoprene comprises 1,4-cis-polyisoprene and 1,4-trans-polyisoprene in a ratio of between about 80:20 to about 100:0 1,4-cis-polyisoprene to 1,4-trans-polyisoprene. In certain embodiments, the polyisoprene comprises 1,4-cis-polyisoprene and 1,4-trans-polyisoprene in a ratio of between about 85:15 to about 100:0 1,4-cis-polyisoprene to 1,4-trans-polyisoprene. In certain embodiments, the polyisoprene comprises 1,4-cis-polyisoprene and 1,4-trans-polyisoprene in a ratio of between about 90:10 to about 100:0 1,4-cis-polyisoprene to 1,4-trans-polyisoprene. In certain embodiments, the polyisoprene comprises 1,4-cis-polyisoprene and 1,4-trans-polyisoprene in a ratio of between about 95:5 to about 100:0 1,4-cis-polyisoprene to 1,4-trans-polyisoprene. In certain embodiments, the polyisoprene comprises 1,4-cis-polyisoprene and 1,4-trans-polyisoprene in a ratio of between about 99:1 to about 100:0 1,4-cis-polyisoprene to 1,4-trans-polyisoprene.

In certain embodiments, the polyisoprene produced by the inventive method is at least 50% 1,4-cis-polyisoprene. In certain embodiments, the polyisoprene is at least 60% 1,4-cis-polyisoprene. In certain embodiments, the polyisoprene is at least 70% 1,4-cis-polyisoprene. In certain embodiments, the polyisoprene is at least 75% 1,4-cis-polyisoprene. In certain embodiments, the polyisoprene is at least 80% 1,4-cis-polyisoprene. In certain embodiments, the polyisoprene is at least 85% 1,4-cis-polyisoprene. In certain embodiments, the polyisoprene is at least 90% 1,4-cis-polyisoprene. In certain embodiments, the polyisoprene is at least 95% 1,4-cis-polyisoprene. In certain embodiments, the polyisoprene is at least 97% 1,4-cis-polyisoprene. In certain embodiments, the polyisoprene is at least 98% 1,4-cis-polyisoprene. In certain embodiments, the polyisoprene is at least 99% 1,4-cis-polyisoprene. In certain embodiments, the polyisoprene is at least 99.9% 1,4-cis-polyisoprene. In certain embodiments, the polyisoprene is at least 99.99% 1,4-cis-polyisoprene. In certain embodiments, the polyisoprene is greater than 99.99% 1,4-cis-polyisoprene.

In certain embodiments, the polyisoprene produced by the inventive method is between about 50% to about 100% 1,4-cis-polyisoprene. In certain embodiments, the polyisoprene is between about 60% to about 100% 1,4-cis-polyisoprene. In certain embodiments, the polyisoprene is between about 70% to about 100% 1,4-cis-polyisoprene. In certain embodiments, the polyisoprene is between about 75% to about 100% 1,4-cis-polyisoprene. In certain embodiments, the polyisoprene is between about 80% to about 100% 1,4-cis-polyisoprene. In certain embodiments, the polyisoprene is between about 85% to about 100% 1,4-cis-polyisoprene. In certain embodiments, the polyisoprene is between about 90% to about 100% 1,4-cis-polyisoprene. In certain embodiments, the polyisoprene is between about 95% to about 100% 1,4-cis-polyisoprene. In certain embodiments, the polyisoprene is between about 97% to about 100% 1,4-cis-polyisoprene. In certain embodiments, the polyisoprene is between about 98% to about 100% 1,4-cis-polyisoprene. In certain embodiments, the polyisoprene is between about 99% to about 100% 1,4-cis-polyisoprene. In certain embodiments, the polyisoprene is between about 99.9% to about 100% 1,4-cis-polyisoprene. In certain embodiments, the polyisoprene is between about 99.99% to about 100% 1,4-cis-polyisoprene.

In certain embodiments, wherein the polyisoprene produced by the inventive method comprises predominately cis-1,4-polyisoprene, the polyisoprene is less than 5% 1,4-trans-polyisoprene. In certain embodiments, the polyisoprene is less than 4% 1,4-trans-polyisoprene. In certain embodiments, the polyisoprene is less than 3% 1,4-trans-polyisoprene. In certain embodiments, the polyisoprene is less than 2% 1,4-trans-polyisoprene. In certain embodiments, the polyisoprene is less than 1% 1,4-trans-polyisoprene. In certain embodiments, the polyisoprene is less than 0.5% 1,4-trans-polyisoprene. In certain embodiments, the polyisoprene is less than 0.1% 1,4-trans-polyisoprene. In certain embodiments, the polyisoprene is less than 0.01% 1,4-trans-polyisoprene.

In certain embodiments, wherein the polyisoprene produced by the inventive method comprises predominately cis-1,4-polyisoprene, the polyisoprene is between about 0% to about 5% 1,4-trans-polyisoprene. In certain embodiments, the polyisoprene is between about 0% to about 5% 1,4-trans-polyisoprene. In certain embodiments, the polyisoprene is between about 0% to about 4% 1,4-trans-polyisoprene. In certain embodiments, the polyisoprene is between about 0% to about 3% 1,4-trans-polyisoprene. In certain embodiments, the polyisoprene is between about 0% to about 1% 1,4-trans-polyisoprene. In certain embodiments, the polyisoprene is between about 1% to about 5% 1,4-trans-polyisoprene.

In certain embodiments, the polyisoprene predominately comprises 1,4-trans-polyisoprene. For example, in certain embodiments, the polyisoprene comprises 1,4-trans-polyisoprene and 1,4-cis-polyisoprene in a ratio of between about 60:40 to about 100:0 1,4-trans-polyisoprene to 1,4-cis-polyisoprene. In certain embodiments, the polyisoprene comprises 1,4-trans-polyisoprene and 1,4-cis-polyisoprene in a ratio of between about 70:30 to about 100:0 1,4-trans-polyisoprene to 1,4-cis-polyisoprene. In certain embodiments, the polyisoprene comprises 1,4-trans-polyisoprene and 1,4-cis-polyisoprene in a ratio of between about 80:20 to about 100:0 1,4-trans-polyisoprene to 1,4-cis-polyisoprene. In certain embodiments, the polyisoprene comprises 1,4-trans-polyisoprene and 1,4-cis-polyisoprene in a ratio of between about 85:15 to about 100:0 1,4-trans-polyisoprene to 1,4-cis-polyisoprene. In certain embodiments, the polyisoprene comprises 1,4-trans-polyisoprene and 1,4-cis-polyisoprene in a ratio of between about 90:10 to about 100:0 1,4-trans-polyisoprene to 1,4-cis-polyisoprene. In certain embodiments, the polyisoprene comprises 1,4-trans-polyisoprene and 1,4-cis-polyisoprene in a ratio of between about 95:5 to about 100:0 1,4-trans-polyisoprene to 1,4-cis-polyisoprene. In certain embodiments, the polyisoprene comprises 1,4-trans-polyisoprene and 1,4-cis-polyisoprene in a ratio of between about 99:1 to about 100:0 1,4-trans-polyisoprene to 1,4-cis-polyisoprene.

In certain embodiments, the polyisoprene produced by the inventive method is at least 50% 1,4-trans-polyisoprene. In certain embodiments, the polyisoprene is at least 60% 1,4-trans-polyisoprene. In certain embodiments, the polyisoprene is at least 70% 1,4-trans-polyisoprene. In certain embodiments, the polyisoprene is at least 75% 1,4-trans-polyisoprene. In certain embodiments, the polyisoprene is at least 80% 1,4-trans-polyisoprene. In certain embodiments, the polyisoprene is at least 85% 1,4-trans-polyisoprene. In certain embodiments, the polyisoprene is at least 90% 1,4-trans-polyisoprene. In certain embodiments, the polyisoprene is at least 95% 1,4-trans-polyisoprene. In certain embodiments, the polyisoprene is at least 97% 1,4-trans-polyisoprene. In certain embodiments, the polyisoprene is at least 98% 1,4-trans-polyisoprene. In certain embodiments, the polyisoprene is at least 99% 1,4-trans-polyisoprene. In certain embodiments, the polyisoprene is at least 99.9% 1,4-trans-polyisoprene. In certain embodiments, the polyisoprene is at least 99.99% 1,4-trans-polyisoprene. In certain embodiments, the polyisoprene is greater than 99.99% 1,4-trans-polyisoprene.

In certain embodiments, the polyisoprene produced by the inventive method is between about 50% to about 100% 1,4-trans-polyisoprene. In certain embodiments, the polyisoprene is between about 60% to about 100% 1,4-trans-polyisoprene. In certain embodiments, the polyisoprene is between about 70% to about 100% 1,4-trans-polyisoprene. In certain embodiments, the polyisoprene is between about 75% to about 100% 1,4-trans-polyisoprene. In certain embodiments, the polyisoprene is between about 80% to about 100% 1,4-trans-polyisoprene. In certain embodiments, the polyisoprene is between about 85% to about 100% 1,4-trans-polyisoprene. In certain embodiments, the polyisoprene is between about 90% to about 100% 1,4-trans-polyisoprene. In certain embodiments, the polyisoprene is between about 95% to about 100% 1,4-trans-polyisoprene. In certain embodiments, the polyisoprene is between about 97% to about 100% 1,4-trans-polyisoprene. In certain embodiments, the polyisoprene is between about 98% to about 100% 1,4-trans-polyisoprene. In certain embodiments, the polyisoprene is between about 99% to about 100% 1,4-trans-polyisoprene. In certain embodiments, the polyisoprene is between about 99.9% to about 100% 1,4-trans-polyisoprene. In certain embodiments, the polyisoprene is between about 99.99% to about 100% 1,4-trans-polyisoprene.

In certain embodiments, wherein the polyisoprene produced by the inventive method comprises predominately trans-1,4-polyisoprene, the polyisoprene is less than 5% 1,4-cis-polyisoprene. In certain embodiments, the polyisoprene is less than 4% 1,4-cis-polyisoprene. In certain embodiments, the polyisoprene is less than 3% 1,4-cis-polyisoprene. In certain embodiments, the polyisoprene is less than 2% 1,4-cis-polyisoprene. In certain embodiments, the polyisoprene is less than 1% 1,4-cis-polyisoprene. In certain embodiments, the polyisoprene is less than 0.5% 1,4-cis-polyisoprene. In certain embodiments, the polyisoprene is less than 0.1% 1,4-cis-polyisoprene. In certain embodiments, the polyisoprene is less than 0.01% 1,4-cis-polyisoprene.

In certain embodiments, wherein the polyisoprene produced by the inventive method comprises predominately trans-1,4-polyisoprene, the polyisoprene is between about 0% to about 5% 1,4-cis-polyisoprene. In certain embodiments, the polyisoprene is between about 0% to about 5% 1,4-cis-polyisoprene. In certain embodiments, the polyisoprene is between about 0% to about 4% 1,4-cis-polyisoprene. In certain embodiments, the polyisoprene is between about 0% to about 3% 1,4-cis-polyisoprene. In certain embodiments, the polyisoprene is between about 0% to about 1% 1,4-cis-polyisoprene. In certain embodiments, the polyisoprene is between about 1% to about 5% 1,4-cis-polyisoprene.

In certain embodiments, the polyisoprene produced by the inventive method is less than 40% 3,4-polyisoprene. In certain embodiments, the polyisoprene is less than 35% 3,4-polyisoprene. In certain embodiments, the polyisoprene is less than 30% 3,4-polyisoprene. In certain embodiments, the polyisoprene is less than 25% 3,4-polyisoprene. In certain embodiments, the polyisoprene is less than 20% 3,4-polyisoprene. In certain embodiments, the polyisoprene is less than 15% 3,4-polyisoprene. In certain embodiments, the polyisoprene is less than 10% 3,4-polyisoprene. In certain embodiments, the polyisoprene is less than 5% 3,4-polyisoprene. In certain embodiments, the polyisoprene is less than 3% 3,4-polyisoprene. In certain embodiments, the polyisoprene is less than 1% 3,4-polyisoprene.

In certain embodiments, the polyisoprene produced by the inventive method is between about 0% to about 40% 3,4-polyisoprene. In certain embodiments, the polyisoprene is between about 0% to about 35% 3,4-polyisoprene. In certain embodiments, the polyisoprene is between about 0% to about 30% 3,4-polyisoprene. In certain embodiments, the polyisoprene is between about 0% to about 25% 3,4-polyisoprene. In certain embodiments, the polyisoprene is between about 0% to about 20% 3,4-polyisoprene. In certain embodiments, the polyisoprene is between about 0% to about 15% 3,4-polyisoprene. In certain embodiments, the polyisoprene is between about 0% to about 10% 3,4-polyisoprene. In certain embodiments, the polyisoprene is between about 0% to about 5% 3,4-polyisoprene. In certain embodiments, the polyisoprene is between about 0% to about 3% 3,4-polyisoprene. In certain embodiments, the polyisoprene is between about 0% to about 1% 3,4-polyisoprene. In certain embodiments, the polyisoprene is between about 0% to about 0.1% 3,4-polyisoprene. In certain embodiments, the polyisoprene does not comprise 3,4-polyisoprene.

In certain embodiments, the polyisoprene produced by the inventive method is less than 10% 1,2-polyisoprene. In certain embodiments, the polyisoprene is less than 5% 1,2-polyisoprene. In certain embodiments, the polyisoprene is less than 4% 1,2-polyisoprene. In certain embodiments, the polyisoprene is less than 3% 1,2-polyisoprene. In certain embodiments, the polyisoprene is less than 2% 1,2-polyisoprene. In certain embodiments, the polyisoprene is less than 1% 1,2-polyisoprene.

In certain embodiments, the polyisoprene produced by the inventive method is between about 0% to about 10% 1,2-polyisoprene. In certain embodiments, the polyisoprene is between about 0% to about 5% 1,2-polyisoprene. In certain embodiments, the polyisoprene is between about 0% to about 4% 1,2-polyisoprene. In certain embodiments, the polyisoprene is between about 0% to about 3% 1,2-polyisoprene. In certain embodiments, the polyisoprene is between about 0% to about 2% 1,2-polyisoprene. In certain embodiments, the polyisoprene is between about 0% to about 1% 1,2-polyisoprene. In certain embodiments, the polyisoprene is between about 0% to about 0.1% 1,2-polyisoprene. In certain embodiments, the does not comprise 1,2-polyisoprene.

However, in certain embodiments, the inventive produces 3,4-polyisoprene selectively. For example, in certain embodiments, the polyisoprene produced by the inventive method is at least 50% 3,4-polyisoprene. In certain embodiments, the polyisoprene is at least 60% 3,4-polyisoprene. In certain embodiments, the polyisoprene is at least 70% 3,4-polyisoprene. In certain embodiments, the polyisoprene is at least 75% 3,4-polyisoprene. In certain embodiments, the polyisoprene is at least 80% 3,4-polyisoprene. In certain embodiments, the polyisoprene is at least 85% 3,4-polyisoprene. In certain embodiments, the polyisoprene is at least 90% 3,4-polyisoprene. In certain embodiments, the polyisoprene is at least 95% 3,4-polyisoprene. In certain embodiments, the polyisoprene is at least 97% 3,4-polyisoprene. In certain embodiments, the polyisoprene is at least 98% 3,4-polyisoprene. In certain embodiments, the polyisoprene is at least 99% 3,4-polyisoprene. In certain embodiments, the polyisoprene is at least 99.9% 3,4-polyisoprene. In certain embodiments, the polyisoprene is at least 99.99% 3,4-polyisoprene. In certain embodiments, the polyisoprene is greater than 99.99% 3,4-polyisoprene. In certain embodiments, the polyisoprene is 100% 3,4-polyisoprene.

Alternatively, in certain embodiments, the inventive produces 1,2-polyisoprene selectively. For example, in certain embodiments, the polyisoprene produced by the inventive method is at least 50% 1,2-polyisoprene. In certain embodiments, the polyisoprene is at least 60% 1,2-polyisoprene. In certain embodiments, the polyisoprene is at least 70% 1,2-polyisoprene. In certain embodiments, the polyisoprene is at least 75% 1,2-polyisoprene. In certain embodiments, the polyisoprene is at least 80% 1,2-polyisoprene. In certain embodiments, the polyisoprene is at least 85% 1,2-polyisoprene. In certain embodiments, the polyisoprene is at least 90% 1,2-polyisoprene. In certain embodiments, the polyisoprene is at least 95% 1,2-polyisoprene. In certain embodiments, the polyisoprene is at least 97% 1,2-polyisoprene. In certain embodiments, the polyisoprene is at least 98% 1,2-polyisoprene. In certain embodiments, the polyisoprene is at least 99% 1,2-polyisoprene. In certain embodiments, the polyisoprene is at least 99.9% 1,2-polyisoprene. In certain embodiments, the polyisoprene is at least 99.99% 1,2-polyisoprene. In certain embodiments, the polyisoprene is greater than 99.99% 1,2-polyisoprene. In certain embodiments, the polyisoprene is 100% 1,2-polyisoprene.

Iron Complexes

As generally described above, the present invention is based on the discovery that iron complexes may polymerize an alkene, e.g., isoprene, optionally selectively providing a polymer with high 1,4-, 3,4-, or 1,2-microstructure. In certain embodiments, the iron of the metal complex has a valency of (0). In certain embodiments, the iron of the metal complex has a valency of (II). The invention provides iron complexes as well as compositions, kits, systems, and methods of using and preparing the complexes as described herein. Exemplary iron complexes include, but are not limited to, iron complexes described in Moreau et al., *Org. Lett.* (2009) 11:337-339; Wu et al., *J. Am. Chem. Soc.* (2009) 131:12915-12917; and Wu et al., *J. Am. Chem. Soc.* (2010) 132:13214-13216, as well as iron complexes described herein.

In certain embodiments, the metal complex comprises iron and a ligand of the Formula (A):

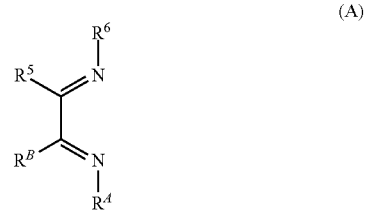

wherein:

$R^5$ selected from the group consisting of hydrogen, halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, phosphino, boronyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;

$R^6$ is selected from the group consisting of substituted hydroxyl, substituted thiol, monosubstituted amino, disubstituted amino, trisubstituted amino, sulfonyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^5$ and $R^6$ are joined to form a ring selected from optionally substituted heterocyclyl and optionally substituted heteroaryl;

$R^A$ is selected from optionally substituted alkyl, optionally substituted alkenyl, optionally substituted alkynyl, optionally substituted carbocyclyl, optionally substituted heterocyclyl, optionally substituted aryl, and optionally substituted heteroaryl; and $R^B$ is selected from hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^A$ and $R^B$ are joined to form a ring selected from optionally substituted heterocyclyl and optionally substituted heteroaryl; or $R^B$ and $R^5$ are joined to form a ring selected from an optionally substituted carbocyclyl, optionally substituted heterocyclyl, optionally substituted aryl, or optionally substituted heteroaryl ring; or $R^B$ is joined to both $R^A$ and $R^5$ in order to form a fused heterocyclic or heteroaryl ring system.

In certain embodiments, the ligand of Formula (A) is of the Formula (B):

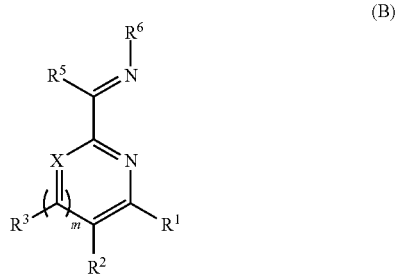

(B)

wherein:

m is 0 or 1, provided that when m is 0, X is N—$R^4$; and when m is 1, X is N or C—$R^4$;

each instance of $R^1$, $R^2$, $R^3$, $R^4$, and $R^5$ is independently selected from the group consisting of hydrogen, halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, phosphino, boronyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^1$ and $R^2$, or $R^2$ and $R^3$, or $R^2$ and $R^4$, or $R^3$ and $R^4$, or $R^4$ and $R^5$, are optionally joined to form a ring selected from an optionally substituted carbocyclyl, optionally substituted heterocyclyl, optionally substituted aryl, or optionally substituted heteroaryl ring; and $R^6$ is selected from the group consisting of substituted hydroxyl, substituted thiol, monosubstituted amino, disubstituted amino, trisubstituted amino, sulfonyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^5$ and $R^6$ are joined to form a ring selected from optionally substituted heterocyclyl and optionally substituted heteroaryl.

In certain embodiments, wherein m is 0 and X is N—$R^4$, the ligand of Formula (B) is of the Formula (C-I):

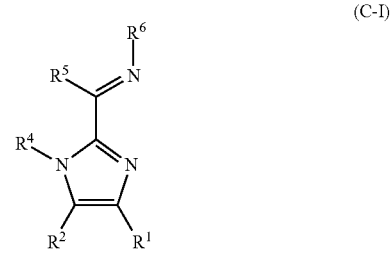

(C-I)

wherein $R^1$, $R^2$, $R^4$, $R^5$ and $R^6$ are as defined herein.

In certain embodiments, wherein m is 1 and X is N, the ligand of Formula (B) is of the Formula (D-I):

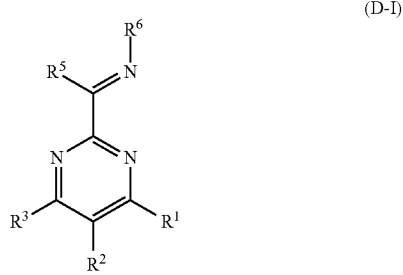

(D-I)

wherein $R^1$, $R^2$, $R^3$, $R^5$ and $R^6$ are as defined herein.

In certain embodiments, wherein m is 1 and X is C—R$_4$, the ligand of Formula (B) is of the Formula (E-I):

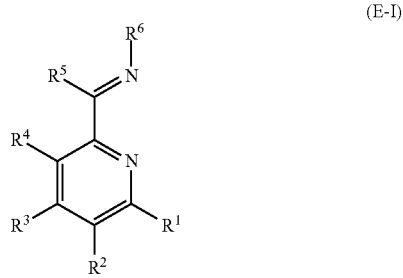

(E-I)

wherein $R^1$, $R^2$, $R^3$, $R^4$, $R^5$ and $R^6$ are as defined herein.

In certain embodiments, $R^1$ and $R^2$ are not joined to form a ring. In certain embodiments, $R^2$ and $R^3$ are not joined to form a ring. In certain embodiments, $R^3$ and $R^4$ are not joined to form a ring. In certain embodiments, $R^4$ and $R^5$ are not joined to form a ring. In this instance wherein $R^4$ and $R^5$ are not joined to form a ring, the ligand cannot be 1,10-phenanthroline. In certain embodiments, $R^5$ and $R^6$ are not joined to form a ring.

For example, in certain embodiments, each instance of $R^1$, $R^2$, $R^3$, $R^4$, and $R^5$, is independently selected from the group consisting of hydrogen, halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, phosphino, boronyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; and $R^6$ is selected from the group consisting of substituted hydroxyl, substituted thiol, monosubstituted amino, disubstituted amino, trisubstituted amino, sulfonyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl.

In certain embodiments, $R^1$ is selected from hydrogen, halogen, substituted hydroxyl, and optionally substituted alkyl. In certain embodiments, $R^1$ is hydrogen. In certain embodiments, $R^1$ is halogen, i.e., —F, —Br, —I, or —Cl. In certain embodiments, $R^1$ is substituted hydroxyl, e.g., —OCH$_3$. In certain embodiments, $R^1$ is optionally substituted $C_{1-6}$ alkyl. In certain embodiments, $R^1$ is optionally substituted $C_{1-4}$ alkyl. In certain embodiments, $R^1$ is optionally substituted $C_{1-3}$ alkyl. In certain embodiments, $R^1$ is —C(CH$_3$)$_3$ (-tBu). In certain embodiments, $R^1$ is —CH(CH$_3$)$_2$ (-iPr). In certain embodiments, $R^1$ is —CH$_2$CH$_2$CH$_3$ (-nPr). In certain embodiments, $R^1$ is —CH$_2$CH$_3$ (-Et). In certain embodiments, $R^1$ is —CH$_3$ (-Me). In certain embodiments, $R^1$ is —CH$_2$Si(CH$_3$)$_3$.

In certain embodiments, $R^2$ is selected from hydrogen and optionally substituted alkyl. In certain embodiments, $R^2$ is hydrogen. In certain embodiments, $R^2$ is optionally substituted $C_{1-6}$ alkyl. In certain embodiments, $R^2$ is optionally substituted $C_{1-4}$ alkyl. In certain embodiments, $R^2$ is optionally substituted $C_{1-3}$ alkyl. In certain embodiments, $R^2$ is —C(CH$_3$)$_3$ (-tBu). In certain embodiments, $R^2$ is —CH(CH$_3$)$_2$ (-iPr). In certain embodiments, $R^2$ is —CH$_2$CH$_2$CH$_3$ (-nPr). In certain embodiments, $R^2$ is —CH$_2$CH$_3$ (-Et). In certain embodiments, $R^2$ is —CH$_3$ (-Me). In certain embodiments, $R^2$ is —CH$_2$Si(CH$_3$)$_3$.

In certain embodiments, $R^3$ is selected from hydrogen, substituted hydroxyl, and optionally substituted alkyl. In certain embodiments, $R^3$ is hydrogen. In certain embodiments, $R^3$ is substituted hydroxyl, e.g., —OCH$_3$. In certain embodiments, $R^3$ is optionally substituted $C_{1-6}$ alkyl. In certain embodiments, $R^3$ is optionally substituted $C_{1-4}$ alkyl. In certain embodiments, $R^3$ is optionally substituted $C_{1-3}$ alkyl. In certain embodiments, $R^3$ is —C(CH$_3$)$_3$ (-tBu). In certain embodiments, $R^3$ is —CH(CH$_3$)$_2$ (-iPr). In certain embodiments, $R^3$ is —CH$_2$CH$_2$CH$_3$ (-nPr). In certain embodiments, $R^3$ is —CH$_2$CH$_3$ (-Et). In certain embodiments, $R^3$ is —CH$_3$ (-Me). In certain embodiments, $R^3$ is —CH$_2$Si(CH$_3$)$_3$.

In certain embodiments, $R^4$ is selected from hydrogen and optionally substituted alkyl. In certain embodiments, $R^4$ is hydrogen. In certain embodiments, $R^4$ is optionally substituted $C_{1-6}$ alkyl. In certain embodiments, $R^4$ is optionally substituted $C_{1-4}$ alkyl. In certain embodiments, $R^4$ is optionally substituted $C_{1-3}$ alkyl. In certain embodiments, $R^4$ is —C(CH$_3$)$_3$ (-tBu). In certain embodiments, $R^4$ is —CH(CH$_3$)$_2$ (-iPr). In certain embodiments, $R^4$ is —CH$_2$CH$_2$CH$_3$ (-nPr). In certain embodiments, $R^4$ is —CH$_2$CH$_3$ (-Et). In certain embodiments, $R^4$ is —CH$_3$ (-Me). In certain embodiments, $R^4$ is —CH$_2$Si(CH$_3$)$_3$.

In certain embodiments, $R^5$ is selected from hydrogen and optionally substituted alkyl. In certain embodiments, $R^5$ is hydrogen. In certain embodiments, $R^5$ is optionally substituted $C_{1-6}$ alkyl. In certain embodiments, $R^5$ is optionally substituted $C_{1-4}$ alkyl. In certain embodiments, $R^5$ is optionally substituted $C_{1-3}$ alkyl. In certain embodiments, $R^5$ is —C(CH$_3$)$_3$ (-tBu). In certain embodiments, $R^5$ is —CH(CH$_3$)$_2$ (-iPr). In certain embodiments, $R^5$ is —CH$_2$CH$_2$CH$_3$ (-nPr). In certain embodiments, $R^5$ is —CH$_2$CH$_3$ (-Et). In certain embodiments, $R^5$ is —CH$_3$ (-Me). In certain embodiments, $R^5$ is —CH$_2$Si(CH$_3$)$_3$.

In certain embodiments, each of $R^1$, $R^2$, $R^3$, and $R^4$ are hydrogen. In certain embodiments, each of $R^1$, $R^2$, $R^3$, $R^4$, and $R^5$ are hydrogen.

However, in certain embodiments, each of $R^2$, $R^3$, $R^4$, and $R^5$ are hydrogen; and $R^1$ is selected from the group consisting of halogen, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl.

In certain embodiments, each of $R^2$, $R^3$, $R^4$, and $R^5$ are hydrogen; and $R^1$ is optionally substituted alkyl. In certain embodiments, each of $R^2$, $R^3$, $R^4$, and $R^5$ are hydrogen; and $R^1$ is optionally substituted $C_{1-6}$ alkyl. In certain embodiments, each of $R^2$, $R^3$, $R^4$, and $R^5$ are hydrogen; and $R^1$ is optionally substituted $C_{1-4}$ alkyl. In certain embodiments, each of $R^2$, $R^3$, $R^4$, and $R^5$ are hydrogen; and $R^1$ is optionally substituted $C_{1-3}$ alkyl. In certain embodiments, each of $R^2$, $R^3$, $R^4$, and $R^5$ are hydrogen; and $R^1$ is —C(CH$_3$)$_3$ (-tBu). In certain embodiments, each of $R^2$, $R^3$, $R^4$, and $R^5$ are hydrogen; and $R^1$ is —CH(CH$_3$)$_2$ (-iPr). In certain embodiments, each of $R^2$, $R^3$, $R^4$, and $R^5$ are hydrogen; and $R^1$ is —CH$_2$CH$_2$CH$_3$ (-nPr). In certain embodiments, each of $R^2$, $R^3$, $R^4$, and $R^5$ are hydrogen; and $R^1$ is —CH$_2$CH$_3$ (-Et). In certain embodiments, each of $R^2$, $R^3$, $R^4$, and $R^5$ are hydrogen; and $R^1$ is —CH$_3$ (-Me). In certain embodiments, each of $R^2$, $R^3$, $R^4$, and $R^5$ are hydrogen; and $R^1$ is —CH$_2$Si(CH$_3$)$_3$.

In certain embodiments, $R^6$ is selected from substituted hydroxyl, optionally substituted alkyl, optionally substituted alkenyl, optionally substituted alkynyl, optionally substituted carbocyclyl, optionally substituted heterocyclyl, optionally substituted aryl, and optionally substituted heteroaryl. In certain embodiments, $R^6$ is selected from optionally substituted alkyl, optionally substituted carbocyclyl, optionally substituted aryl, and optionally substituted heteroaryl. In certain embodiments, $R^6$ is optionally substituted alkyl. In certain embodiments, $R^6$ is selected from optionally substituted alkyl. In certain embodiments, $R^6$ is substituted alkyl. In certain embodiments, $R^6$ is optionally substituted aralkyl or optionally substituted heteroaralkyl (i.e., alkyl substituted by optionally substituted aryl or heteroaryl). In certain embodiments, $R^6$ is optionally substituted aryl (e.g., optionally substituted phenyl). In certain embodiments, $R^6$ is selected from a monosubstituted aryl, a disubstituted aryl, or a trisubstituted aryl.

In certain embodiments, the metal complex is an iron complex of the Formula (A-II):

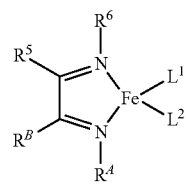

(A-II)

wherein $R^A$, $R^B$, $R^5$, and $R^6$ are as defined herein; and $L^1$ and $L^2$ are monodentate ligands independently selected from the group consisting of hydrogen, $H_2O$, $-NH_3$, $-SCN$, $-N_3$, $-N_2$, $-ONO_3$, $-NO_2$, $-ONO$, $-NCCH_3$, $-NC$, $-CN$, $-CO$, halogen, amino, monosubstituted amino, disubstituted amino, trisubstituted amino, hydroxyl, substituted hydroxyl, thiol, substituted thiol, phosphino, phosphono, phosphoramido, silyl, boronyl, stannyl, germyl, arsenyl, carbonyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $L^1$ and $L^2$ are a bidentate ligand independently selected from $-NH_2$, monosubstituted amino, disubstituted amino, phosphino, silyl, boronyl, $-OH$, $-O-$, $-CN$, optionally substituted alkyl, optionally substituted alkenyl, optionally substituted alkynyl, optionally substituted carbocyclyl, optionally substituted heterocyclyl, optionally substituted aryl, and optionally substituted heteroaryl, wherein $L^1$ and $L^2$ are joined by one or more bonds or divalent groups selected from divalent alkyl, divalent alkenyl, divalent alkynyl, divalent carbocyclyl, divalent heterocyclyl, divalent aryl, and divalent heteroaryl.

In certain embodiments, the iron complex useful any of the above inventive processes is of the Formula (B-II):

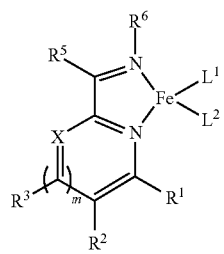

(B-II)

wherein $L^1$, $L^2$, X, m, $R^1$, $R^2$, $R^3$, $R^5$, and $R^6$ are as defined herein.

For example, wherein m is 1 and X is C—$R^4$, provided is a complex of the Formula (E-II):

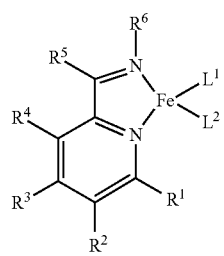

(E-II)

wherein $R^1$, $R^2$, $R^3$, $R^4$, $R^5$, $R^6$, $L^1$ and $L^2$ areas defined herein.

In certain embodiments, the iron of the metal complex has a valency of (0). In certain embodiments, the iron of the metal complex has a valency of (II).

In certain embodiments, $L^1$ and $L^2$ are monodentate ligands.

In certain embodiments, wherein $L^1$ and $L^2$ are monodentate ligands, $L^1$ and $L^2$ are independently selected from halogen, $NH_3$, trisubstituted amino, phosphino, silyl, boronyl, $H_2O$, $-OH$, $-SCN$, $-N_3$, $-ONO_3$, $-NO_2$, $-ONO$, $-NCCH_3$, $-NC$, $-CN$, $-CO$, substituted hydroxyl, optionally substituted alkyl, optionally substituted alkenyl, optionally substituted alkynyl, optionally substituted carbocyclyl, optionally substituted heterocyclyl, optionally substituted aryl, and optionally substituted heteroaryl. In certain embodiments, wherein $L^1$ and $L^2$ are monodentate ligands, $L^1$ and $L^2$ both independently selected from halogen and substituted hydroxyl. In certain embodiments, wherein $L^1$ and $L^2$ are monodentate ligands, both $L^1$ and $L^2$ are halogen. In certain embodiments, both $L^1$ and $L^2$ are chloro. In certain embodiments, both $L^1$ and $L^2$ are bromo. In certain embodiments, both $L^1$ and $L^2$ are substituted hydroxyl (e.g., $-OAc$ ($-OC=OCH_3$)).

For example, in certain embodiments, wherein $L^1$ and $L^2$ are chloro, the iron complex useful in any of the processes described herein is of the Formula (A-III):

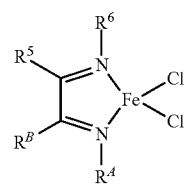

(A-III)

wherein $R^A$, $R^B$, $R^5$, and $R^6$ are as defined herein.

In certain embodiments, wherein $L^1$ and $L^2$ are chloro, the iron complex useful in any of the processes described herein is of the Formula (B-III):

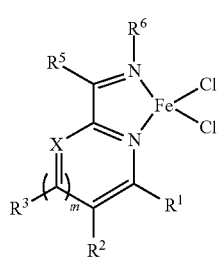

(B-III)

wherein X, m, $R^1$, $R^2$, $R^3$, $R^5$, and $R^6$ are as defined herein.

In certain embodiments, wherein $L^1$ and $L^2$ are chloro, the iron complex useful in any of the processes described herein is of the Formula (E-III):

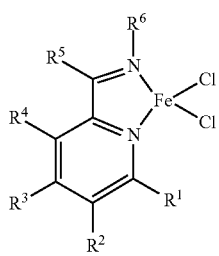

(E-III)

wherein $R^1$, $R^2$, $R^3$, $R^4$, $R^5$, and $R^6$ are as defined herein.

In other embodiments, $L^1$ and $L^2$ are a bidentate ligand.

In certain embodiments, wherein $L^1$ and $L^2$ are a bidentate ligand, $L^1$ and $L^2$ are each independently selected from —$NH_2$, monosubstituted amino, disubstituted amino, phosphino, silyl, boronyl, —OH, —CN, optionally substituted alkyl, optionally substituted alkenyl, optionally substituted alkynyl, optionally substituted carbocyclyl, optionally substituted heterocyclyl, optionally substituted aryl, and optionally substituted heteroaryl, wherein $L^1$ and $L^2$ are joined by a bond, a divalent group selected from divalent alkyl, divalent alkenyl, divalent alkynyl, divalent carbocyclyl, divalent heterocyclyl, divalent aryl, divalent heteroaryl, or a combination thereof.

In certain embodiments, wherein $L^1$ and $L^2$ are a bidentate ligand, $L^1$ and $L^2$ are each independently selected from —$NH_2$, monosubstituted amino, and disubstituted amino, wherein $L^1$ and $L^2$ are joined by a divalent group selected from divalent alkyl, divalent alkenyl, divalent alkynyl, divalent carbocyclyl, divalent heterocyclyl, divalent aryl, and divalent heteroaryl, or a combination thereof. In certain embodiments, wherein $L^1$ and $L^2$ comprise a bidentate ligand, $L^1$ and $L^2$ are each independently selected from —$NH_2$ wherein $L^1$ and $L^2$ are joined by a divalent group selected from divalent alkyl, divalent alkenyl, divalent alkynyl, divalent carbocyclyl, divalent heterocyclyl, divalent aryl, and divalent heteroaryl, or a combination thereof. In certain embodiments, $L^1$ and $L^2$ are each independently selected from —$NH_2$ wherein $L^1$ and $L^2$ are joined by a divalent alkyl group. In certain embodiments, $L^1$ and $L^2$ are joined to form ethylenediamine (en, $H_2N$—$CH_2CH_2$—$NH_2$).

In certain embodiments, wherein $L^1$ and $L^2$ comprise a bidentate ligand, $L^1$ and $L^2$ are each independently selected from optionally substituted aryl and optionally substituted heteroaryl, wherein $L^1$ and $L^2$ are joined by a bond, a divalent group selected from divalent alkyl, divalent alkenyl, divalent alkynyl, divalent carbocyclyl, divalent heterocyclyl, divalent aryl, divalent heteroaryl, or a combination thereof. In certain embodiments, $L^1$ and $L^2$ are each independently optionally substituted heteroaryl groups wherein $L^1$ and $L^2$ are joined by a bond, a divalent alkenyl, or a combination thereof. In certain embodiments, $L^1$ and $L^2$ are each independently optionally substituted pyridinyl groups wherein $L^1$ and $L^2$ are joined by a bond, a divalent alkenyl, or a combination thereof. In certain embodiments, $L^1$ and $L^2$ are each independently optionally substituted pyridinyl groups wherein $L^1$ and $L^2$ are joined by a bond (e.g., 2,2'-bipyridinyl, bipy). In certain embodiments, $L^1$ and $L^2$ are each independently optionally substituted pyridinyl groups wherein $L^1$ and $L^2$ are joined by a bond and a divalent alkenyl group (e.g., 1,10-phenanthrolinyl, phen).

In certain embodiments, wherein $L^1$ and $L^2$ comprise a bidentate ligand, $L^1$ is selected from $NH_2$, monosubstituted amino, and disubstituted amino, and $L^2$ is selected from optionally substituted aryl and optionally substituted heteroaryl, wherein $L^1$ and $L^2$ are joined by a bond, a divalent group selected from divalent alkyl, divalent alkenyl, divalent alkynyl, divalent carbocyclyl, divalent heterocyclyl, divalent aryl, divalent heteroaryl, or a combination thereof.

For example, in certain embodiments wherein $L^1$ and $L^2$ comprise a bidentate ligand, the iron complex is of the Formula (B-IV):

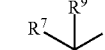

(B-IV)

wherein X, m, $R^1$, $R^2$, $R^3$, $R^4$, $R^5$, and $R^6$ are as defined herein;

each instance of $R^{30}$ and $R^{31}$ are independently selected from hydrogen and optionally substituted alkyl; and each instance of $R^{32}$, $R^{33}$, $R^{34}$, and $R^{35}$ is independently selected from the group consisting of hydrogen, halogen, —CN, —$NO_2$, —$N_3$, —$SO_2H$, —$SO_3H$, —OH, —SH, —$NH_2$, substituted hydroxyl, substituted thiol, monosubstituted amino, disubstituted amino, trisubstituted amino, sulfonyl, sulfinyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl.

In certain embodiments, $R^{30}$ and $R^{31}$ are independently optionally substituted alkyl. In certain embodiments, $R^{30}$ and $R^{31}$ are independently optionally substituted $C_{1-6}$ alkyl. In certain embodiments, $R^{30}$ and $R^{31}$ are independently optionally substituted $C_{1-4}$ alkyl. In certain embodiments, $R^{30}$ and $R^{31}$ are independently optionally substituted $C_{1-3}$ alkyl. In certain embodiments, $R^{30}$ and $R^{31}$ are independently selected from —$CH_2CH_2CH_3$ (-nPr), —$CH_2CH_3$ (-Et), or —$CH_3$ (-Me). In certain embodiments, both $R^{30}$ and $R^{31}$ are —$CH_3$.

In certain embodiments, each instance of $R^{32}$, $R^{33}$, $R^{34}$ and $R^{35}$ is independently selected from the group consisting of hydrogen and optionally substituted alkyl. In certain embodiments, each instance of $R^{32}$, $R^{33}$, $R^{34}$ and $R^{35}$ is hydrogen.

In certain embodiments, wherein $R^6$ is substituted alkyl, the resulting metal complex provided comprises iron and a ligand of the (BI-a):

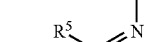

(BI-a)

wherein $R^7$, $R^8$, and $R^9$ are each independently selected from the group consisting of hydrogen, halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, or $R^7$ and $R^8$ are joined to form optionally substituted carbocyclyl or heterocylyl ring.

In certain embodiments, the metal complex of Formula (BI-a) is of the Formula (BII-a):

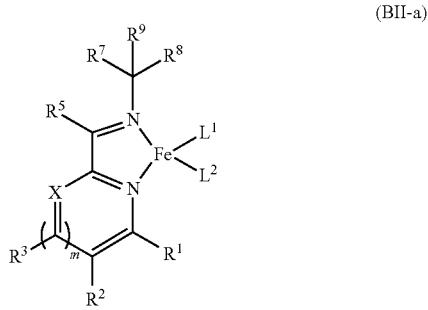

(BII-a)

wherein X, m, $R^1$, $R^2$, $R^3$, $R^4$, $R^5$, $R^7$, $R^8$, $R^9$, $L^1$ and $L^2$ as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are —OAc.

In certain embodiments, $R^7$ is selected from hydrogen, optionally substituted alkyl, optionally substituted alkenyl, optionally substituted aryl, or optionally substituted heteroaryl. In certain embodiments, $R^7$ is hydrogen. In certain embodiments, $R^7$ is optionally substituted $C_{1-12}$ alkyl. In certain embodiments, $R^7$ is optionally substituted $C_{1-10}$ alkyl. In certain embodiments, $R^7$ is optionally substituted $C_{1-9}$ alkyl. In certain embodiments, $R^7$ is optionally substituted $C_{1-8}$ alkyl. In certain embodiments, $R^7$ is optionally substituted $C_{1-7}$ alkyl. In certain embodiments, $R^7$ is optionally substituted $C_{1-6}$ alkyl. In certain embodiments, $R^7$ is optionally substituted $C_{1-5}$ alkyl. In certain embodiments, $R^7$ is optionally substituted $C_{1-4}$ alkyl. In certain embodiments, $R^7$ is optionally substituted $C_{1-3}$ alkyl. In certain embodiments, $R^7$ is optionally substituted $C_{1-2}$ alkyl. In certain embodiments, $R^7$ is —CH$_2$C(CH$_3$)$_3$. In certain embodiments, $R^7$ is —CH$_2$C(CH$_2$CH$_3$)$_3$. In certain embodiments, $R^7$ is —C(CH$_3$)$_3$ (-tBu). In certain embodiments, $R^7$ is —CH(CH$_3$)$_2$ (-iPr). In certain embodiments, $R^7$ is —CH$_2$CH(CH$_3$)$_2$. In certain embodiments, $R^7$ is —CH$_2$CH$_2$CH$_3$ (-nPr). In certain embodiments, $R^7$ is —CH$_2$CH$_3$ (-Et). In certain embodiments, $R^7$ is —CH$_3$ (-Me). In certain embodiments, $R^7$ is —CF$_3$. In certain embodiments, $R^7$ is —CH$_2$Si(CH$_3$)$_3$. In certain embodiments, $R^7$ is optionally substituted aralkyl (e.g., —CH$_2$-aryl, e.g., —CH$_2$Ph). In certain embodiments, $R^7$ is optionally substituted $C_{2-6}$ alkenyl, e.g., —CH=CH$_2$, —CH$_2$CH=CH$_2$.

In certain embodiments, $R^8$ is selected from hydrogen, optionally substituted alkyl, optionally substituted alkenyl, optionally substituted aryl, or optionally substituted heteroaryl. In certain embodiments, $R^8$ is hydrogen. In certain embodiments, $R^8$ is optionally substituted $C_{1-12}$ alkyl. In certain embodiments, $R^8$ is optionally substituted $C_{1-10}$ alkyl. In certain embodiments, $R^8$ is optionally substituted $C_{1-9}$ alkyl. In certain embodiments, $R^7$ is optionally substituted $C_{1-8}$ alkyl. In certain embodiments, $R^8$ is optionally substituted $C_{1-7}$ alkyl. In certain embodiments, $R^8$ is optionally substituted $C_{1-6}$ alkyl. In certain embodiments, $R^8$ is optionally substituted $C_{1-5}$ alkyl. In certain embodiments, $R^8$ is optionally substituted $C_{1-4}$ alkyl. In certain embodiments, $R^8$ is optionally substituted $C_{1-3}$ alkyl. In certain embodiments, $R^8$ is optionally substituted $C_{1-2}$ alkyl. In certain embodiments, $R^8$ is —CH$_2$C(CH$_3$)$_3$. In certain embodiments, $R^8$ is —CH$_2$C(CH$_2$CH$_3$)$_3$. In certain embodiments, $R^8$ is —C(CH$_3$)$_3$ (-tBu). In certain embodiments, $R^8$ is —CH(CH$_3$)$_2$ (-iPr). In certain embodiments, $R^8$ is —CH$_2$CH(CH$_3$)$_2$. In certain embodiments, $R^8$ is —CH$_2$CH$_2$CH$_3$ (-nPr). In certain embodiments, $R^8$ is —CH$_2$CH$_3$ (-Et). In certain embodiments, $R^8$ is —CH$_3$ (-Me). In certain embodiments, $R^8$ is —CF$_3$. In certain embodiments, $R^8$ is —CH$_2$Si(CH$_3$)$_3$. In certain embodiments, $R^8$ is optionally substituted aralkyl (e.g., —CH$_2$-aryl, e.g., —CH$_2$Ph). In certain embodiments, $R^8$ is optionally substituted $C_{2-6}$ alkenyl, e.g., —CH=CH$_2$, —CH$_2$CH=CH$_2$.

In certain embodiments, $R^9$ is selected from hydrogen, optionally substituted alkyl, optionally substituted alkenyl, optionally substituted aryl, or optionally substituted heteroaryl. In certain embodiments, $R^9$ is hydrogen. In certain embodiments, $R^9$ is optionally substituted $C_{1-12}$ alkyl. In certain embodiments, $R^9$ is optionally substituted $C_{1-10}$ alkyl. In certain embodiments, $R^9$ is optionally substituted $C_{1-9}$ alkyl. In certain embodiments, $R^9$ is optionally substituted $C_{1-8}$ alkyl. In certain embodiments, $R^9$ is optionally substituted $C_{1-7}$ alkyl. In certain embodiments, $R^9$ is optionally substituted $C_{1-6}$ alkyl. In certain embodiments, $R^9$ is optionally substituted $C_{1-5}$ alkyl. In certain embodiments, $R^9$ is optionally substituted $C_{1-4}$ alkyl. In certain embodiments, $R^9$ is optionally substituted $C_{1-3}$ alkyl. In certain embodiments, $R^9$ is optionally substituted $C_{1-2}$ alkyl. In certain embodiments, $R^9$ is —CH$_2$C(CH$_3$)$_3$. In certain embodiments, $R^9$ is —CH$_2$C(CH$_2$CH$_3$)$_3$. In certain embodiments, $R^9$ is —C(CH$_3$)$_3$ (-tBu). In certain embodiments, $R^9$ is —CH(CH$_3$)$_2$ (-iPr). In certain embodiments, $R^9$ is —CH$_2$CH(CH$_3$)$_2$. In certain embodiments, $R^9$ is —CH$_2$CH$_2$CH$_3$ (-nPr). In certain embodiments, $R^9$ is —CH$_2$CH$_3$ (-Et). In certain embodiments, $R^9$ is —CH$_3$ (-Me). In certain embodiments, $R^9$ is —CF$_3$. In certain embodiments, $R^9$ is —CH$_2$Si(CH$_3$)$_3$. In certain embodiments, $R^9$ is optionally substituted aralkyl (e.g., —CH$_2$-aryl, e.g., —CH$_2$Ph). In certain embodiments, $R^9$ is optionally substituted $C_{2-6}$ alkenyl, e.g., —CH=CH$_2$, —CH$_2$CH=CH$_2$.

In certain embodiments, $R^7$ and $R^8$ are each independently selected from the group consisting of hydrogen, halogen, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, and $R^9$ is selected from hydrogen or optionally substituted alkyl. In certain embodiments, each instance of $R^7$ and $R^8$ is independently optionally substituted alkyl. In certain embodiments, each instance of $R^8$ and $R^9$ is independently optionally substituted alkyl. In certain embodiments, each instance of $R^7$ and $R^8$ is independently optionally substituted alkyl and $R^9$ is hydrogen. In certain embodiments, each instance of $R^7$ and $R^8$ is independently optionally substituted alkyl and $R^9$ is optionally substituted alkyl.

In certain embodiments, $R^7$ and $R^8$ are joined to form optionally substituted carbocyclyl ring, e.g., optionally substituted cyclopropyl, optionally substituted cyclobutyl, optionally substituted cyclopentyl, or optionally substituted cyclohexyl ring. In certain embodiments, $R^7$ and $R^8$ are joined to form optionally substituted heterocyclyl ring.

In certain embodiments, $R^7$ is optionally substituted aryl, e.g., optionally substituted phenyl, optionally substituted napthyl. In certain embodiments, $R^7$ is optionally substituted phenyl. In certain embodiments, $R^7$ is optionally substituted aryl, $R^8$ is selected from hydrogen, halogen, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, optionally substituted heteroaryl; and $R^9$ is selected from hydrogen or optionally substituted alkyl. In certain embodiments, $R^7$ is optionally substituted aryl, $R^8$ is optionally substituted aryl, and $R^9$ is hydrogen.

In certain embodiments, wherein $R^7$ is optionally substituted aryl, the resulting metal complex provided comprises iron and a ligand of the Formula (BI-b):

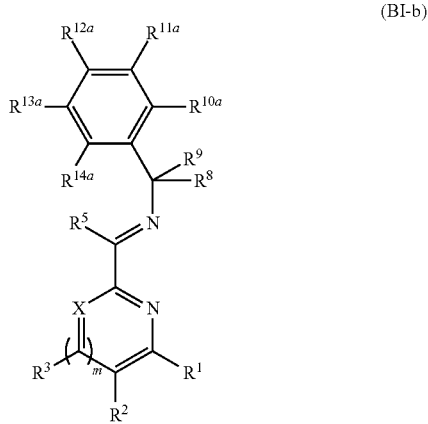

(BI-b)

wherein $R^8$ and $R^9$ are as defined herein, and each instance of $R^{10a}$, $R^{11a}$, $R^{12a}$, $R^{13a}$, and $R^{14a}$ is independently selected from the group consisting of hydrogen, halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl.

In certain embodiments, the metal complex of Formula (BI-b) is of the Formula (BII-b):

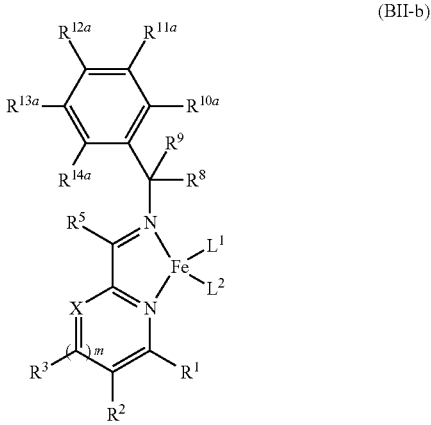

(BII-b)

wherein X, m, $R^1$, $R^2$, $R^3$, $R^4$, $R^5$, $R^8$, $R^9$, $R^{10a}$, $R^{11a}$, $R^{12a}$, $R^{13a}$, $R^{14a}$, $R^8$, $R^9$, $L^1$ and $L^2$ are as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are —OAc.

In certain embodiments, $R^{10a}$ is selected from the group consisting of hydrogen, halogen, substituted hydroxyl, optionally substituted alkyl, or optionally substituted aryl. In certain embodiments, $R^{10a}$ is hydrogen. In certain embodiments, $R^{10a}$ is substituted hydroxyl, e.g., —OCH$_3$. In certain embodiments, $R^{10a}$ is halogen, e.g., —F, —Br, —I, or —Cl. In certain embodiments, $R^{10a}$ is optionally substituted alkyl. In certain embodiments, $R^{10a}$ is optionally substituted $C_{1-6}$ alkyl. In certain embodiments, $R^{10a}$ is selected optionally substituted $C_{1-4}$ alkyl. In certain embodiments, $R^{10a}$ is optionally substituted $C_{1-3}$ alkyl. In certain embodiments, $R^{10a}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), —CF$_3$, and —CH$_2$Si(CH$_3$)$_3$.

In certain embodiments, $R^{11a}$ is selected from the group consisting of hydrogen, halogen, substituted hydroxyl, optionally substituted alkyl, or optionally substituted aryl. In certain embodiments, $R^{11a}$ is hydrogen. In certain embodiments, $R^{11a}$ is substituted hydroxyl, e.g., —OCH$_3$. In certain embodiments, $R^{11a}$ is halogen, e.g., —F, —Br, —I, or —Cl. In certain embodiments, $R^{11a}$ is optionally substituted alkyl. In certain embodiments, $R^{11a}$ is optionally substituted $C_{1-6}$ alkyl. In certain embodiments, $R^{11a}$ is optionally substituted $C_{1-4}$ alkyl. In certain embodiments, $R^{11a}$ is optionally substituted $C_{1-3}$ alkyl. In certain embodiments, $R^{11a}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), —CF$_3$, and —CH$_2$Si(CH$_3$)$_3$.

In certain embodiments, $R^{12a}$ is selected from the group consisting of hydrogen, halogen, substituted hydroxyl, optionally substituted alkyl, or optionally substituted aryl. In certain embodiments, $R^{12a}$ is hydrogen. In certain embodiments, $R^{12a}$ is substituted hydroxyl, e.g., —OCH$_3$. In certain embodiments, $R^{12a}$ is halogen, e.g., —F, —Br, —I, or —Cl. In certain embodiments, $R^{12a}$ is optionally substituted alkyl. In certain embodiments, $R^{12a}$ is optionally substituted $C_{1-6}$ alkyl. In certain embodiments, $R^{12a}$ is optionally substituted $C_{1-4}$ alkyl. In certain embodiments, $R^{12a}$ is optionally substituted $C_{1-3}$ alkyl. In certain embodiments, $R^{12a}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), —CF$_3$, and —CH$_2$Si(CH$_3$)$_3$.

In certain embodiments, $R^{13a}$ is selected from the group consisting of hydrogen, halogen, substituted hydroxyl, optionally substituted alkyl, or optionally substituted aryl. In certain embodiments, $R^{13a}$ is hydrogen. In certain embodiments, $R^{13a}$ is substituted hydroxyl, e.g., —OCH$_3$. In certain embodiments, $R^{13a}$ is halogen, e.g., —F, —Br, —I, or —Cl. In certain embodiments, $R^{13a}$ is optionally substituted alkyl. In certain embodiments, $R^{13a}$ is optionally substituted $C_{1-6}$ alkyl. In certain embodiments, $R^{13a}$ is optionally substituted $C_{1-4}$ alkyl. In certain embodiments, $R^{13a}$ is optionally substituted $C_{1-3}$ alkyl. In certain embodiments, $R^{13a}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), —CF$_3$, and —CH$_2$Si(CH$_3$)$_3$.

In certain embodiments, $R^{14a}$ is selected from the group consisting of hydrogen, halogen, substituted hydroxyl, optionally substituted alkyl, or optionally substituted aryl. In certain embodiments, $R^{14a}$ is hydrogen. In certain embodiments, $R^{14a}$ is substituted hydroxyl, e.g., —OCH$_3$. In certain embodiments, $R^{14a}$ is halogen, e.g., —F, —Br, —I, or —Cl. In certain embodiments, $R^{14a}$ is optionally substituted alkyl. In certain embodiments, $R^{14a}$ is optionally substituted $C_{1-6}$ alkyl. In certain embodiments, $R^{14a}$ is optionally substituted $C_{1-4}$ alkyl. In certain embodiments, $R^{14a}$ is optionally substituted $C_{1-3}$ alkyl. In certain embodiments, $R^{14a}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), —CF$_3$, and —CH$_2$Si(CH$_3$)$_3$.

In certain embodiments, $R^7$ is mono-substituted phenyl. Exemplary ligands, wherein $R^7$ is mono-substituted phenyl, m is 1 and X is C—$R^4$, include those of the Formula (EI-b1), (EI-b2), and (EI-b3):

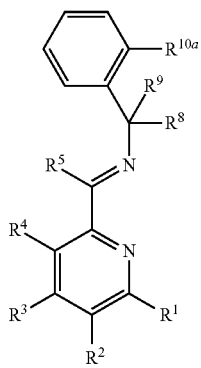

(EI-b1)

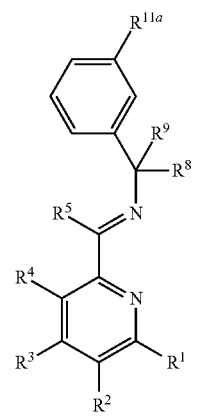

(EI-b2)

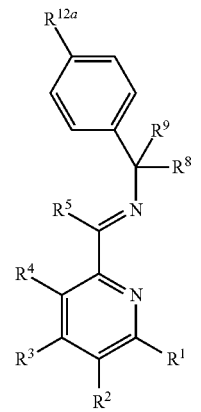

(EI-b3)

wherein $R^1$, $R^2$, $R^3$, $R^4$, $R^5$, $R^8$ and $R^9$ are as defined herein; and each instance of $R^{10a}$, $R^{11a}$, and $R^{12a}$ is independently selected from halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl.

In certain embodiments, $R^7$ is disubstituted phenyl. Exemplary ligands, wherein $R^7$ is disubstituted phenyl, m is 1 and X is C—$R^4$, include those of the Formula (EI-b4), (EI-b5), (EI-b6), (EI-b7), (EI-b8), and (EI-b9):

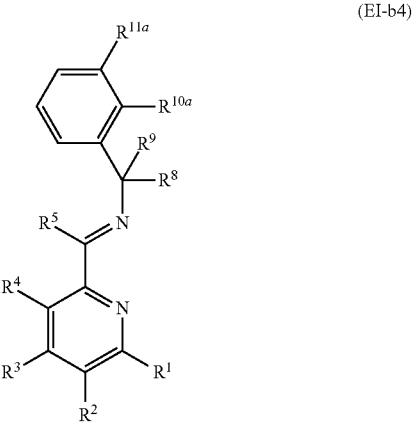

(EI-b4)

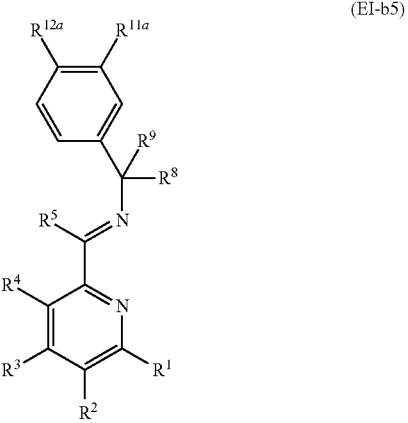

(EI-b5)

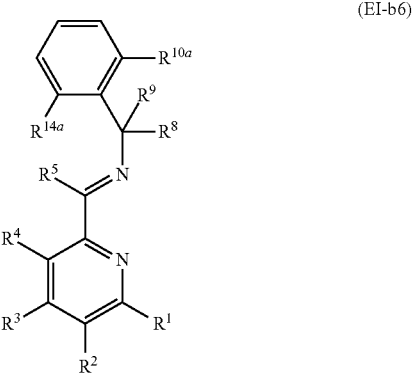

(EI-b6)

-continued

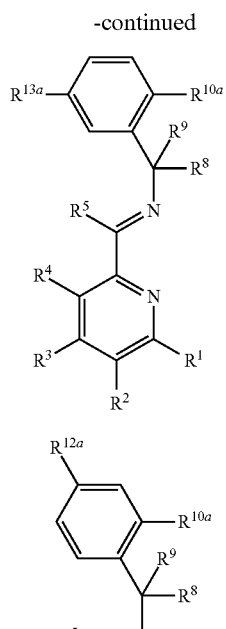

(EI-b7)

(EI-b8)

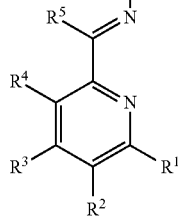

(EI-b9)

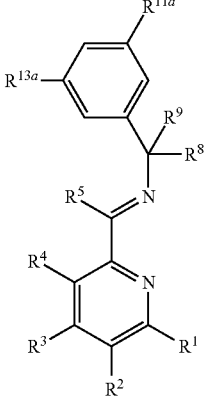

wherein $R^1$, $R^2$, $R^3$, $R^4$, $R^5$, $R^8$ and $R^9$ are as defined herein; and each instance of $R^{10a}$, $R^{11a}$, $R^{12a}$, $R^{13a}$, and $R^{14a}$ is independently selected from halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl.

In certain embodiments, $R^8$ is optionally substituted aryl, e.g., optionally substituted phenyl, optionally substituted napthyl. In certain embodiments, $R^8$ is optionally substituted phenyl. In certain embodiments, $R^7$ and $R^8$ are each independently optionally substituted phenyl. In certain embodiments, $R^7$ and $R^8$ are each independently optionally substituted phenyl; and $R^9$ is selected from hydrogen or optionally substituted alkyl. In certain embodiments, $R^9$ is hydrogen.

For example, in certain embodiments, wherein $R^7$ and $R^8$ are each independently optionally substituted phenyl, the resulting metal complex provided comprises iron and a ligand of the Formula (B-Ic):

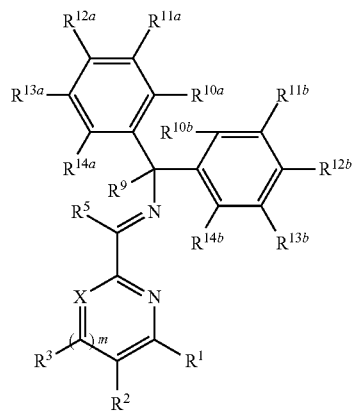

(BI-c)

wherein:
each instance of $R^{10b}$, $R^{11b}$, $R^{12b}$, $R^{13b}$, and $R^{14b}$ is independently selected from the group consisting of hydrogen, halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; and
$R^9$ is hydrogen or optionally substituted alkyl.

In certain embodiments, the metal complex of Formula (BI-c) is of the Formula (BII-c):

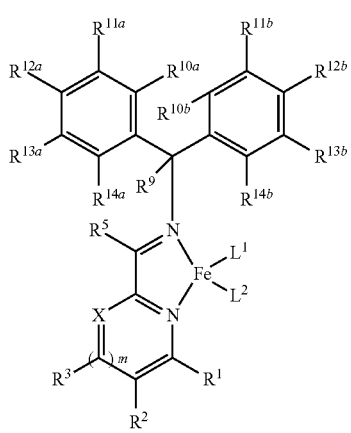

(BII-c)

wherein X, m, $R^1$, $R^2$, $R^3$, $R^4$, $R^5$, $R^9$, $R^{10a}$, $R^{11a}$, $R^{12a}$, $R^{13a}$, $R^{14a}$, $R^{10b}$, $R^{11b}$, $R^{12b}$, $R^{13b}$, $R^{14b}$, $L^1$, and $L^2$ as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are —OAc.

In certain embodiments, $R^{10b}$ is selected from the group consisting of hydrogen, halogen, substituted hydroxyl, optionally substituted alkyl, or optionally substituted aryl. In certain embodiments, $R^{10b}$ is hydrogen. In certain embodiments, $R^{10b}$ is substituted hydroxyl, e.g., —OCH$_3$. In certain embodiments, $R^{10b}$ is halogen, e.g., —F, —Br, —I, or —Cl. In certain embodiments, $R^{10b}$ is optionally substituted alkyl. In certain embodiments, $R^{10b}$ is optionally substituted $C_{1-6}$ alkyl. In certain embodiments, $R^{10b}$ is optionally substituted $C_{1-4}$ alkyl. In certain embodiments, $R^{10b}$ is optionally substituted $C_{1-3}$ alkyl. In certain embodiments, $R^{10b}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), CF$_3$, and —CH$_2$Si(CH$_3$)$_3$.

In certain embodiments, $R^{11b}$ is selected from the group consisting of hydrogen, halogen, substituted hydroxyl, optionally substituted alkyl, or optionally substituted aryl. In certain embodiments, $R^{11b}$ is hydrogen. In certain embodiments, $R^{11b}$ is substituted hydroxyl, e.g., —OCH$_3$. In certain embodiments, $R^{11b}$ is halogen, e.g., —F, —Br, —I, or —Cl. In certain embodiments, $R^{11b}$ is optionally substituted alkyl. In certain embodiments, $R^{11b}$ is optionally substituted $C_{1-6}$ alkyl. In certain embodiments, $R^{11b}$ is optionally substituted $C_{1-4}$ alkyl. In certain embodiments, $R^{11b}$ is optionally substituted $C_{1-3}$ alkyl. In certain embodiments, $R^{11b}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), CF$_3$, and —CH$_2$Si(CH$_3$)$_3$.

In certain embodiments, $R^{12b}$ is selected from the group consisting of hydrogen, halogen, substituted hydroxyl, optionally substituted alkyl, or optionally substituted aryl. In certain embodiments, $R^{12b}$ is hydrogen. In certain embodiments, $R^{12b}$ is substituted hydroxyl, e.g., —OCH$_3$. In certain embodiments, $R^{12b}$ is halogen, e.g., —F, —Br, —I, or —Cl. In certain embodiments, $R^{12b}$ is optionally substituted alkyl. In certain embodiments, $R^{12b}$ is optionally substituted $C_{1-6}$ alkyl. In certain embodiments, $R^{12b}$ is optionally substituted $C_{1-4}$ alkyl. In certain embodiments, $R^{12b}$ is optionally substituted $C_{1-3}$ alkyl. In certain embodiments, $R^{12b}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), —CF$_3$, and —CH$_2$Si(CH$_3$)$_3$.

In certain embodiments, $R^{13b}$ is selected from the group consisting of hydrogen, halogen, substituted hydroxyl, optionally substituted alkyl, or optionally substituted aryl. In certain embodiments, $R^{13b}$ is hydrogen. In certain embodiments, $R^{13b}$ is substituted hydroxyl, e.g., —OCH$_3$. In certain embodiments, $R^{13b}$ is halogen, e.g., —F, —Br, —I, or —Cl. In certain embodiments, $R^{13b}$ is optionally substituted alkyl. In certain embodiments, $R^{13b}$ is optionally substituted $C_{1-6}$ alkyl. In certain embodiments, $R^{13b}$ is optionally substituted $C_{1-4}$ alkyl. In certain embodiments, $R^{13b}$ is optionally substituted $C_{1-3}$ alkyl. In certain embodiments, $R^{13b}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), —CF$_3$, and —CH$_2$Si(CH$_3$)$_3$.

In certain embodiments, $R^{14b}$ is selected from the group consisting of hydrogen, halogen, substituted hydroxyl, optionally substituted alkyl, or optionally substituted aryl. In certain embodiments, $R^{14b}$ is hydrogen. In certain embodiments, $R^{14b}$ is substituted hydroxyl, e.g., —OCH$_3$. In certain embodiments, $R^{14b}$ is halogen, e.g., —F, —Br, —I, or —Cl. In certain embodiments, $R^{14b}$ is optionally substituted alkyl. In certain embodiments, $R^{14b}$ is optionally substituted $C_{1-6}$ alkyl. In certain embodiments, $R^{14b}$ is optionally substituted $C_{1-4}$ alkyl. In certain embodiments, $R^{14b}$ is optionally substituted $C_{1-3}$ alkyl. In certain embodiments, $R^{14b}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), —CF$_3$, and —CH$_2$Si(CH$_3$)$_3$.

In certain embodiments, both $R^7$ and $R^8$ are independently mono-substituted phenyl. Exemplary ligands, wherein both $R^7$ and $R^8$ are independently mono-substituted phenyl, m is 1 and X is C—$R^4$, include those of the Formula (EI-c1), (EI-c2), (EI-c3), (EI-c4), (EI-c5), and (EI-c6):

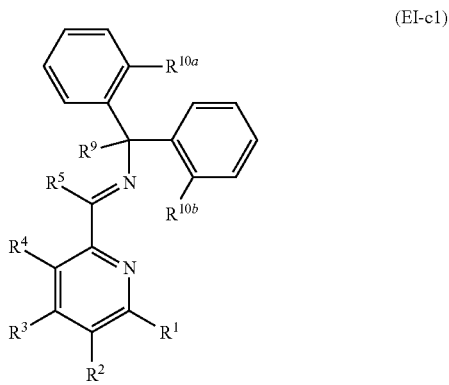

(EI-c1)

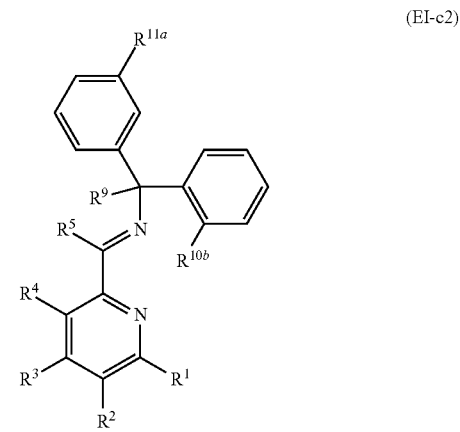

(EI-c2)

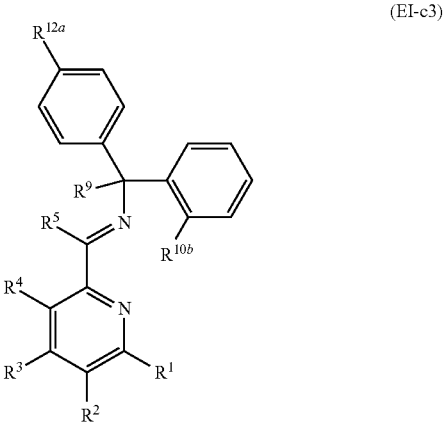

(EI-c3)

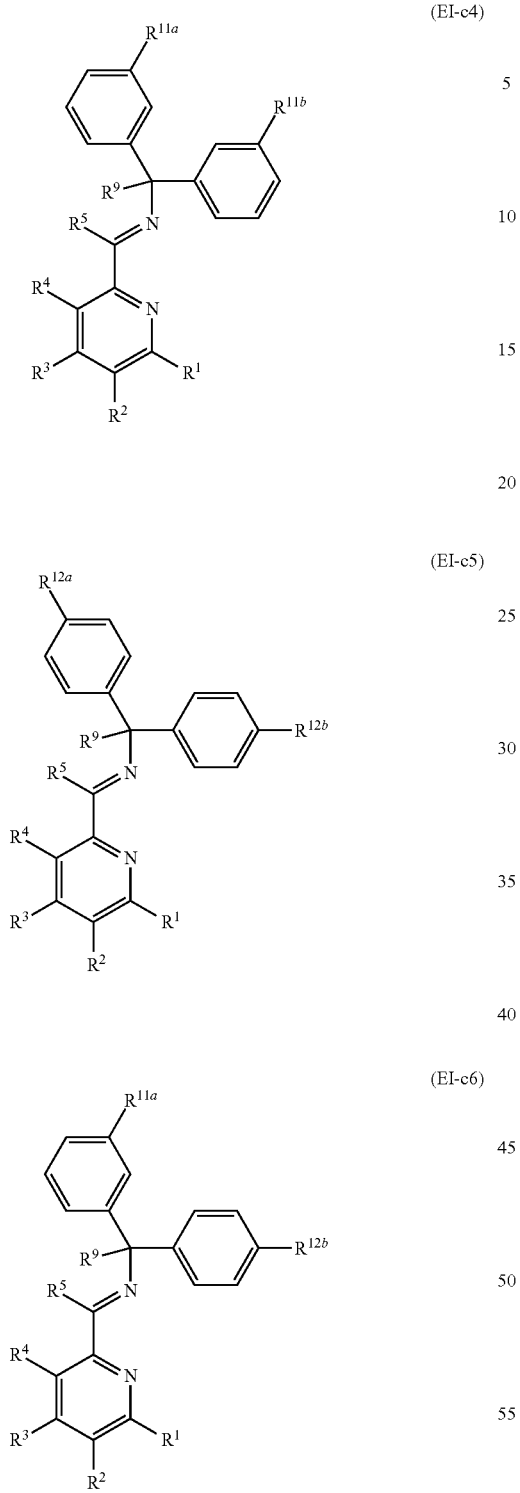

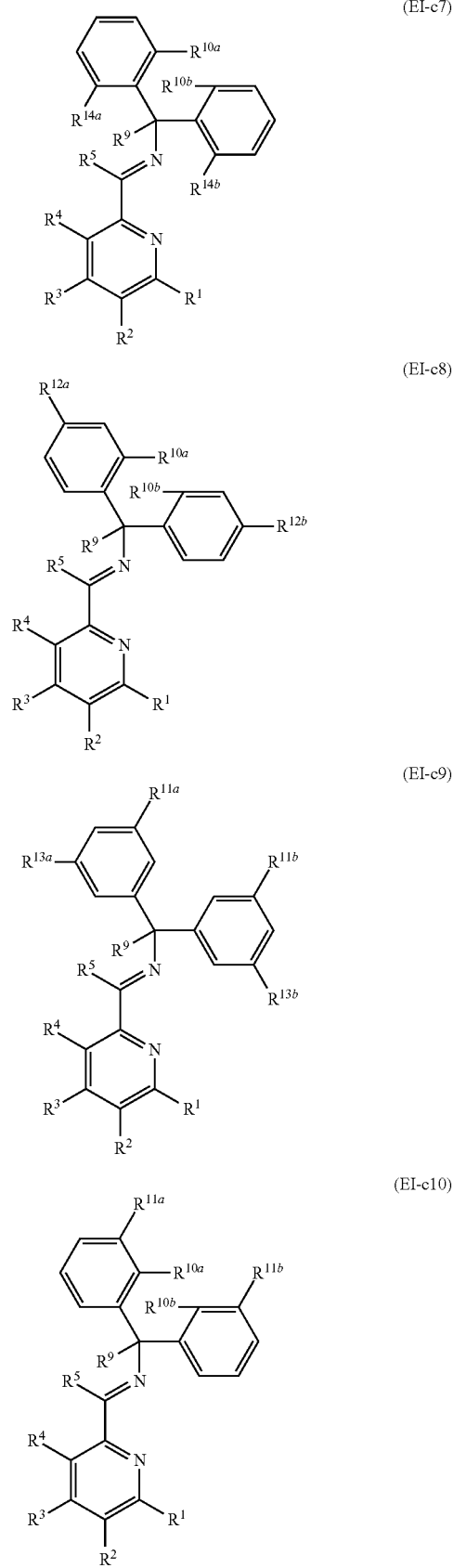

wherein $R^1$, $R^2$, $R^3$, $R^4$, $R^5$, $R^{10a}$, $R^{11a}$, $R^{12a}$, $R^{13a}$, $R^{14a}$, $R^{10b}$, $R^{11b}$, $R^{12b}$, $R^{13b}$, and $R^{14b}$ are as defined herein.

In certain embodiments, both $R^7$ and $R^8$ are independently disubstituted phenyl. Exemplary ligands, wherein both $R^7$ and $R^8$ are independently disubstituted phenyl, m is 1 and X is C—$R^4$, includes those of the Formula (EI-c7), (EI-c8), (EI-c9), (EI-c10), (EI-c11), and (EI-c12):

-continued (EI-c11)

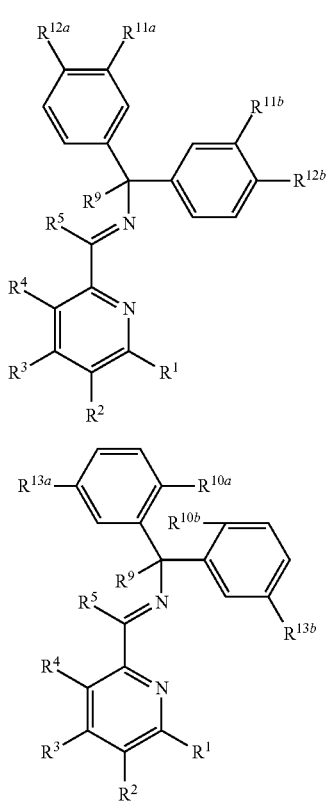

(EI-c12)

wherein $R^1$, $R^2$, $R^3$, $R^4$, $R^5$, $R^{10a}$, $R^{11a}$, $R^{12a}$, $R^{13a}$, $R^{14a}$, $R^{10b}$, $R^{11b}$, $R^{12b}$, $R^{13b}$, and $R^{14b}$ are as defined herein.

In certain embodiments, both $R^7$ and $R^8$ are independently trisubstituted phenyl.

In certain embodiments, $R^6$ is optionally substituted aryl or optionally substituted heteroaryl. In certain embodiments, $R^6$ is optionally substituted aryl. In certain embodiments, $R^6$ is optionally substituted phenyl.

For example, in certain embodiments, wherein $R^6$ is optionally substituted phenyl, the resulting metal complex provided comprises iron and a ligand of the Formula (BI-d):

(BI-d)

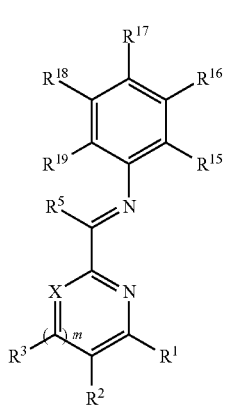

wherein:
each instance of $R^{15}$, $R^{16}$, $R^{17}$, $R^{18}$, and $R^{19}$ is independently selected from the group consisting of hydrogen, halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl.

In certain embodiments, the metal complex of Formula (BI-d) is of the Formula (BII-d):

(BII-d)

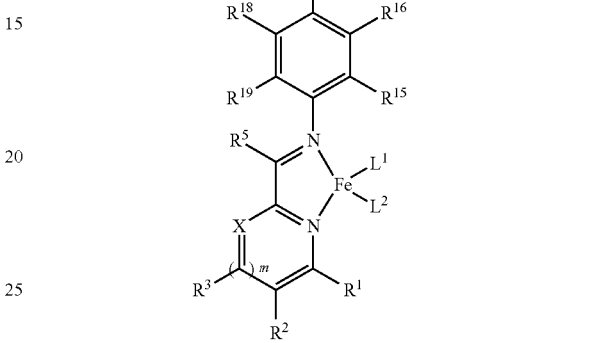

wherein X, m, $R^1$, $R^2$, $R^3$, $R^4$, $R^5$, $R^{15}$, $R^{16}$, $R^{17}$, $R^{18}$, $R^{19}$, $L^1$, and $L^2$ are as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are OAc.

In certain embodiments, $R^{15}$ is selected from the group consisting of hydrogen, halogen, —NO$_2$, substituted amino, optionally substituted alkyl, optionally substituted aryl, and optionally substituted heteroaryl. In certain embodiments, $R^{15}$ is hydrogen. In certain embodiments, $R^{15}$ is halogen, i.e., —F, Br, —I, —Cl. In certain embodiments, $R^{15}$ is —NO$_2$. In certain embodiments, $R^{15}$ is substituted amino, e.g., —NMe$_2$. In certain embodiments, $R^{15}$ is optionally substituted aryl, e.g., optionally substituted phenyl, optionally substituted naphthyl. In certain embodiments, $R^{15}$ is optionally substituted heteroaryl, e.g., optionally substituted pyridinyl. In certain embodiments, $R^{15}$ is optionally substituted alkyl. In certain embodiments, $R^{15}$ is optionally substituted $C_{1-6}$ alkyl. In certain embodiments, $R^{15}$ is optionally substituted $C_{1-4}$ alkyl. In certain embodiments, $R^{15}$ is optionally substituted $C_{1-3}$ alkyl. In certain embodiments, $R^{15}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), —CF$_3$, and —CH$_2$Si(CH$_3$)$_3$. In certain embodiments, $R^{15}$ is phenyl.

In certain embodiments, $R^{16}$ is selected from the group consisting of hydrogen, halogen, —NO$_2$, substituted amino, optionally substituted alkyl, optionally substituted aryl, and optionally substituted heteroaryl. In certain embodiments, $R^{16}$ is hydrogen. In certain embodiments, $R^{16}$ is halogen, i.e., —F, Br, —I, —Cl. In certain embodiments, $R^{16}$ is —NO$_2$. In certain embodiments, $R^{16}$ is substituted amino, e.g., —NMe$_2$. In certain embodiments, $R^{16}$ is optionally substituted aryl, e.g., optionally substituted phenyl, optionally substituted naphthyl. In certain embodiments, $R^{16}$ is optionally substituted heteroaryl, e.g., optionally substituted pyridinyl. In certain embodiments, $R^{16}$ is optionally substituted alkyl. In certain embodiments, $R^{16}$ is optionally substituted $C_{1-6}$ alkyl. In certain embodiments, $R^{16}$ is optionally substituted $C_{1-4}$ alkyl. In certain embodiments, $R^{16}$ is optionally substituted $C_{1-3}$ alkyl. In certain embodiments, $R^{16}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), —CF$_3$, and —CH$_2$Si(CH$_3$)$_3$.

In certain embodiments, $R^{17}$ is selected from the group consisting of hydrogen, halogen, —NO$_2$, substituted amino, optionally substituted alkyl, optionally substituted aryl, and optionally substituted heteroaryl. In certain embodiments, $R^{17}$ is hydrogen. In certain embodiments, $R^{17}$ is halogen, i.e., —F, Br, —I, —Cl. In certain embodiments, $R^{17}$ is —NO$_2$. In certain embodiments, $R^{17}$ is substituted amino, e.g., —NMe$_2$. In certain embodiments, $R^{17}$ is optionally substituted aryl, e.g., optionally substituted phenyl, optionally substituted naphthyl. In certain embodiments, $R^{17}$ is optionally substituted heteroaryl, e.g., optionally substituted pyridinyl. In certain embodiments, $R^{17}$ is optionally substituted alkyl. In certain embodiments, $R^{17}$ is optionally substituted $C_{1-6}$ alkyl. In certain embodiments, $R^{17}$ is optionally substituted $C_{1-4}$ alkyl. In certain embodiments, $R^{17}$ is optionally substituted $C_{1-3}$ alkyl. In certain embodiments, $R^{17}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), —CF$_3$, and —CH$_2$Si(CH$_3$)$_3$. In certain embodiments, $R^{17}$ is phenyl.

In certain embodiments, $R^{18}$ is selected from the group consisting of hydrogen, halogen, —NO$_2$, substituted amino, optionally substituted alkyl, optionally substituted aryl, and optionally substituted heteroaryl. In certain embodiments, $R^{18}$ is hydrogen. In certain embodiments, $R^{18}$ is halogen, i.e., —F, Br, —I, —Cl. In certain embodiments, $R^{18}$ is NO$_2$. In certain embodiments, $R^{18}$ is substituted amino, e.g., —NMe$_2$. In certain embodiments, $R^{18}$ is optionally substituted aryl, e.g., optionally substituted phenyl, optionally substituted naphthyl. In certain embodiments, $R^{18}$ is optionally substituted heteroaryl, e.g., optionally substituted pyridinyl. In certain embodiments, $R^{18}$ is optionally substituted alkyl. In certain embodiments, $R^{18}$ is optionally substituted $C_{1-6}$ alkyl. In certain embodiments, $R^{18}$ is optionally substituted $C_{1-4}$ alkyl. In certain embodiments, $R^{18}$ is optionally substituted $C_{1-3}$ alkyl. In certain embodiments, $R^{18}$ is selected from the group consisting of hydrogen, —C(CH$_3$)$_3$ (-tBu), —CH(CH$_3$)$_2$CH$_2$CH$_2$CH$_3$ (-nPr), —CH$_2$CH$_3$ (-Et), —CH$_3$ (-Me), —CF$_3$, and —CH$_2$Si(CH$_3$)$_3$.

In certain embodiments, $R^{19}$ is selected from the group consisting of hydrogen, halogen, —NO$_2$, substituted amino, optionally substituted alkyl, optionally substituted aryl, and optionally substituted heteroaryl. In certain embodiments, $R^{19}$ is hydrogen. In certain embodiments, $R^{19}$ is halogen, i.e., —F, Br, —I, —Cl. In certain embodiments, $R^{19}$ is NO$_2$. In certain embodiments, $R^{19}$ is substituted amino, e.g., —NMe$_2$. In certain embodiments, $R^{19}$ is optionally substituted aryl, e.g., optionally substituted phenyl, optionally substituted naphthyl. In certain embodiments, $R^{19}$ is optionally substituted heteroaryl, e.g., optionally substituted pyridinyl. In certain embodiments, $R^{19}$ is optionally substituted alkyl. In certain embodiments, $R^{19}$ is optionally substituted $C_{1-6}$ alkyl. In certain embodiments, $R^{19}$ is optionally substituted $C_{1-4}$ alkyl. In certain embodiments, $R^{19}$ is optionally substituted $C_{1-3}$ alkyl. In certain embodiments, $R^{19}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), —CF$_3$, and —CH$_2$Si(CH$_3$)$_3$.

In certain embodiments, $R^6$ is mono-substituted phenyl. Exemplary ligands, wherein $R^6$ is mono-substituted phenyl, X is C—$R^4$ and m is 1, include those of the Formula (EI-d1), (EI-d2) and (EI-d3):

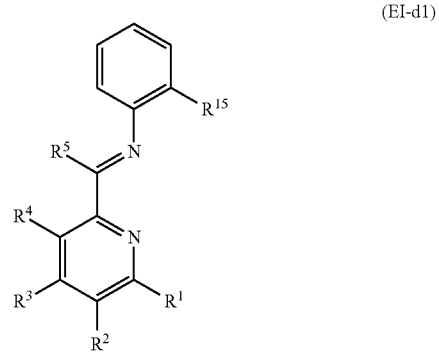

(EI-d1)

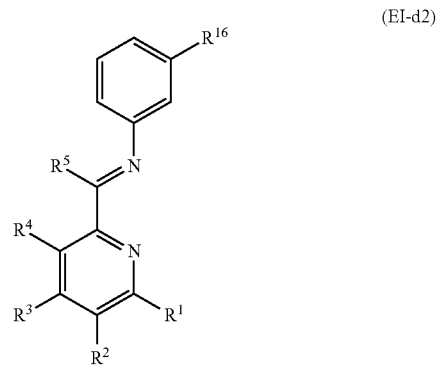

(EI-d2)

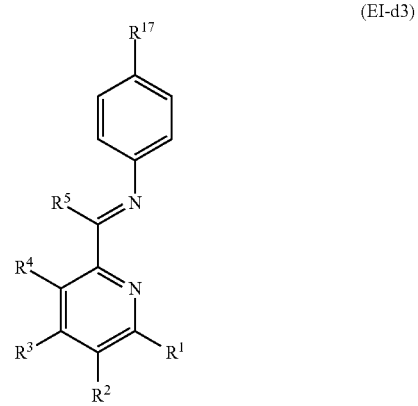

(EI-d3)

wherein $R^1$, $R^2$, $R^3$, $R^4$, $R^5$, $R^{15}$, $R^{16}$, $R^{17}$$R^{18}$, and $R^{19}$ are as defined herein In certain embodiments, $R^6$ is disubstituted phenyl. Exemplary ligands, wherein $R^6$ is disubstituted phenyl, X is C—$R^4$ and m is 1, include those of the Formula (EI-d4), (EI-d5), (EI-d6), (EI-d7), (EI-d8) and (EI-d9):

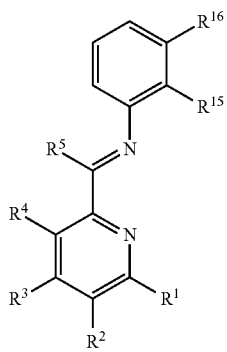
(EI-d4)
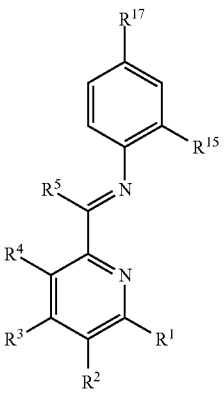
(EI-d8)
(EI-d5)
(EI-d9)
EI-d6)
wherein $R^1$, $R^2$, $R^3$, $R^4$, $R^5$, $R^{15}$, $R^{16}$, $R^{17}$, $R^{18}$, and $R^{19}$ are as defined herein.
In certain embodiments, $R^6$ is trisubstituted phenyl. Exemplary ligands, wherein $R^6$ is trisubstituted phenyl, X is C—$R^4$ and m is 1, include those of the Formula (EI-d10), (EI-d11), (EI-d10), (EI-d11), (EI-d12) and (EI-d13):
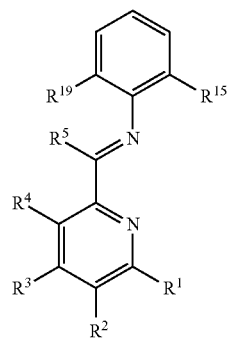
(EI-d7)
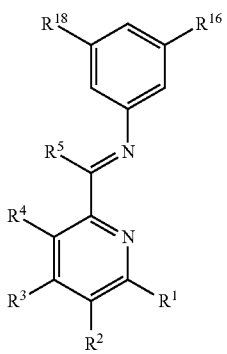
(EI-d10)

-continued

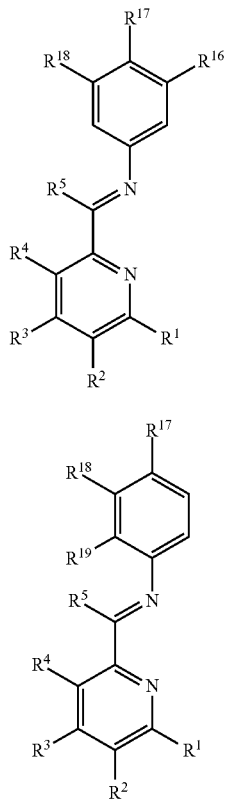

(EI-d11)

(EI-d12)

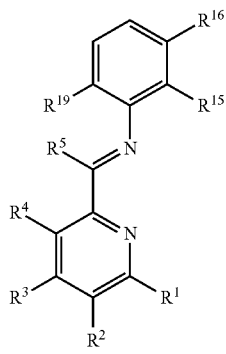

(EI-d13)

wherein $R^1$, $R^2$, $R^3$, $R^4$, $R^5$, $R^{15}$, $R^{16}$, $R^{17}$, $R^{18}$, and $R^{19}$ are as defined herein.

In certain embodiments, $R^5$ and $R^6$ are joined to form an optionally substituted heterocyclyl or optionally substituted heteroaryl ring. In certain embodiments, $R^5$ and $R^6$ are joined to form an optionally substituted heteroaryl ring. In certain embodiments, $R^5$ and $R^6$ are joined to form an optionally substituted 5-6-membered heteroaryl ring. In certain embodiments, $R^5$ and $R^6$ are joined to form an optionally substituted 5-membered heteroaryl ring. Exemplary 5-membered heteroaryl rings include, but are not limited to, isoxazolyl, isothiazolyl, pyrazolyl, oxadiazolyl, thiadiazolyl, and triazolyl. In certain embodiments, $R^5$ and $R^6$ are joined to form an optionally substituted 6-membered heteroaryl ring. Exemplary 6-membered heteroaryl rings include, but are not limited to, pyridinyl, pyridazinyl, pyrimidinyl, pyrazinyl, triazinyl, and tetrazinyl. In certain embodiments, $R^5$ and $R^6$ are joined to form an optionally substituted pyridinyl ring.

For example, in certain embodiments, wherein $R^5$ and $R^6$ are joined to form an optionally substituted pyridinyl ring, the resulting metal complex provided comprises iron and a ligand of the Formula (BI-e):

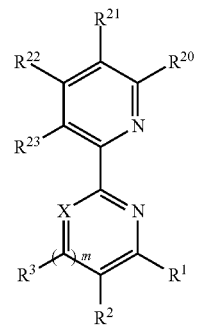

(BI-e)

wherein each instance of $R^{20}$, $R^{21}$, $R^{22}$, and $R^{23}$ is independently selected from the group consisting of hydrogen, halogen, —CN, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl.

In certain embodiments, the metal complex of Formula (BI-e) is of the Formula (BII-e):

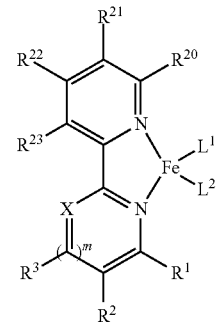

(BII-e)

wherein $R^1$, $R^2$, $R^3$, $R^4$, $R^{20}$, $R^{21}$, $R^{22}$, $R^{23}$, $L^1$ and $L^2$ as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are —OAc.

In certain embodiments, $R^{20}$ is selected from the group consisting of hydrogen, substituted hydroxyl, and optionally substituted alkyl. In certain embodiments, $R^{20}$ is hydrogen. In certain embodiments, $R^{20}$ is substituted hydroxyl, e.g., —OMe. In certain embodiments, $R^{20}$ is optionally substituted alkyl. In certain embodiments, $R^{20}$ is optionally substituted $C_{1-6}$ alkyl. In certain embodiments, $R^{20}$ is optionally substituted $C_{1-4}$ alkyl. In certain embodiments, $R^{20}$ is optionally substituted $C_{1-3}$ alkyl. In certain embodiments, $R^{20}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), and —CH$_2$Si(CH$_3$)$_3$.

In certain embodiments, $R^{21}$ is selected from the group consisting hydrogen, substituted hydroxyl, and optionally substituted alkyl. In certain embodiments, $R^{21}$ is hydrogen. In certain embodiments, $R^{21}$ is substituted hydroxyl, e.g., —OMe. In certain embodiments, $R^{21}$ is optionally substituted alkyl. In certain embodiments, $R^{21}$ is optionally substituted $C_{1-6}$ alkyl. In certain embodiments, $R^{21}$ is optionally substituted $C_{1-4}$ alkyl. In certain embodiments, $R^{21}$ is optionally substituted $C_{1-3}$ alkyl. In certain embodiments, $R^{21}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), and —CH$_2$Si(CH$_3$)$_3$.

In certain embodiments, $R^{22}$ is selected from the group consisting of hydrogen, substituted hydroxyl, and optionally substituted alkyl. In certain embodiments, $R^{22}$ is hydrogen. In certain embodiments, $R^{22}$ is substituted hydroxyl, e.g., —OMe. In certain embodiments, $R^{22}$ is optionally substituted alkyl. In certain embodiments, $R^{22}$ is optionally substituted $C_{1-6}$ alkyl. In certain embodiments, $R^{22}$ is optionally substituted $C_{1-4}$ alkyl. In certain embodiments, $R^{22}$ is optionally substituted $C_{1-3}$ alkyl. In certain embodiments, $R^{22}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), and —CH$_2$Si(CH$_3$)$_3$.

In certain embodiments, $R^{23}$ is selected from the group consisting of hydrogen, substituted hydroxyl, and optionally substituted alkyl. In certain embodiments, $R^{23}$ is hydrogen. In certain embodiments, $R^{23}$ is substituted hydroxyl, e.g., —OMe. In certain embodiments, $R^{23}$ is optionally substituted alkyl. In certain embodiments, $R^{23}$ is optionally substituted $C_{1-6}$ alkyl. In certain embodiments, $R^{23}$ is optionally substituted $C_{1-4}$ alkyl. In certain embodiments, $R^{23}$ is optionally substituted $C_{1-3}$ alkyl. In certain embodiments, $R^{23}$ is selected from the group consisting of hydrogen, —C(CH$_3$)$_3$ (-tBu), —CH(CH$_3$)$_2$ (-iPr), —CH$_2$CH$_2$CH$_3$ (-nPr), —CH$_2$CH$_3$ (-Et), —CH$_3$ (-Me), and —CH$_2$Si(CH$_3$)$_3$.

In certain embodiments, the optionally substituted pyridinyl ring is mono-substituted. Exemplary ligands, wherein $R^5$ and $R^6$ are joined to form a mono-substituted pyridinyl ring, X is C—$R^4$ and m is 1, include those of the Formula (EI-e1), (EI-e2), (EI-e3), and (EI-e4):

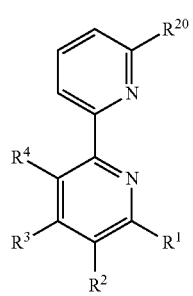

(EI-e1)

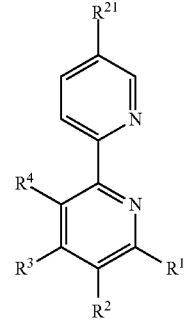

(EI-e2)

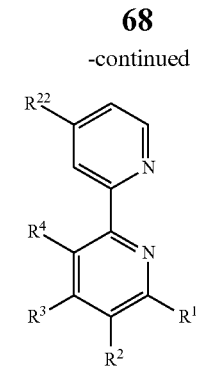

(EI-e3)

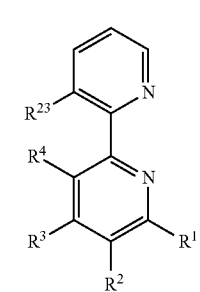

(EI-e4)

wherein $R^1$, $R^2$, $R^3$, and $R^4$, are as defined herein; and each instance of $R^{20}$, $R^{21}$, $R^{22}$, and $R^{23}$ is independently selected from the group consisting of halogen, silyl, and optionally substituted alkyl.

Exemplary ligands of the Formula (A) include, but are not limited to:

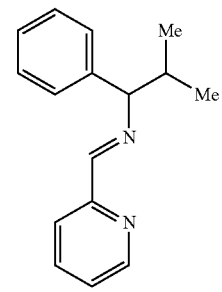

(L-1)

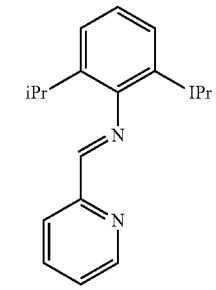

(L-2)

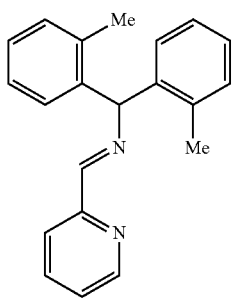 (L-3)
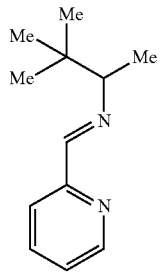 (L-4)
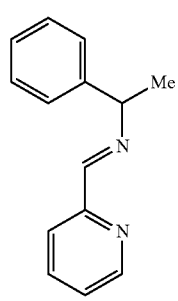 (L-5)
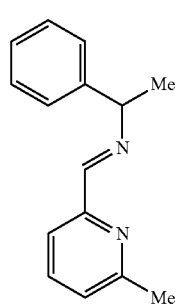 (L-6)
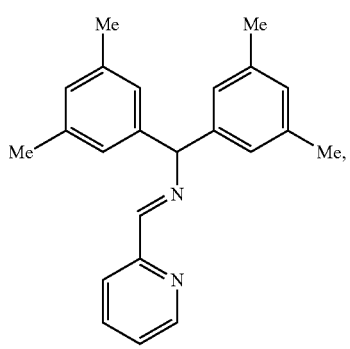 (L-7)
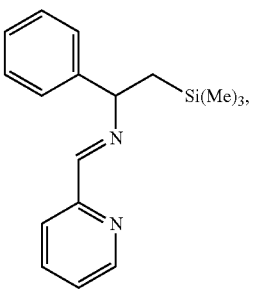 (L-8)
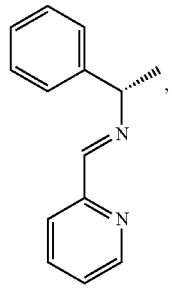 (L-9)
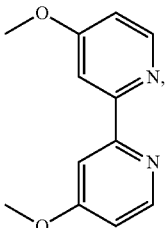 (L-10)
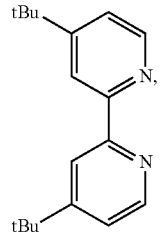 (L-11)
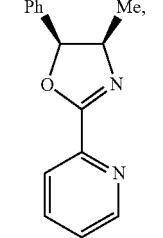 (L-12)
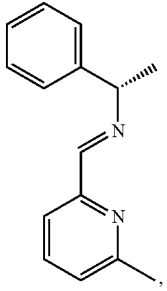 (L-13)

(L-14)
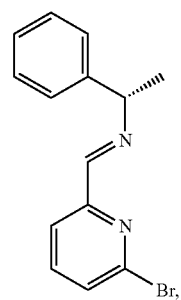
(L-15)
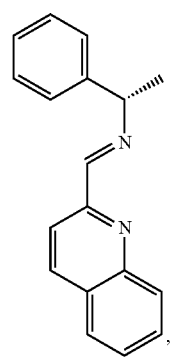
(L-16)
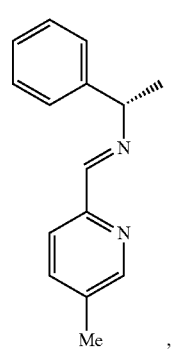
(L-17)
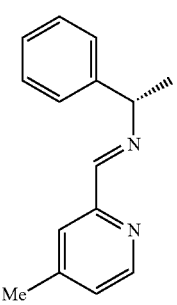
(L-18)
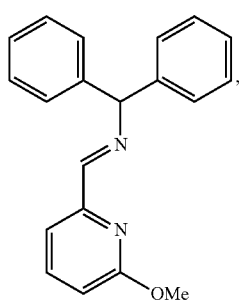
(L-19)
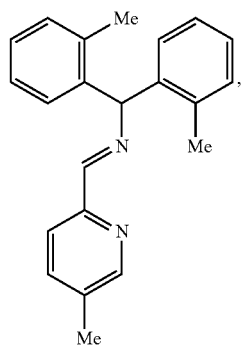
(L-20)
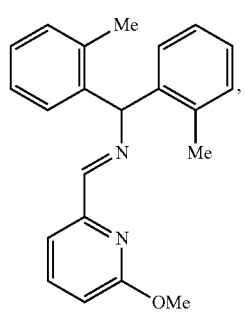
(L-21)
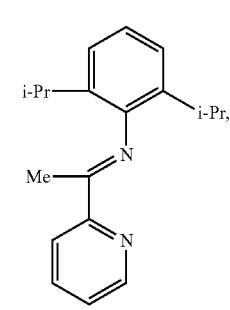
(L-22)
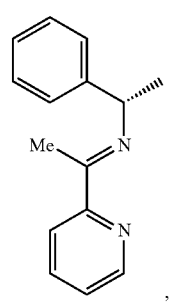
(L-23)
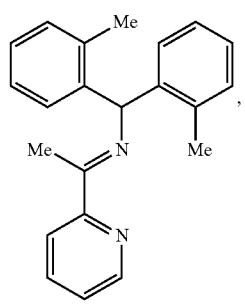

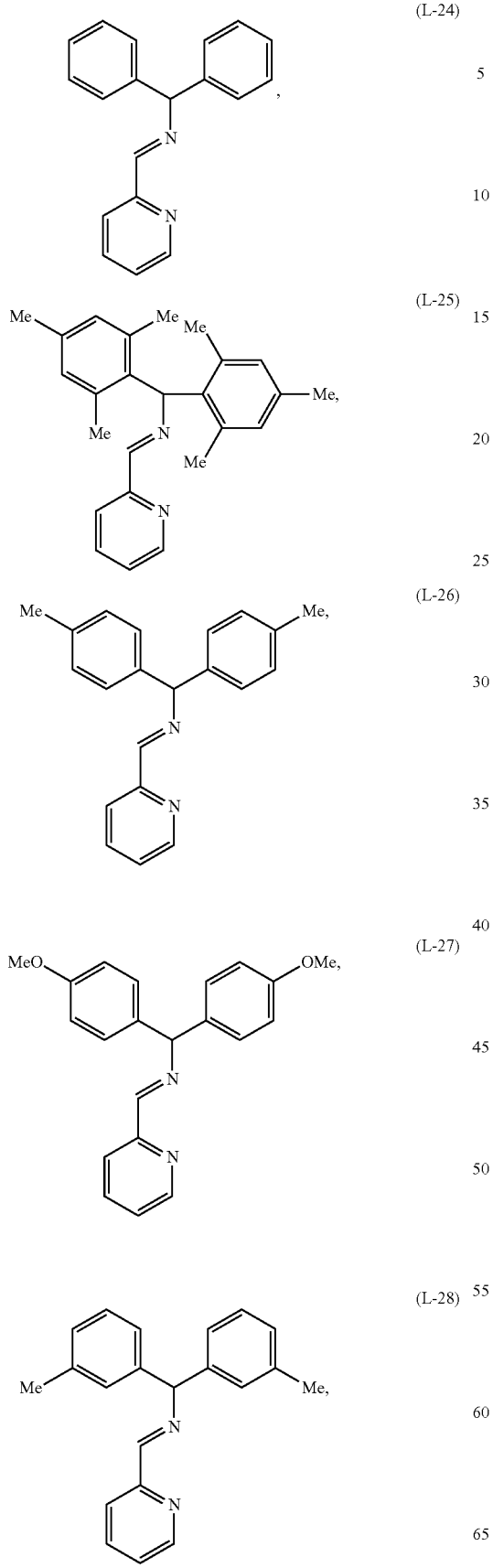
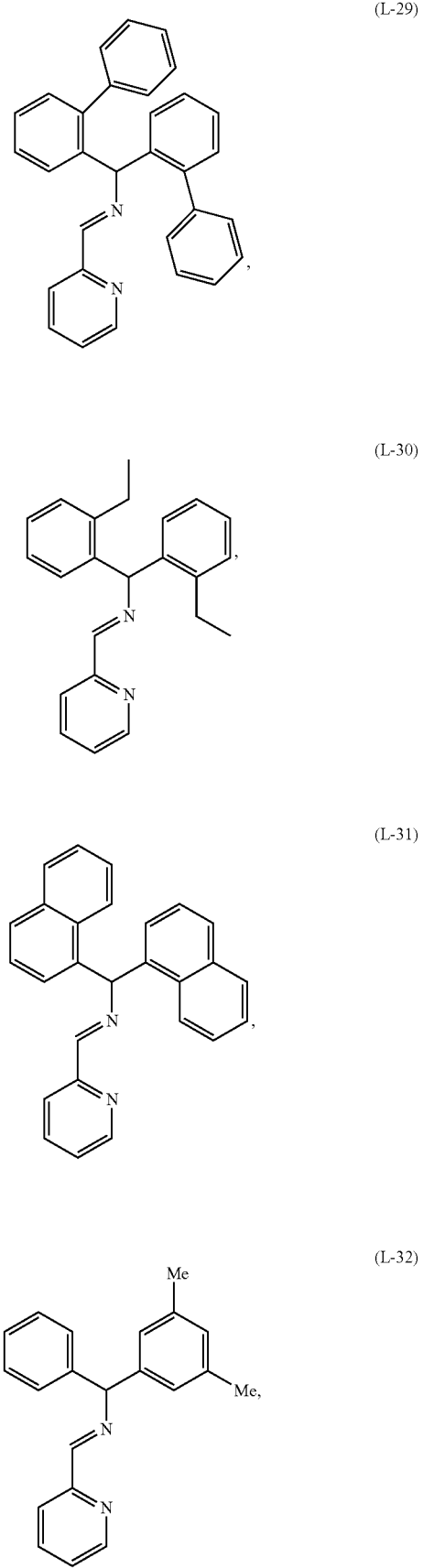

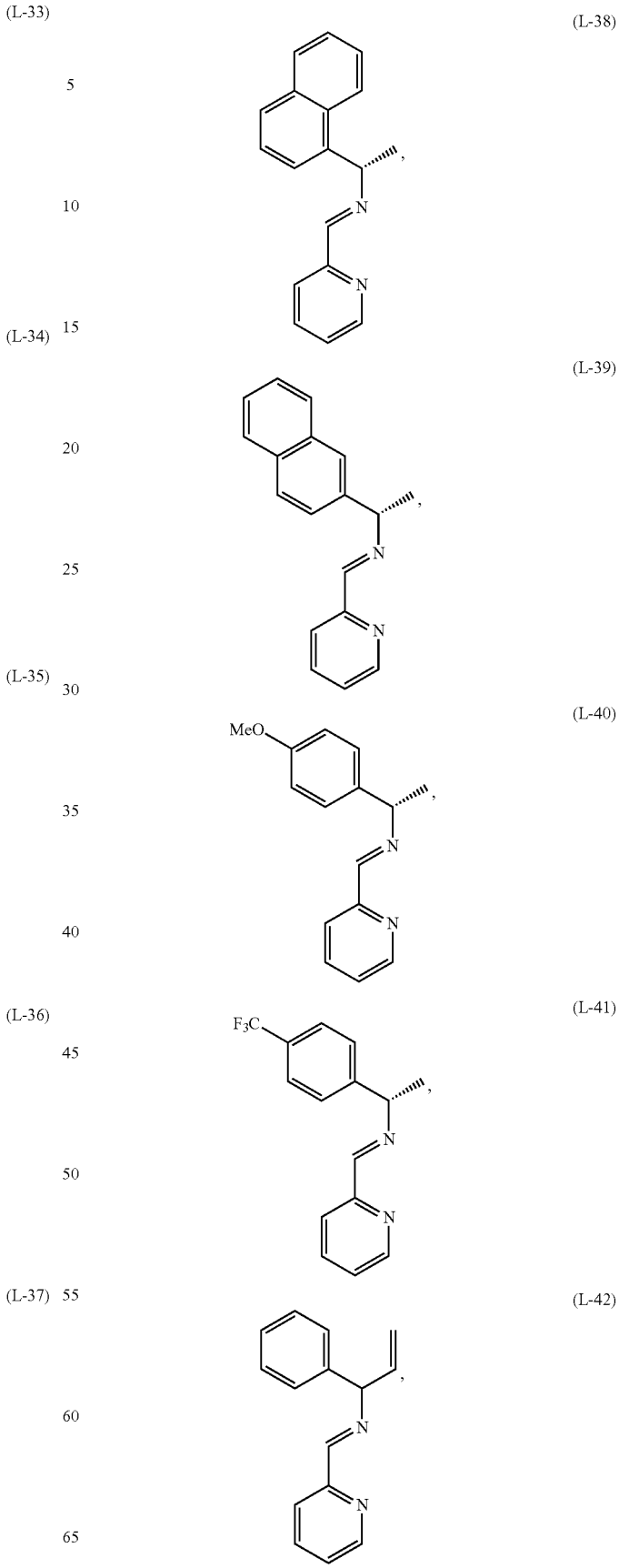

-continued
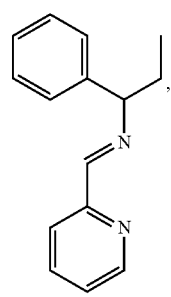 (L-43)
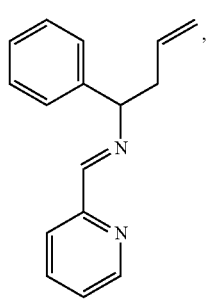 (L-44)
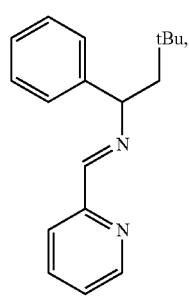 (L-45)
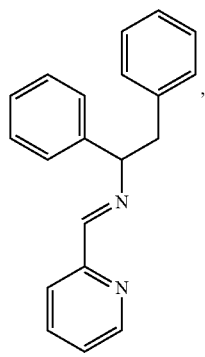 (L-46)
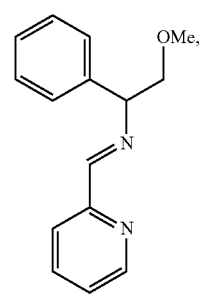 (L-47)
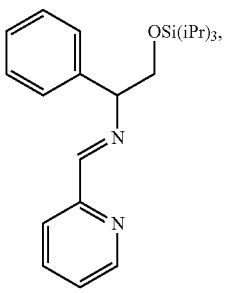 (L-48)
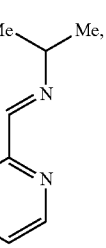 (L-49)
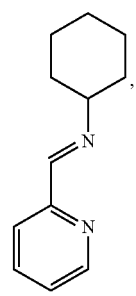 (L-50)
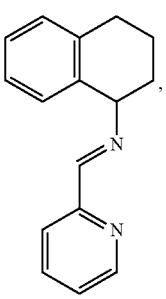 (L-51)
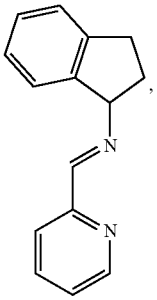 (L-52)

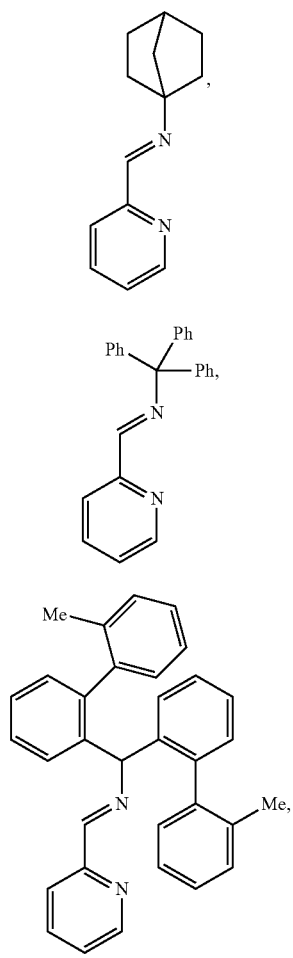
(L-53)
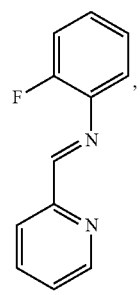
(L-58)
(L-54)
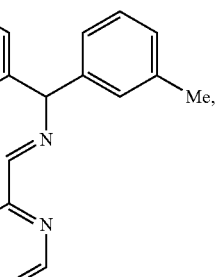
(L-59)
(L-55)
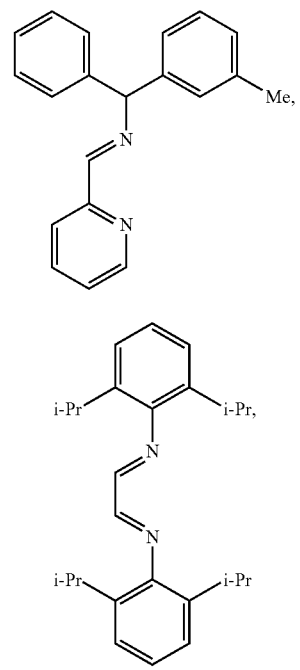
(L-60)
(L-56)
(L-61)
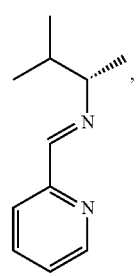
(L-57)
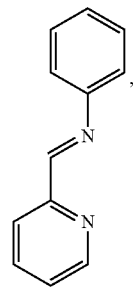
(L-62)
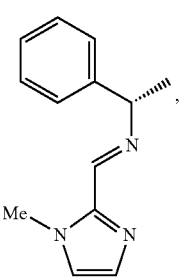

(L-63) 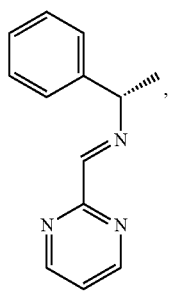
(L-64) 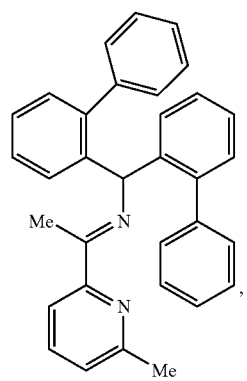
(L-65) 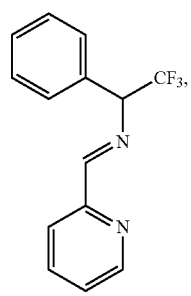
(L-66) 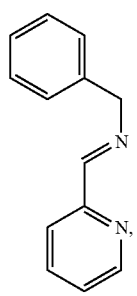
(L-67) 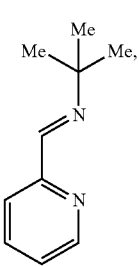
(L-68) 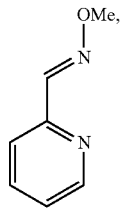
(L-69) 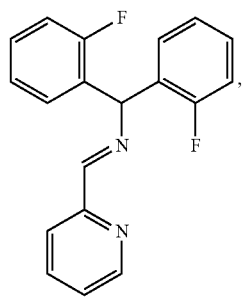
(L-70) 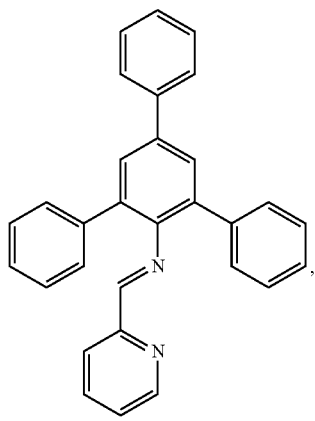
(L-71) 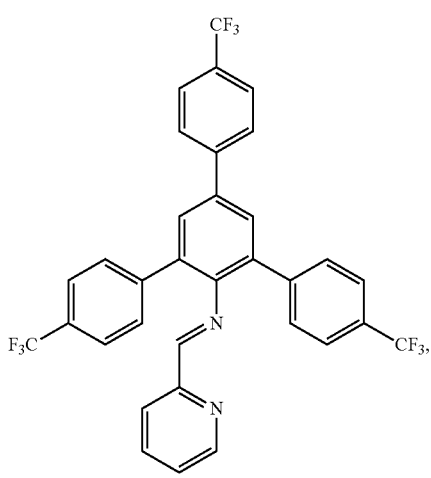

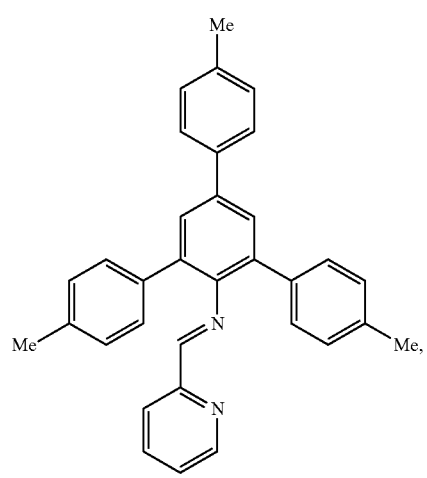 (L-72)
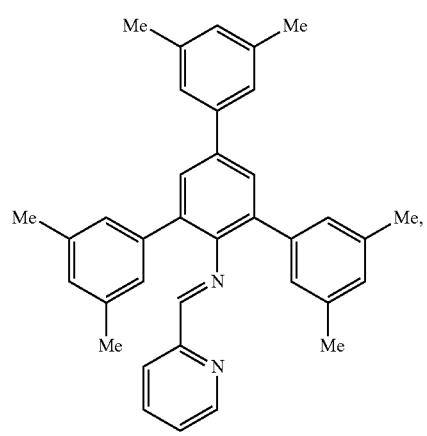 (L-73)
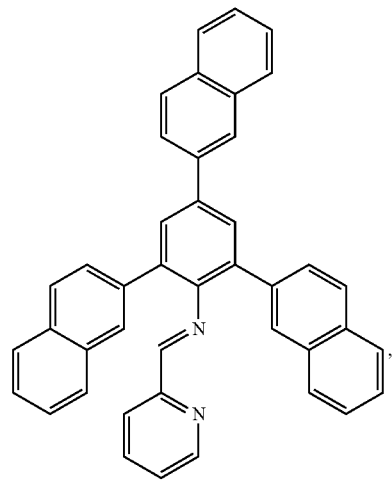 (L-74)
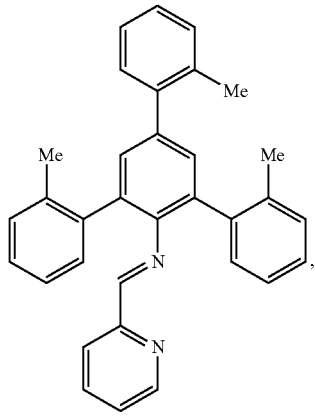 (L-75)
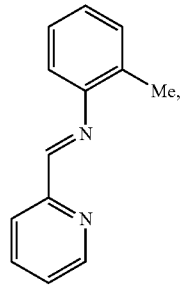 (L-76)
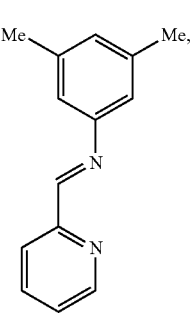 (L-77)
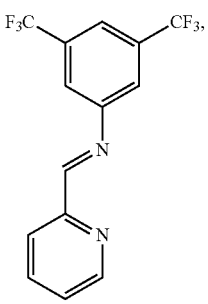 (L-78)
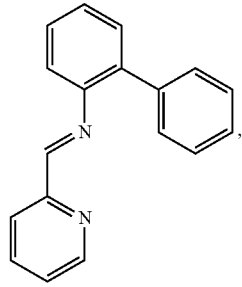 (L-79)

(L-80) 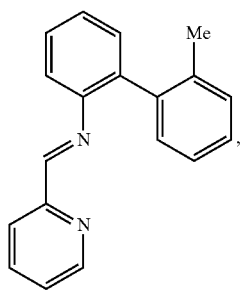
(L-81) 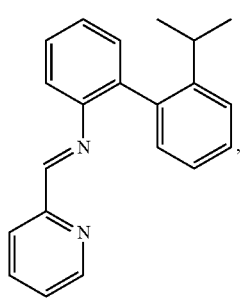
(L-82) 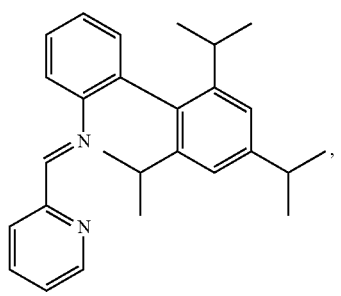
(L-83) 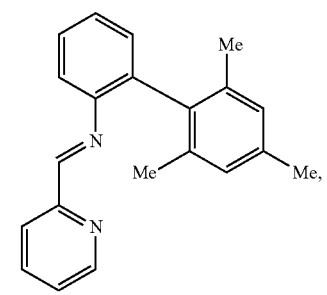
(L-84) 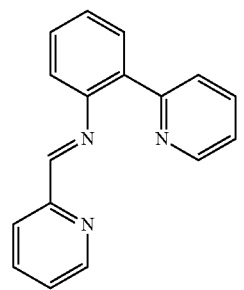
(L-85) 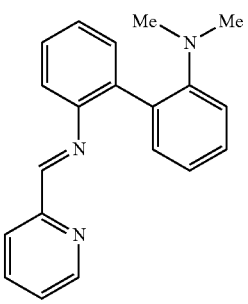
(L-86) 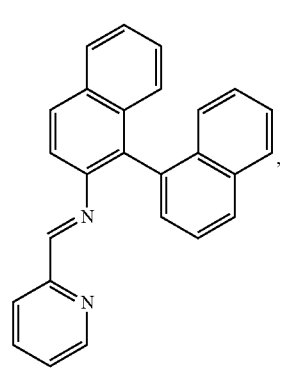
(L-87) 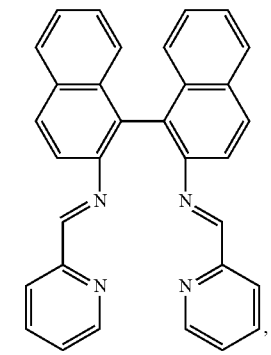
(L-88) 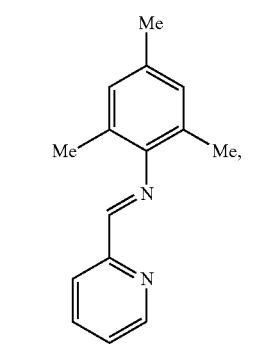
(L-89) 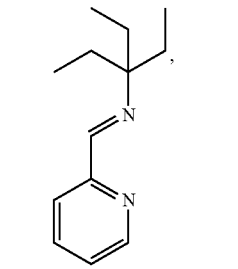

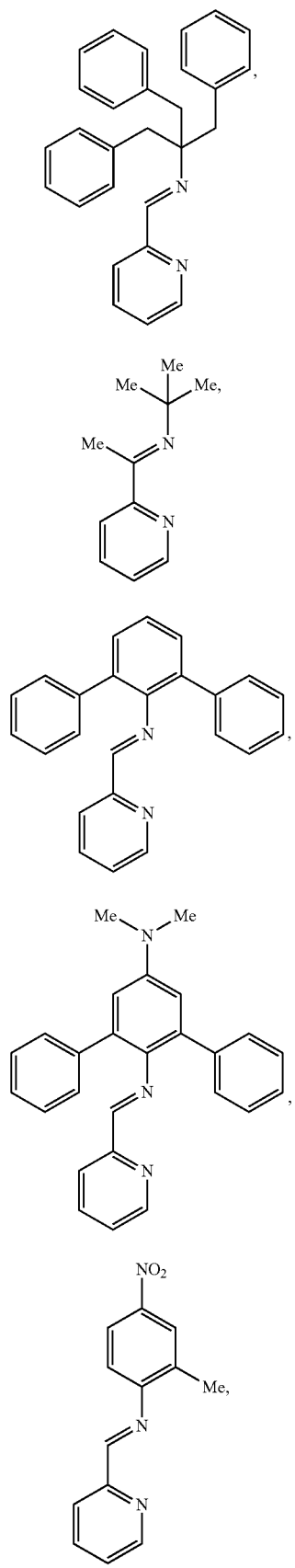
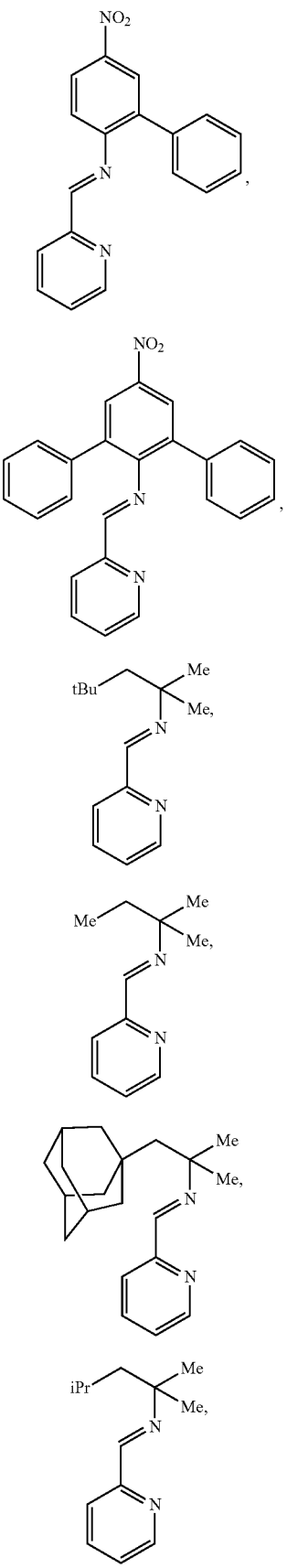

(L-101) 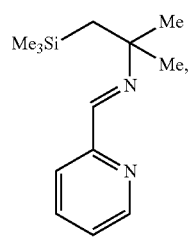
(L-102) 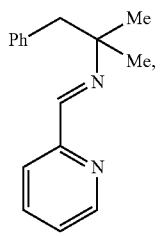
(L-103) 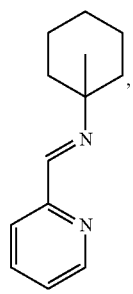
(L-104) 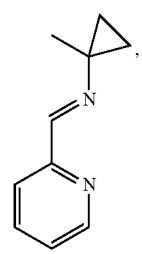
(L-105) 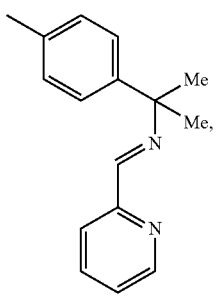
(L-106) 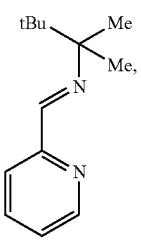
(L-107) 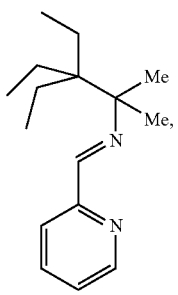
(L-108) 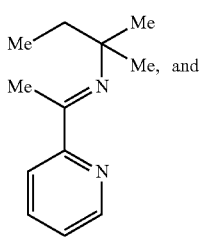
(L-109) 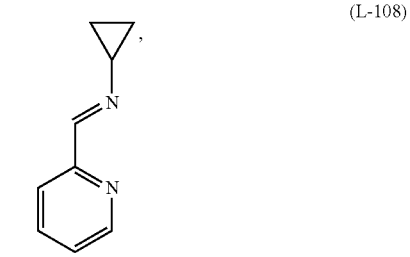
(L-110) 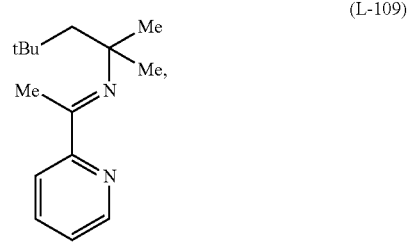
(L-111) 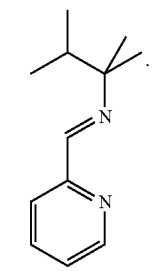
In certain embodiments, a metal complex is provided comprising iron and the ligand (L-1). In certain embodiments, the resulting iron complex is of the Formula (EII-L-1):

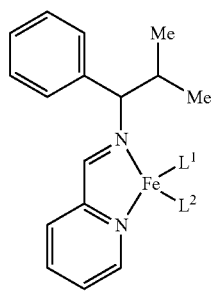

(EII-L-1)

wherein $L^1$ and $L^2$ are as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are —OAc.

In certain embodiments, a metal complex is provided comprising iron and the ligand (L-2). In certain embodiments, the resulting iron complex is of the Formula (EII-L-2):

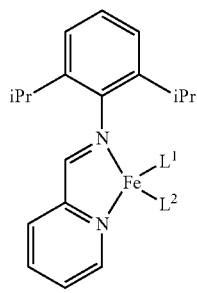

(EII-L-2)

wherein $L^1$ and $L^2$ are as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are —OAc.

In certain embodiments, a metal complex is provided comprising iron and the ligand (L-3). In certain embodiments, the resulting iron complex is of the Formula (EII-L-3):

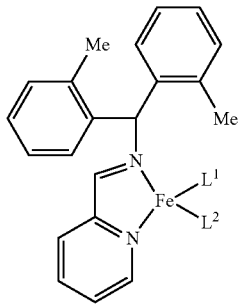

(EII-L-3)

wherein $L^1$ and $L^2$ are as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are —OAc.

In certain embodiments, a metal complex is provided comprising iron and the ligand (L-4). In certain embodiments, the resulting iron complex is of the Formula (EII-L-4):

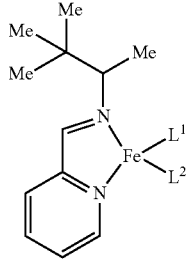

(EII-L-4)

wherein $L^1$ and $L^2$ are as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are —OAc.

In certain embodiments, a metal complex is provided comprising iron and the ligand (L-5). In certain embodiments, the resulting iron complex is of the Formula (EII-L-5):

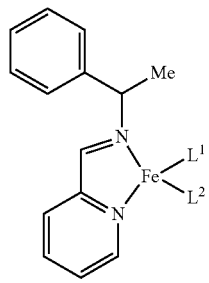

(EII-L-5)

wherein $L^1$ and $L^2$ are as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are —OAc.

In certain embodiments, a metal complex is provided comprising iron and the ligand (L-6). In certain embodiments, the resulting iron complex is of the Formula (EII-L-6):

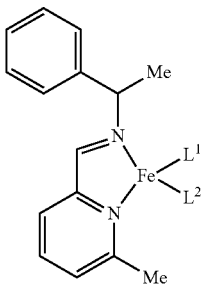

(EII-L-6)

wherein $L^1$ and $L^2$ are as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are —OAc.

In certain embodiments, a metal complex is provided comprising iron and the ligand (L-7). In certain embodiments, the resulting iron complex is of the Formula (EII-L-7):

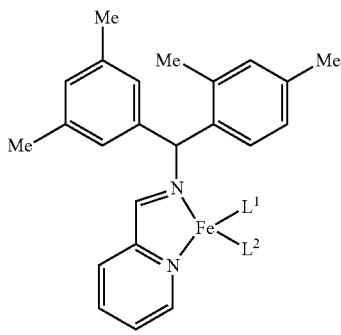

(EII-L-7)

wherein $L^1$ and $L^2$ are as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are —OAc.

In certain embodiments, a metal complex is provided comprising iron and the ligand (L-8). In certain embodiments, the resulting iron complex is of the Formula (EII-L-8):

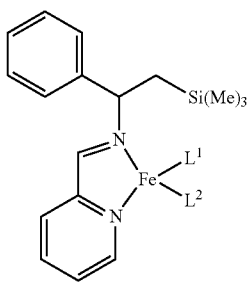

(EII-L-8)

wherein $L^1$ and $L^2$ are as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are —OAc.

In certain embodiments, a metal complex is provided comprising iron and the ligand (L-29). In certain embodiments, the resulting iron complex is of the Formula (EII-L-29):

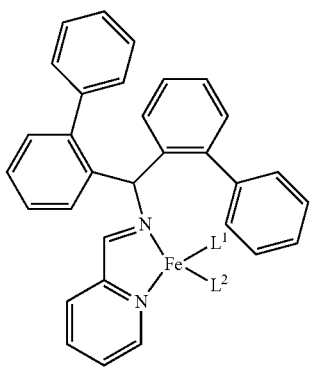

(EII-L-29)

wherein $L^1$ and $L^2$ are as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are —OAc.

In certain embodiments, a metal complex is provided comprising iron and the ligand (L-29). In certain embodiments, the resulting iron complex is of the Formula (EII-L-70):

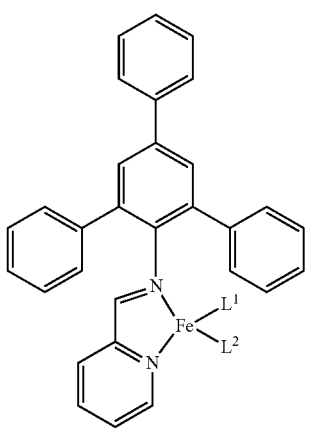

(EII-L-70)

wherein $L^1$ and $L^2$ are as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are —OAc.

In certain embodiments, a metal complex is provided comprising iron and the ligand (L-29). In certain embodiments, the resulting iron complex is of the Formula (EII-L-97):

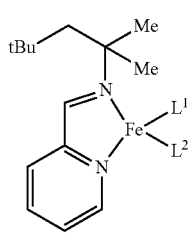

(EII-L-97)

wherein $L^1$ and $L^2$ are as defined herein. In certain embodiments, $L^1$ and $L^2$ are monodentate ligands. In certain embodiments, both $L^1$ and $L^2$ are halogen (e.g., chloro or bromo). In certain embodiments, both $L^1$ and $L^2$ are chloro. In certain embodiments, both $L^1$ and $L^2$ are —OAc.

Reaction Conditions

As generally defined above, provided is a method of preparing a polymer comprising polymerizing one or more alkenes in the presence of an iron complex, e.g., one alkene, two or more alkenes, three or more, four or more, etc. It is understood that using more than one type of alkene in the reaction will produce a co-polymer. Block copolymers and statistical copolymers generated from any of the aforementioned monomers are also contemplated. For example, block copolymers can be obtained by sequential addition of different 1,3-diene monomers during the course of the reaction.

In certain embodiments, the alkene is a diene. In certain embodiments, the diene is a 1,3-diene. In certain embodiments, the alkene is an optionally substituted 1,3-diene of the formula (i), as described herein. In certain embodiments, the diene is selected from the group consisting of isoprene, 1,3-butadiene, 1,3-pentadiene, cyclohexa-1,3-diene, trans-β-farnesene, and β-myrcene.

In certain embodiments, the step of polymerizing further comprises an initiator. In certain embodiments, the step of polymerizing comprises mixing the initiator and the complex prior to adding isoprene. In other embodiments, the step of polymerizing comprises mixing isoprene and the complex prior to adding the initiator.

Exemplary initiators include, but are not limited to, compounds of the formula "A-Z", wherein one of A and Z is independently silyl or boronyl, and one of A and Z is independently selected from the group consisting of boronyl, halogen, and silyl. In certain embodiments, both A and Z are independently selected from silyl. In certain embodiments, both A and Z are independently selected from boronyl. In certain embodiments, one of A and Z is silyl, and one of A and Z is halogen (e.g., chloro). In certain embodiments, one of A and Z is silyl, and one of A and Z is boronyl. In certain embodiments, the initiator is selected from the group consisting of dimethyl(phenyl)(4,4,5,5-tetramethyl-1,3,2-dioxaborolan-2-yl)silane), hexaphenyldisilane, hexamethyldisilane, 1,1,2,2-tetramethyl-1,2-diphenyldisilane, chlorotrimethylsilane, silaboranes, and diboranes.

In certain embodiments, the reaction comprises an alkylating agent, e.g., to activate the iron (II) complex, and a dealkylating agent, e.g., in order to allow polymerization. Transmetallating reagents are numerous and depending on the conditions, many abundant metals can be used, such as aluminum, zinc, magnesium, or calcium. These chain transfer agents (or chain-shuttling agents) will always be adjusted to fit with the industrial process. See, e.g., Britovsek et al, *Chem. Comm.*, 1998, 849-850; Gibson and Spitzmesser, *Chemical Reviews*, 2002, 103, 283-316; Britovsek et al., *J. Am. Chem. Soc.*, 2004, 126, 10701-10712; van Meurs et al, *J. Am. Chem. Soc.*, 2005, 127, 9913-9923; Small et al., *J. Am. Chem. Soc.*, 1998, 120, 4049-4050; Ittel et al., *Chemical Reviews*, 2000, 100, 1169-1204; Coates, *Chemical Reviews*, 2000, 100, 1223-1252; L. R. Sita, *Angew. Chem. Int. Ed.*, 2009, 48, 2464-2472; J. Wei et al., *Angew. Chem. Int. Ed.*, 2010, 49, 1768-1772, each of which is incorporated herein by reference.

Exemplary alkylating agents include, but are not limited to, trialkylaluminum reagents (e.g., $AlR_3$, wherein R is optionally substituted alkyl, e.g. trimethylaluminum, tri-isobutylaluminum, tri-ethylaluminum), dialkylzinc reagents (e.g., dimethylzinc, diethylzinc), dialkylmagnesium reagents (e.g., dibutylmagnesium, dimethylmagnesium, diethylmagnesium), calcium reagents (e.g., bis(allyl)calcium; see, e.g., Okuda et al. *Angew. Chem. Int. Ed.* (2009) 48:5715-5719), and Grignard reagents (such as methylmagnesium chloride and bromide as well as ethylmagnesium chloride and bromide). Exemplary dealkylating reagents include, but are not limited to, aluminates and borates as disclosed in Krossing et al. *Angew. Chem. Int. Ed.* 2004, 43, 2066-2090 (review); Krossing et al. *Angew. Chem. Int. Ed.* 2010, 49, 3228-3231 (and references herein); and Finze et al. *Angew. Chem. Int. Ed.* 2007, 46, 9180-9196, e.g., for example trispentafluoroborane (as a demethylating reagent), triphenylmethyl(trityl)tetrakis(3,5-bis(trifluoromethyl)phenyl)borate (original BArF or Kobayashi's anion) and triphenylmethyl(trityl)tetrakispentafluorophenyl borate ($BArF_{20}$). $BArF_{20}$ comprises a carbocation able to abstract the alkyl group from the complex in order to form an active cationic complex and a non-coordinating anion. Other exemplary reagents, similar to $BArF_{20}$, which may form an active cationic complex and a non-coordinating anion, are described in Krossing and Raabe *Angewandte Chemie International Edition* (2004) 43: 2066-2090; Honeychuck et al., *Inorganic Chemistry* (1989) 28: 2869-2886; Yakelis and Bergman, *Organometallics* (2005) 24: 3579-3581; Brookhart et al., *Organometallics* (1992) 11: 3920-3922.

In certain embodiments, the reaction comprises a reagent which acts as both an alkylating and dealkylating reagent in the reaction, e.g., the use of methylaluminoxane (MAO) serves both the role of alkylating reagent and dealkylating reagent (as a methylating and demethylating reagent) in order to activate the iron(II) chloride complex and allow polymerization. MAO is a classic way to activate ferrous chloride complexes. MAO may be used without a dealkylating agent and allows access the cationic complex directly. MAO can moreover be generated in situ using a partial hydrolysis of trimethylaluminum. Several methods to form MAO in situ have been designed. See, e.g., Glaser and X. Sun, *J. Am. Chem. Soc.*, 2011, 133, 13323-13336, and references cited therein.

In certain embodiments, the step of polymerizing further comprises an organic solvent. Exemplary organic solvents include, but are not limited to, ethers (e.g., tetrahydrofuran, diethylether, dioxane), polar aprotic solvents (e.g., ethyl acetate, acetone, dimethylsulfoxide, dimethylformamide), aromatic solvents (e.g., benzene, toluene, xylenes, pyridine), chlorinated hydrocarbon solvents (e.g., chloroform, dichloromethane, dichloroethane), and hydrocarbon solvents (e.g., hexanes, heptanes, methylcyclohexane).

In certain embodiments, the organic solvent comprises an ether. In certain embodiments, the ether is tetrahydrofuran.

In certain embodiments, the organic solvent comprises an aromatic solvent, a hydrocarbon solvent, or a mixture thereof. In certain embodiments, the organic solvent comprises toluene, ethyl benzene, heptane, hexanes, methylcyclohexane, or a mixture thereof.

In certain embodiments, the step of polymerizing is conducted at a temperature of between about −80° C. to about 100° C. In certain embodiments, the step of polymerizing is conducted at a temperature of between about −80° C. to about 30° C. In certain embodiments, the step of polymerizing is conducted at a temperature of between about −20° C. to about 60° C. In certain embodiments, the step of polymerizing is conducted at a temperature of between about 0° C. to about 60° C. In certain embodiments, the step of polymerizing is conducted at a temperature of between about 10° C. to about 60° C. In certain embodiments, the step of polymerizing is conducted at a temperature of between about 15° C. to about 45° C. In certain embodiments, the step of polymerizing is conducted at a temperature of between about 15° C. to about 30° C. In certain embodiments, the step of polymerizing is conducted at a temperature of between about 20° C. to about 30° C. In certain embodiments, the step of polymerizing is conducted at a temperature of between about 20° C. to about 25° C. In certain embodiments, the step of polymerizing is conducted at a temperature of about −78° C. In certain embodiments, the step of polymerizing is conducted at a temperature of about 25° C.

In certain embodiments, the step of polymerizing is conducted from about 10 hours to about 200 hours. In certain embodiments, the step of polymerizing is conducted from about 10 hours to about 100 hours. In certain embodiments, the step of polymerizing is conducted from about 10 hours to about 80 hours. In certain embodiments, the step of polymerizing is conducted from about 20 hours to about 80 hours. In certain embodiments, the step of polymerizing is conducted from about 20 hours to about 50 hours.

In certain embodiments, the step of polymerizing is conducted under inert atmosphere (e.g., under argon or nitrogen).

In certain embodiments, step of polymerizing is terminated by quenching with a hydrogen donating source (e.g., an organic alcohol such as methanol or ethanol, or an organic acid such as acetic acid).

In certain embodiments, the ratio of [monomer]/[Fe] employed is between about 500 to about 10,0000, e.g., greater than or equal to 500, 600, 700, 800, 900, 1000, 2000, 3000, 4000, 5000, 6000, 7000, 8000, or 9000.

Reaction Mechanism

Figure 2:
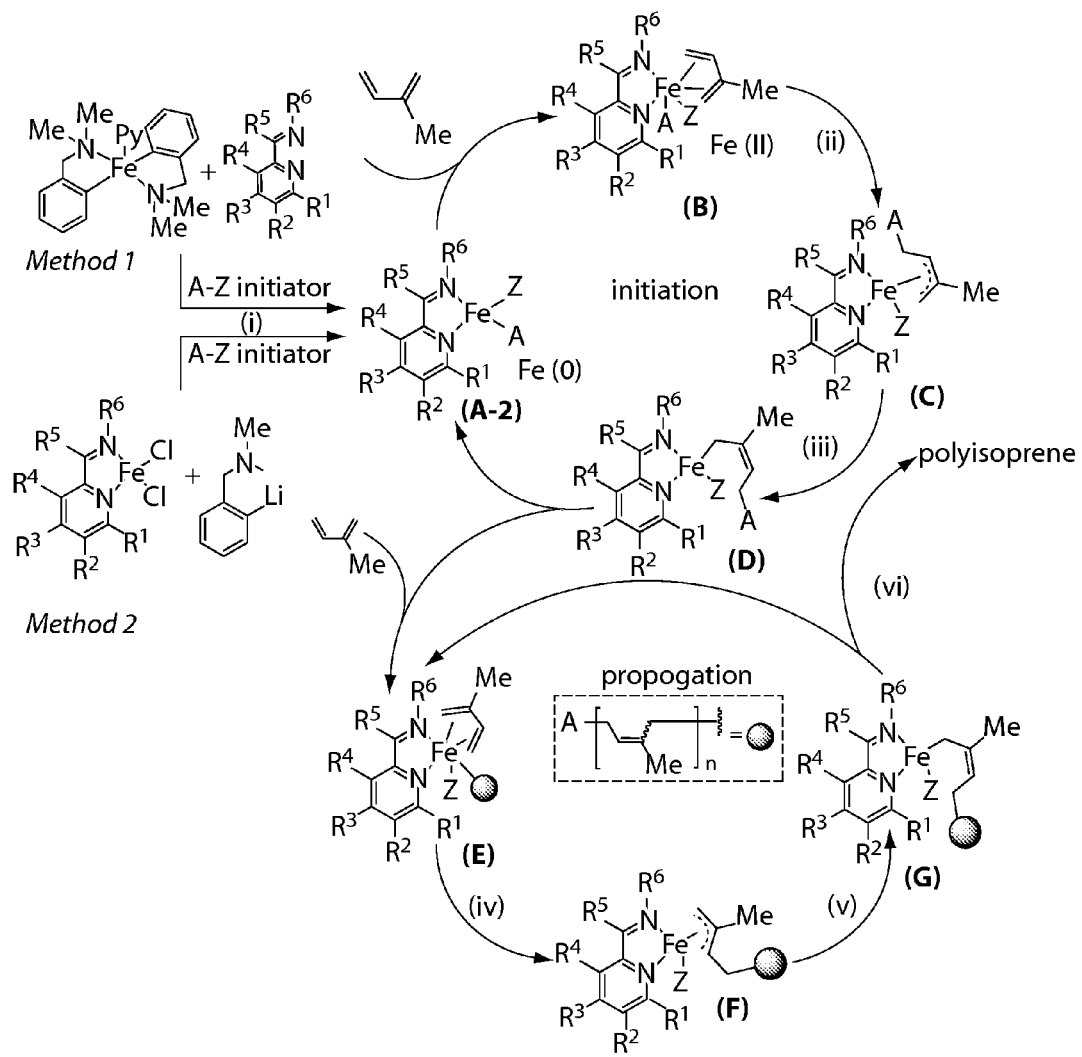

FIGS. 1 and 2 depict the proposed mechanism of the iron catalyzed polymerization of isoprene following Methods I or II.

In general, the initiation step in the polymerization involves in situ formation of an active iron complex (A1) or (A2):

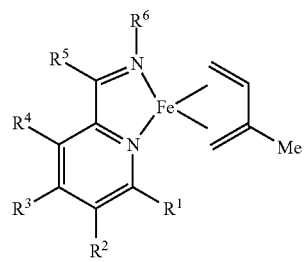
(A-1)

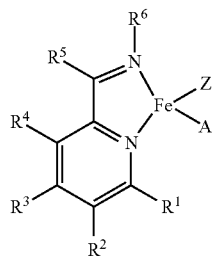
(A-2)

wherein $R^1$, $R^2$, $R^3$, $R^4$, $R^5$, and $R^6$ are as defined herein; and
one of A and Z is independently silyl or boronyl, and one of A and Z is independently selected from boronyl, halogen, and silyl.

Oxidative addition of the initiator (FIG. 1) or coordination of a first isoprene (FIG. 2) generates an in situ complex of Formula:

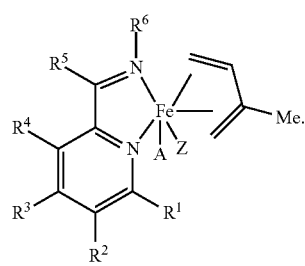

Migratory insertion of the initiator from the iron to the first isoprene generates an in situ complex of Formula:

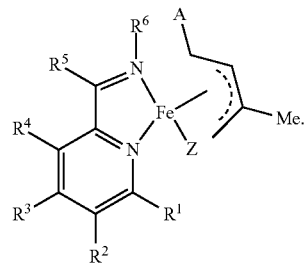

Pi→sigma rearrangement of the preceding complex generates an in situ complex of Formula:

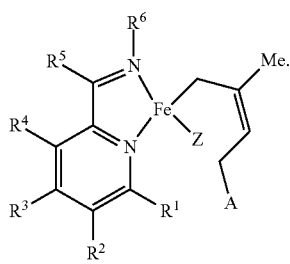

The propogation step in the catalysis involves coordination of a second or subsequent isoprene to provide an in situ complex of Formula:

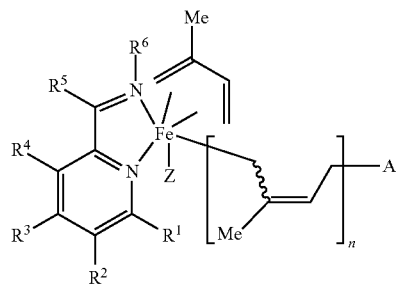

wherein $R^1$, $R^2$, $R^3$, $R^4$, $R^5$, $R^6$, A and Z are as defined herein; and n is an integer of between 1 and 100,00, inclusive.

Migratory insertion of the second or subsequent isoprene to the first isoprene generates an in situ complex of Formula:

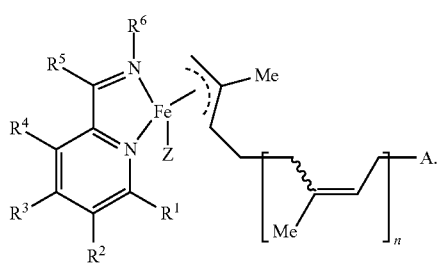

Pi→sigma rearrangement of the preceding complex generates an in situ complex of Formula:

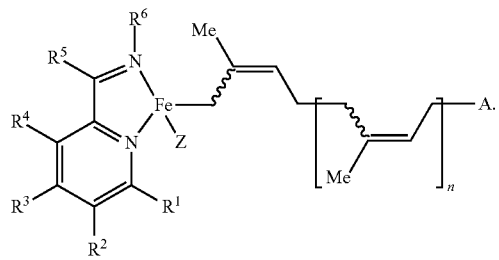

The propogation step continues for another (n−1) cycles, or until the polymerization is terminated.

Figure 3:
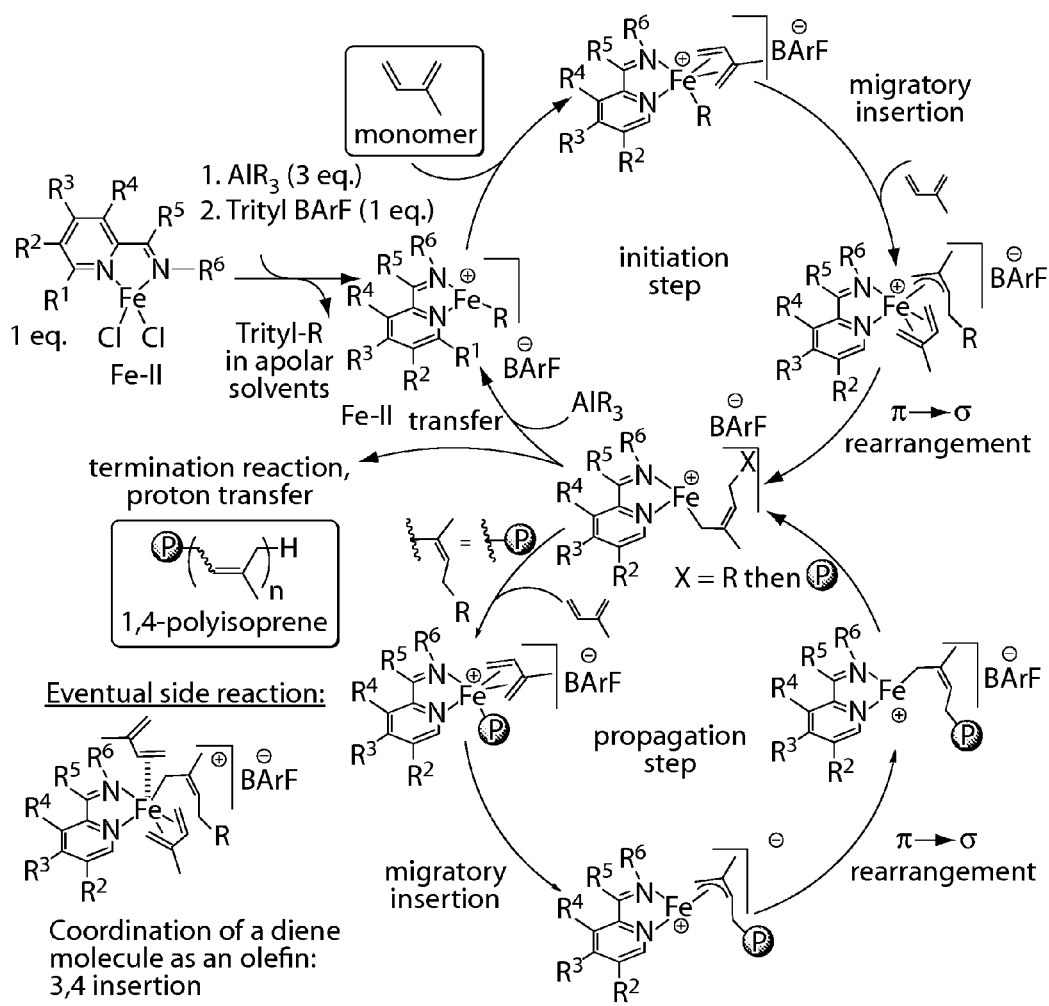
Figure 4:
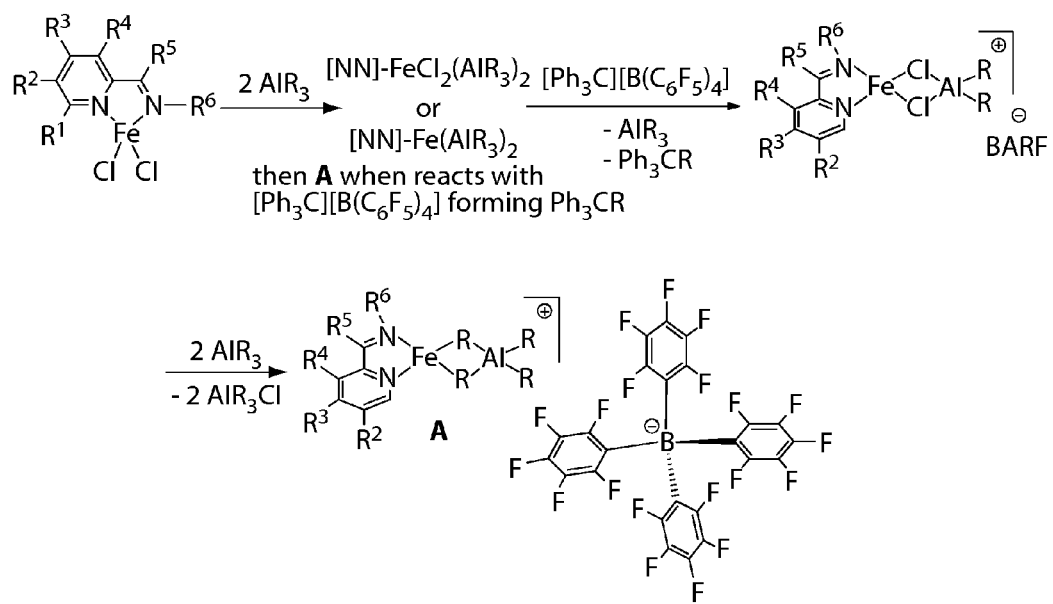
FIG. 4 depicts the proposed mechanism of the putative alkylation/dealkylation sequence leading to the proposed active cationic Fe complex (via activation of a precatalyst), enabling the diene polymerization.
Figure 5A:
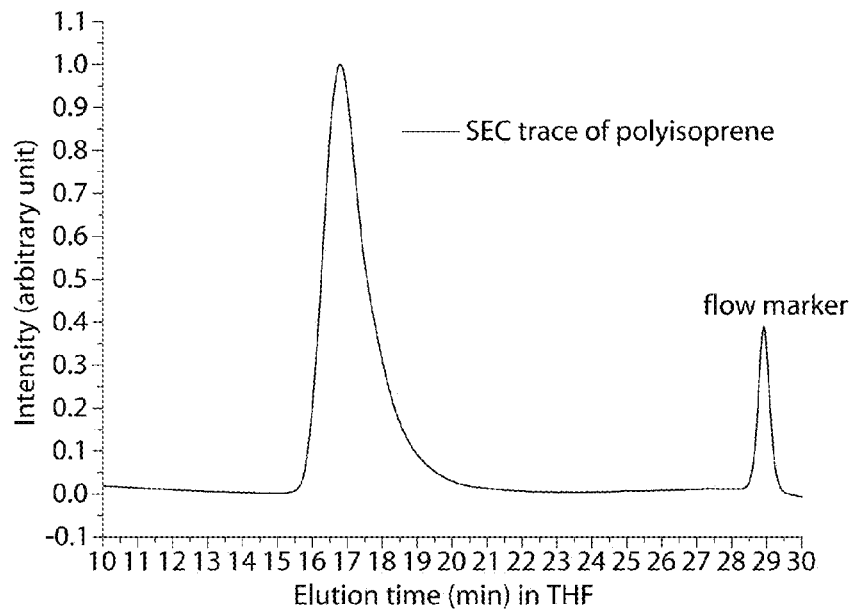
FIGS. 5A-5E depicts the size exclusion chromatography (SEC) traces of polymers prepared following the inventive methods.
Figure 5B:
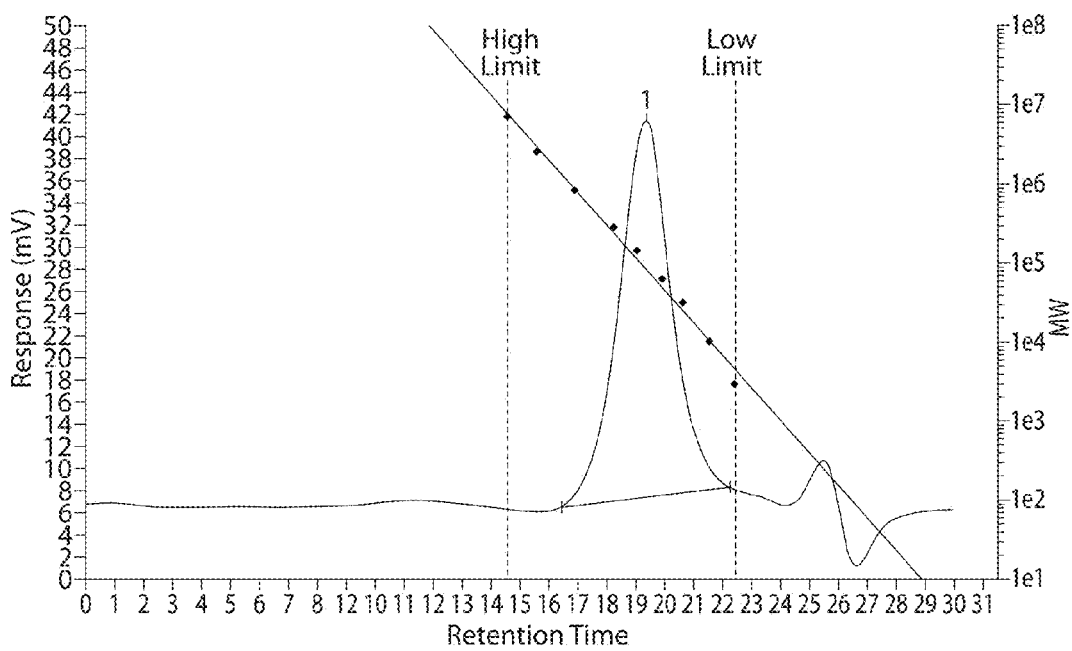
Figure 5C:
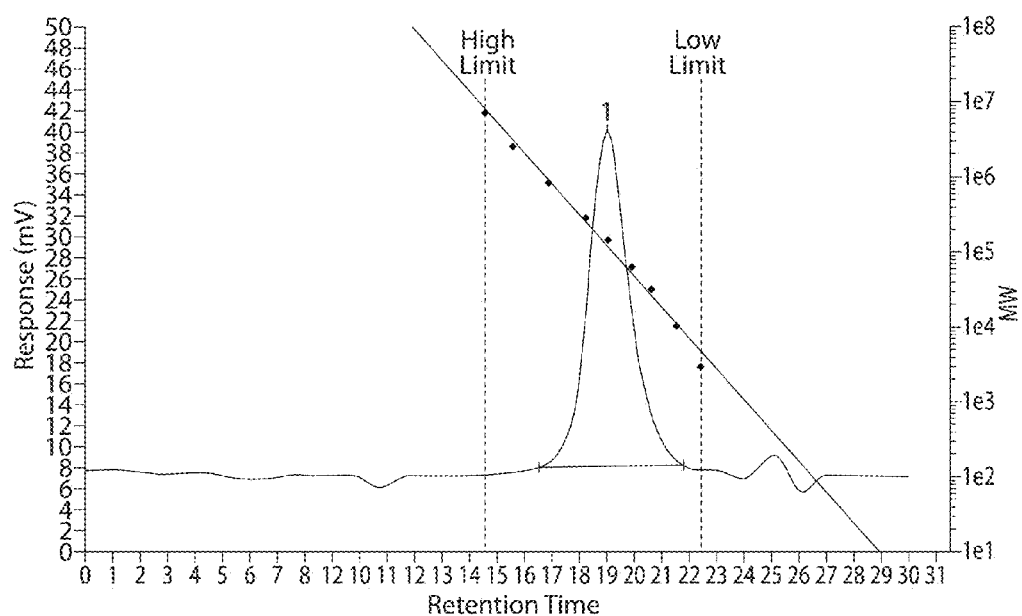
Figure 5D:
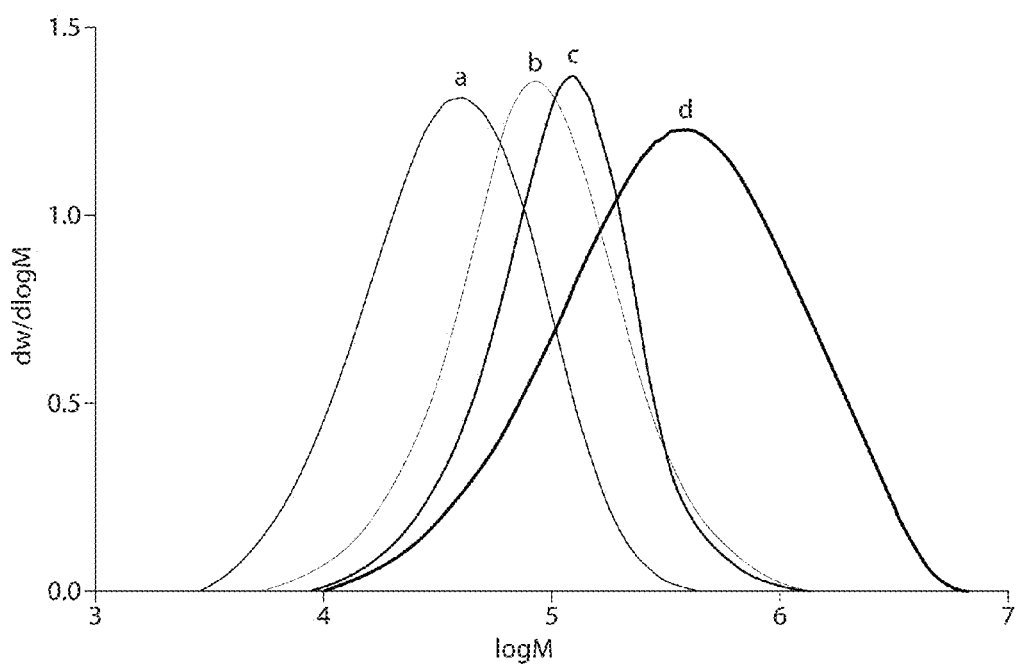
Figure 5E:
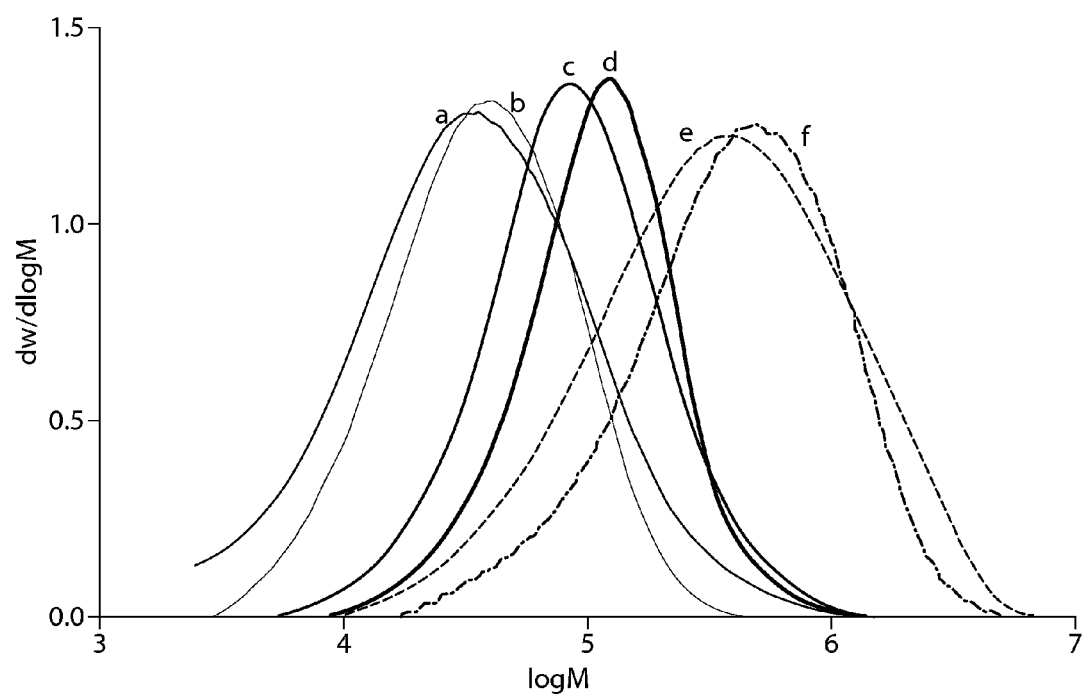

FIG. 3 depicts the proposed mechanism of the iron catalyzed polymerization of isoprene following Method III. The below complex is the putative active cationic Fe catalyst after the alkylation/dealkylation sequence allowing its activation. Technically, this could be called the initiator of the polymerization reaction:

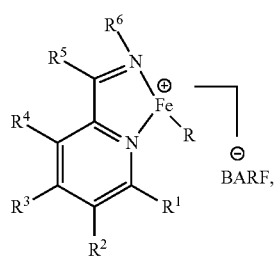

which forms a putative cationic Fe intermediate after coordination of a diene monomer:

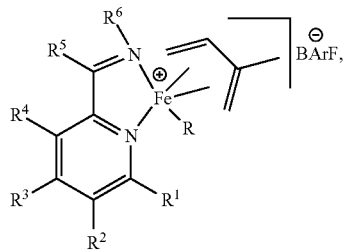

which then forms a putative cationic Fe intermediate after migratory insertion of a monomer unit in the R—Fe bond (to form a pi-allyl or p-allyl ligand) and coordination of a new diene monomer:

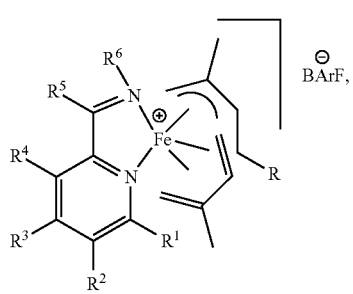

which then forms a putative cationic Fe intermediate after migratory insertion and pi-sigma (or p-s) rearrangement:

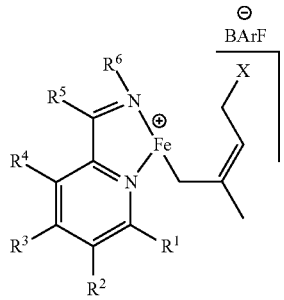

wherein X is R or the polymer ⊖, which then forms a putative cationic Fe intermediate bearing both a diene monomer and a growing polymer chain as ligands, in addition to the iminopyridine:

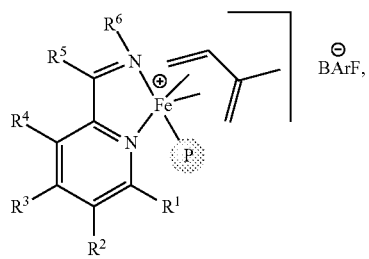

which then forms a putative cationic Fe intermediate after migratory insertion of a monomer unit in the P—Fe bond (to form a pi-allyl or p-allyl ligand)

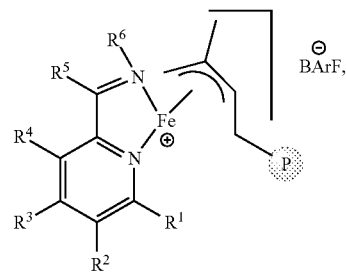

which then forms a putative cationic Fe intermediate after migratory insertion of a monomer unit in the P—Fe bond (to form a pi-allyl or p-allyl ligand) and pi-sigma (or p-s) rearrangement:

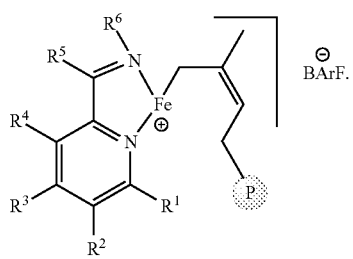

It has been found that, under certain conditions, following Method III preferentially generates either cis-1,4-polyisoprene or trans-1,4-polyisoprene depending upon the ligand used. For example, use of ligand (L-97) in the reaction preferentially generates trans-1,4-polyisoprene while use of ligand (L-70) preferentially generates cis-1,4-polyisoprene.

EXAMPLES

In order that the invention described herein may be more fully understood, the following examples are set forth. It should be understood that these examples are for illustrative purposes only and are not to be construed as limiting this invention in any manner.

Materials and Methods

All reactions were carried out under an inert atmosphere (nitrogen) using standard techniques for manipulating air-sensitive compounds unless otherwise stated. All glassware was stored in an oven or was flame-dried prior to use under an inert atmosphere of nitrogen or argon as stated. Anhydrous solvents were obtained either by filtration through drying columns ($CH_2Cl_2$) on an mBraun system or by distillation over sodium/benzophenone ($Et_2O$, toluene, pentane, heptane, methylcyclohexane). Analytical thin-layer chromatography (TLC) was performed on EMD TLC plates pre-coated with 250 μm thickness silica gel 60 F254 plates visualized by fluorescence quenching under UV light and stained using potassium permanganate stain. Flash chromatography was performed on Silicycle silica gel 60 (40-63 μm) using a forced flow of eluent at 0.3-0.5 bar pressure. Yields refer to purified and spectroscopically pure compounds. $^1H$ NMR spectra were recorded on a Varian Unity/Inova 500 spectrometer operating at 500 MHz. $^{13}C$ NMR spectra were recorded on a Varian Unity/Inova 500 spectrometer operating at 125 MHz.

10 seconds and 5 seconds were used as relaxation times for $^1H$ NMR and $^{13}C$ NMR, respectively, for the determination of selectivities in polymerization reactions. Prior to use, $CDCl_3$ was passed through a plug of basic alumina and $CD_2Cl_2$ was degassed by the freeze-pump-thaw method and dried over 4 Å molecular sieves. Chemical shifts are reported in parts per million from tetramethylsilane with the solvent resonance as the internal standard. For $^1H$ NMR: $CDCl_3=\delta$ 7.26 ppm, $CD_2Cl_2$: δ 5.32 ppm. For $^{13}C$ NMR: $CDCl_3=\delta$ 77.16 ppm, $CD_2Cl_2=\delta$ 53.80 ppm. Data are reported as follows: chemical shift, multiplicity (s=singlet, d=doublet, t=triplet, q=quartet, m=multiplet and br=broad), coupling constant in Hz, and integration. For paramagnetic molecules, the $^1H$ NMR and $^{13}C$ NMR data are reported with the chemical shift followed by the peak width at half-height in Hz. Magnetic susceptibility measurements for all iron complexes were obtained using the Evans method (see, e.g., Evans, D. F. *J. Chem. Soc.* (1959) 2003-2005) and are reported as follows: (field strength, solvent): $\mu_{eff}$ (concentration in mg/mL). $^{57}Fe$ Mössbauer spectra were measured with a constant acceleration spectrometer (SEE Co, Minneapolis, Minn.). Isomer shifts are quoted relative to Fe metal at room temperature. Molar masses of polyisoprenes were determined using size exclusion chromatography with a Varian GPC, fitted with a 3-column set and a RI detector, using THF as the eluent and polystyrenes as standards (Grinstaff group, Boston University). SEC chromatography data are reported as average polar mass in weight ($M_w$) in g/mol and polydispersity (D).

Reagents: Reagents were purchased from standard commercial sources (Aldrich, Strem, Alfa Aesar or TCI) and used as received unless otherwise noted. 2-pyridinecarboxaldehyde (Aldrich, 98%) was distilled prior to use. Tert-octylamine (Aldrich, 97%) was distilled prior to use. Supermesitylamine (Aldrich, 98%) was used as received. Iron(II) chloride (98% Aldrich or 99.99% Strem) was used as received. Trityl tetrakis(pentafluorophenyl)borate (bright yellow powder, 98%, Strem) was used as received. Isoprene (99%, Alfa Aesar or TCI) was distilled over (n-Bu)$_2$Mg or Al(i-Bu)$_3$ and degassed by the freeze-pump-thaw method prior to use. Trimethylaluminum, triethylaluminum and tri-isobutylaluminum were purchased neat in metallic canisters from Aldrich (respectively 97, 93, and 95% purity). Trialkylaluminum alkylating reagents were either cannula-transferred from storage tanks of distilled (no major difference was observed).

Synthesis of Ligands

All the ligands described and depicted herein were obtained via condensation of a substituted aldehyde or ketone with a primary amine. Complex amines were synthesized prior to the condensation. Many amines and substituted aldehydes and ketones are commercially available which allows for a one-step synthesis (imine condensation).

An exemplary general method is depicted below for the synthesis of iminopyridine ligands:

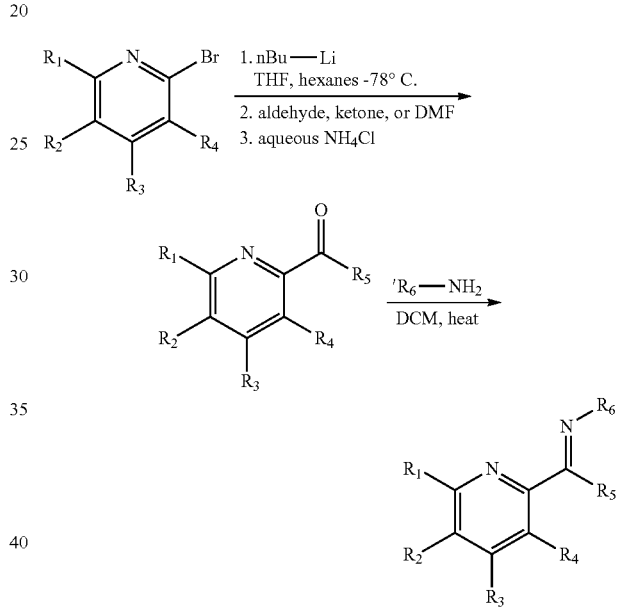

Ligand (L-1)

Synthesis of ligand (L-1), (E)-2-methyl-1-phenyl-N-(pyridin-2-ylmethylene)propan-1-amine.

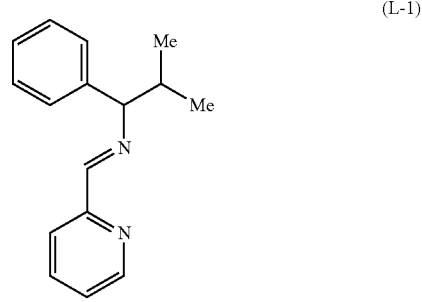 [SMILES: CC(C)C(/N=C/c1ccccn1)c1ccccc1]

To benzaldehyde (26.1 g, 25.0 mL, 0.246 mol, 1.21 equiv) in toluene (100 mL) was added 2-methoxyaniline (25.1 g, 23.0 mL, 0.204 mol, 1.00 equiv). The reaction mixture was heated to reflux with azeotropic removal of water with a Dean-Stark trap for 12 h. The reaction mixture was concentrated and dried under high vacuum to afford (E)-N-benzylidene-2-methoxyaniline as a yellow oil (43.0 g, >99% yield).

To (E)-N-benzylidene-2-methoxyaniline (5.00 g, 23.7 mmol, 1.00 equiv) in anhydrous THF (106 mL) at 0° C. was added isopropylmagnesium chloride (13.0 mL, 2.0 M in Et$_2$O, 26.0 mmol, 1.10 equiv) and the reaction mixture was stirred at 0° C. for 1 h. A saturated aqueous solution of NH$_4$Cl (50 mL) was added and the aqueous layer was extracted with Et$_2$O (3×50 mL). The combined organic layers were washed with brine (25 mL), dried over MgSO$_4$, filtered, and concentrated. The residue was purified by chromatography on SiO$_2$, eluting with 2% v/v EtOAc/hexanes, to give 2-methoxy-N-(2-methyl-1-phenylpropyl)aniline as a colorless oil (1.72 g, 28% yield).

To 2-methoxy-N-(2-methyl-1-phenylpropyl)aniline (1.36 g, 5.34 mmol, 1.00 equiv) in 2:1 v/v MeCN/H$_2$O (76 mL) was added AgNO$_3$ (0.271 g, 1.60 mmol, 0.300 equiv) and the reaction mixture was heated to 60° C. Ammonium persulfate (8.58 g, 37.6 mmol, 7.04 equiv) was added in three portions over 15 min and the reaction mixture was heated at 60° C. for 1 h. An aqueous solution of HCl (10 mL, 2 N in H$_2$O) was added. The reaction mixture was filtered through a celite pad, eluting with H$_2$O. The aqueous layer was washed with Et$_2$O (3×30 mL) and the combined organic layers were washed with HCl (2×30 mL, 0.5 N in H$_2$O). The combined aqueous layers were basified with 2.5 M NaOH and the aqueous layer was extracted with Et$_2$O (4×20 mL). The combined organic layers were washed with brine, dried over MgSO$_4$, filtered, and concentrated. The residue was purified by Kugelrohr distillation (50 mTorr, 60° C.) to give 2-methyl-1-phenylpropan-1-amine as a colorless oil (0.257 g, 32% yield).

In air, 2-pyridinecarboxaldehyde (0.185 g, 0.164 mL, 1.72 mmol, 1.00 equiv) was added to a solution of 2-methyl-1-phenylpropan-1-amine (0.257 g, 1.72 mmol, 1.00 equiv) in CH$_2$Cl$_2$ (8 mL). After heating at reflux for 2 h with azeotropic removal of water using a Dean-Stark trap, the reaction mixture was concentrated under reduced pressure and dried under high vacuum to give ligand (L-1), (E)-2-Methyl-1-phenyl-N-(pyridin-2-ylmethylene)propan-1-amine, as a yellow oil (0.379 g, 92% yield).

Ligand (L-2)

An exemplary synthesis of ligand (L-2), (E)-2,6-diisopropyl-N-(pyridin-2-ylmethylene)aniline, is provided in Wu et al., *J. Am. Chem. Soc.* (2009) 131:12915-12917 incorporated herein by reference.

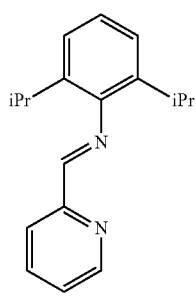

(L-2)

Ligand (L-3)

Synthesis of ligand (L-3), (E)-N-(pyridin-2-ylmethylene)-1,1-di-o-tolylmethanamine:

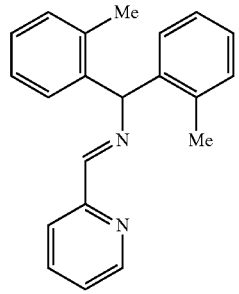

(L-3)

The following procedure was adapted from Zhang et al. (*Org. Lett.* 2008, 10, 5429-5432). To Mg turnings (1.53 g, 63.0 mmol, 1.50 equiv) in THF (50 mL) in an oven-dried round-bottom flask fitted with a reflux condenser was added 2-methyliodobenzene (11.0 g, 6.40 mL, 1.20 equiv) dropwise. The reaction mixture was heated to reflux for 1 h. To the reaction mixture was added o-tolunitrile (4.94 g, 5.00 mL, 42.2 mmol, 1.00 equiv) and the reaction mixture was heated to reflux for 22 h. The reaction mixture was cooled to 23° C. and a suspension of LiAlH$_4$ (1.97 g, 51.9 mmol, 1.23 equiv) in THF (50 mL) was added and the reaction mixture was heated to reflux for 25 h. The reaction mixture was cooled to 23° C. and H$_2$O (2 mL) was added dropwise. A solution of NaOH (2 mL, 1 M in H$_2$O) was added slowly and 8 mL H$_2$O was added. The reaction mixture was filtered through a celite pad, eluting with EtOAc, and concentrated. The residue was purified by Kugelrohr distillation (240 mTorr, 200° C.) to give di-o-tolylmethanamine as a yellow oil (8.52 g, 96% yield).

In air, 2-pyridinecarboxaldehyde (36.0 mg, 32.0 µL, 0.336 mmol, 1.00 equiv) was added to a solution of di-o-tolylmethanamine (73.1 mg, 0.346 mmol, 1.03 equiv) in CH$_2$Cl$_2$ (5 mL). After heating at reflux for 30 min with azeotropic removal of water using a Dean-Stark trap, the reaction mixture was concentrated under reduced pressure and dried under high vacuum to give ligand (L-3), (E)-N-(Pyridin-2-ylmethylene)-1,1-dio-tolylmethanamine, as a yellow oil (0.102 g, 98% yield).

Ligand (L-4)

An exemplary synthesis of ligand (L-4), (E)-3,3-dimethyl-N-(pyridin-2-ylmethylene)butan-2-amine, is provided in Wu et al., *J. Am. Chem. Soc.* (2010) 132:13214-13216 incorporated herein by reference.

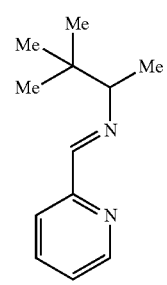

(L-4)

Ligand (L-5)

An exemplary synthesis of ligand (L-5), (E)-1-phenyl-N-(pyridin-2-ylmethylene)ethanamine, is provided in Moreau et al., *Org. Lett.* (2009) 11:337-339 incorporated herein by reference.

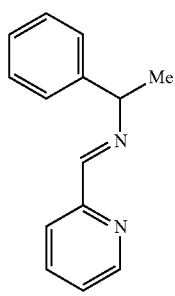

(L-5)

Ligand (L-6)

An exemplary synthesis of ligand (L-6), (E)-N-((6-methylpyridin-2-yl)methylene)-1-phenylethanamine, is provided in Wu et al., *J. Am. Chem. Soc.* (2010) 132:13214-13216 incorporated herein by reference.

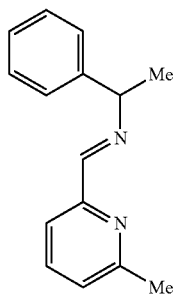

(L-6)

Ligand (L-7)

An exemplary synthesis of ligand (L-7), (E)-1-(2,4-dimethylphenyl)-1-(3,5-dimethylphenyl)-N-(pyridin-2-ylmethylene)methanamine, is provided in Wu et al., *J. Am. Chem. Soc.* (2009) 131:12915-12917 incorporated herein by reference.

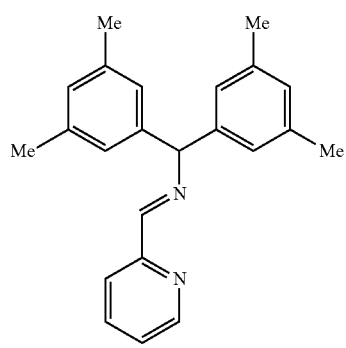

(L-7)

Ligand (L-8)

An exemplary synthesis of ligand (L-8), (E)-1-phenyl-N-(pyridin-2-ylmethylene)-2-(trimethylsilyl)ethanamine, is provided in Moreau et al., *Org. Lett.* (2009) 11:337-339 incorporated herein by reference.

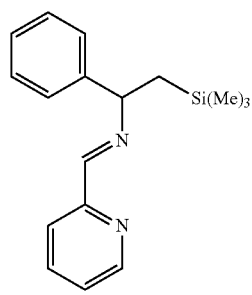

(L-8)

Other ligands, (L-9) to (L-110), were prepared by similar methods. (L-111) may also be prepared following these methods.

Ligand (L-70)

Synthesis of ligand (L-70), (E)-3,5-Diphenyl-N-(pyridin-2-ylmethylene)biphenyl-2-amine

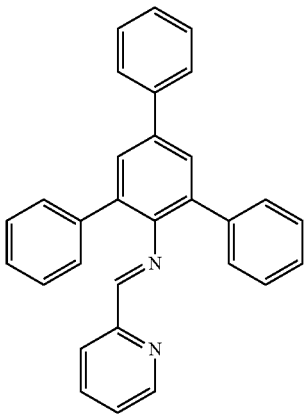

(L-70)

In air, to a solution of 2,4,6-triphenylaniline (0.964 g, 3.00 mmol, 1.00 equiv) in $CH_2Cl_2$ (10 mL) was added 2-pyridinecarboxaldehyde (0.326 g, 0.290 mL, 3.05 mmol, 1.02 equiv). After heating at reflux for 20 h with azeotropic removal of water using a Dean-Stark trap, the reaction mixture was concentrated under reduced pressure. The residue was purified by trituration with hexanes and dried in vacuo to give the title compound as a yellow solid (1.18 g, 96% yield).

Melting Point: 141-144° C. NMR Spectroscopy: $^1$H NMR (500 MHz, $CDCl_3$, 25° C., δ): 8.52 (d, J=4.6 Hz, 1H), 8.08 (s, 1H), 7.89 (d, J=7.8 Hz, 1H), 7.67-7.70 (m, 3H), 7.66 (s, 2H), 7.44-7.48 (m, 7H), 7.30-7.37 (m, 5H), 7.22-7.27 (m, 2H). $^{13}$C NMR (125 MHz, $CDCl_3$, 25° C., δ): 165.4, 154.3, 149.4, 147.1, 140.6, 139.8, 137.9, 136.5, 134.0, 130.2, 128.9, 128.8, 128.2, 127.4, 127.1, 126.9, 125.1, 121.2. HRMS-ESI (m/z): Calcd for $[C_{30}H_{22}N_2+Na]$, 433.1675. Found, 433.1657.

Ligand (L-97)

Synthesis of ligand (L-97), (E)-2,4,4-Trimethyl-N-(pyridin-2-ylmethylene)pentan-2-amine.

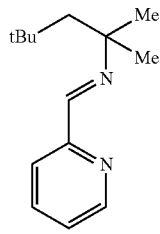

(L-97)

In air, to a solution of 2-pyridinecarboxaldehyde (0.338 g, 0.300 mL, 3.15 mmol, 1.01 equiv) in CH$_2$Cl$_2$ (10 mL) was added tert-octylamine (0.402 g, 0.500 mL, 3.11 mmol, 1.00 equiv). After heating at reflux for 1.5 h with azeotropic removal of water using a Dean-Stark trap, the reaction mixture was concentrated under reduced pressure. The residue was purified by bulb-to-bulb distillation (250 mTorr, 140° C.) to give the title compound as a colorless oil (0.639 g, 94% yield).

NMR Spectroscopy: $^1$H NMR (500 MHz, CDCl$_3$, 25° C., δ): 8.61 (dt, J=4.9, 1.0 Hz, 1H), 8.33 (s, 1H), 8.03 (dt, J=7.8, 1.0 Hz, 1H), 7.71 (m, 1H), 7.26 (ddd, J=7.8, 4.9, 1.0 Hz, 1H), 1.70 (s, 2H), 1.33 (s, 6H), 0.94 (s, 9H). $^{13}$C NMR (125 MHz, CDCl$_3$, 25° C., δ): 156.0, 155.9, 149.3, 136.6, 124.4, 120.8, 61.6, 56.6, 32.2, 31.9, 29.7. HRMS-ESI (m/z): Calcd for [C$_{14}$H$_{22}$N$_2$+H], 219.1856. Found, 219.1854.

General Procedure for Synthesis Fe(II)Chloride Complexes

The iminopyridine ligand (1.00 equiv) was added to iron (II) chloride (1.00 equiv) in dichloromethane (concentration: 1 M) under inert atmosphere. The reaction mixture was stirred at 23° C. for a day. The reaction mixture was filtered and the filtrate concentrated under reduced pressure to give a pink to red foam. The residue was triturated with diethyl ether and the resulting pink to deep red solid is dried under reduced pressure (yields typically >90%). X-ray quality crystals were grown by vapor diffusion of diethyl ether into a solution of the complex in dichloromethane.

Iron-(L-9) Complex

Synthesis of the Fe(II)chloride complex from ligand.

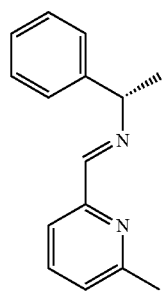

(L-9)

-continued

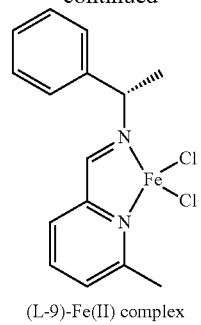

(L-9)-Fe(II) complex (S,E)-N-((6-methylpyridin-2-yl)methylene)-1-phenylethanamine (L9) (0.450 g, 2.00 mmol, 1.00 equiv) is added to iron (II) chloride (0.254 g, 2.00 mmol, 1.00 equiv) in dichloromethane (2.0 mL) under inert atmosphere. The reaction mixture is stirred at 23° C. for 28 h. The reaction mixture is filtered and the filtrate concentrated under reduced pressure to give a pink foam. The residue is triturated with diethyl ether and the resulting pink solid is dried under reduced pressure (0.683 g, 97%). X-ray quality crystals were grown by vapor diffusion of diethyl ether into a solution of the complex in dichloromethane.

Melting point: 166-169° C. dec. Magnetic susceptibility (500 MHz, CD$_2$Cl$_2$): μeff=5.32 μB. NMR Spectroscopy: $^1$H NMR (500 MHz, CD$_2$Cl$_2$, 23° C., δ): 83.0 (Δv$_{1/2}$=304 Hz, 1H), 79.6 (Δv$_{1/2}$=416 Hz, 1H), 57.4 (Δv$_{1/2}$=76 Hz, 1H), 49.4 (Δv$_{1/2}$=94 Hz, 1H), 4.59 (Δv$_{1/2}$=34 Hz, 2H), 4.50 (Δv$_{1/2}$=37 Hz, 1H), −5.02 (Δv$_{1/2}$=265 Hz, 2H), −16.5 (Δv$_{1/2}$=55 Hz, 1H), −23.4 (Δv$_{1/2}$=546 Hz, 3H), −28.9 (Δv$_{1/2}$=425 Hz, 3H). $^{13}$C NMR (125 MHz, CD$_2$Cl$_2$, δ): 501.17, 312.47 (d, J=123.1 Hz), 241.04, 236.89 (d, J=150.4 Hz), 209.19, 160.27, 126.11, 122.77, 120.22, 101.14, 93.45, 5.99, 264.96. Anal. Calcd for C$_{15}$H$_{16}$N$_2$Cl$_2$Fe: C, 51.32; H, 4.59; N, 7.98; Cl, 20.20; Fe, 15.91. Found: C, 51.29; H, 4.40; N, 7.93; Cl, 20.25; Fe, 15.98.

Iron-(L-70) Complex

Synthesis of the Fe(II)chloride complex, (E)-2,4,4-trimethyl-N-(pyridin-2-ylmethylene)pentan-2-amine iron(II) chloride, from ligand (L-70).

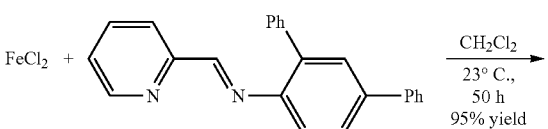

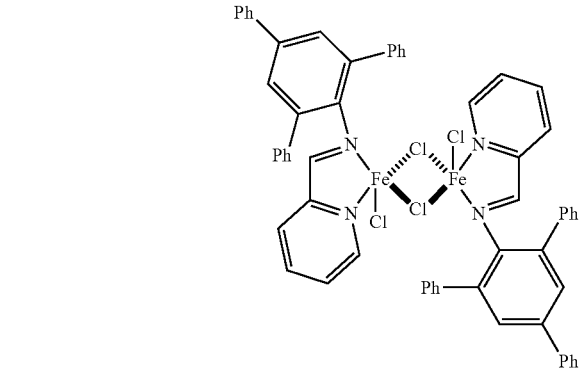

A solution of (E)-3,5-diphenyl-N-(pyridin-2-ylmethylene)biphenyl-2-amine (L-70) (0.150 g, 0.365 mmol, 1.00 equiv)

in CH$_2$Cl$_2$ (5 mL) was added to iron(II) chloride (46.3 mg, 0.365 mmol, 1.00 equiv). The reaction mixture was stirred at 23° C. for 72 h. The reaction mixture was filtered over a celite pad, and the filtrate was discarded. The residue on the filter cake was eluted with about 5 mL CH$_2$Cl$_2$ and the filtrate was concentrated under reduced pressure. The residue was washed with pentane (2×7 mL) and dried under reduced pressure to afford the title compound as a green solid (0.187 g, 95% yield). The title compound was insufficiently soluble in a deuterated solvent, such as CD$_2$Cl$_2$, to obtain a $^{13}$C NMR. X-Ray quality crystals were grown from vapor diffusion of diethyl ether into a solution of the title compound in CH$_2$Cl$_2$ (3 to 5 mg dissolved in 1 mL, then filtered over a pad of celite) at −35° C. over 48 h.

Magnetic susceptibility (500 MHz, CD$_2$Cl$_2$): $\mu_{eff}$=5.28$\mu_B$ (7.4 mg/mL). NMR Spectroscopy: $^1$H NMR (500 MHz, CD$_2$Cl$_2$, 25° C., δ): 80.28 ($\Delta v_{1/2}$=187 Hz), 67.24 ($\Delta v_{1/2}$=741 Hz), 57.84 ($\Delta v_{1/2}$=73 Hz), 54.71 ($\Delta v_{1/2}$=68 Hz), 7.35 ($\Delta v_{1/2}$=19 Hz), 6.62 ($\Delta v_{1/2}$=42 Hz), 6.51 ($\Delta v_{1/2}$=28 Hz), 4.65 ($\Delta v_{1/2}$=54 Hz), 3.72 ($\Delta v_{1/2}$=29 Hz), 1.84 ($\Delta v_{1/2}$=22 Hz), 1.28 ($\Delta v_{1/2}$=50 Hz), 0.88 ($\Delta v_{1/2}$=24 Hz), −13.62 ($\Delta v_{1/2}$=58 Hz). Mössbauer Spectroscopy (95 K): δ=1.07 mm/s, $\Delta E_Q$=3.35 mm/s. Anal Calcd for C$_{60}$H$_{44}$Cl$_4$Fe$_2$N$_4$: C, 67.07; H, 4.13; N, 5.21. Found: C, 66.23; H, 4.22; N, 4.87.

Figure 6:
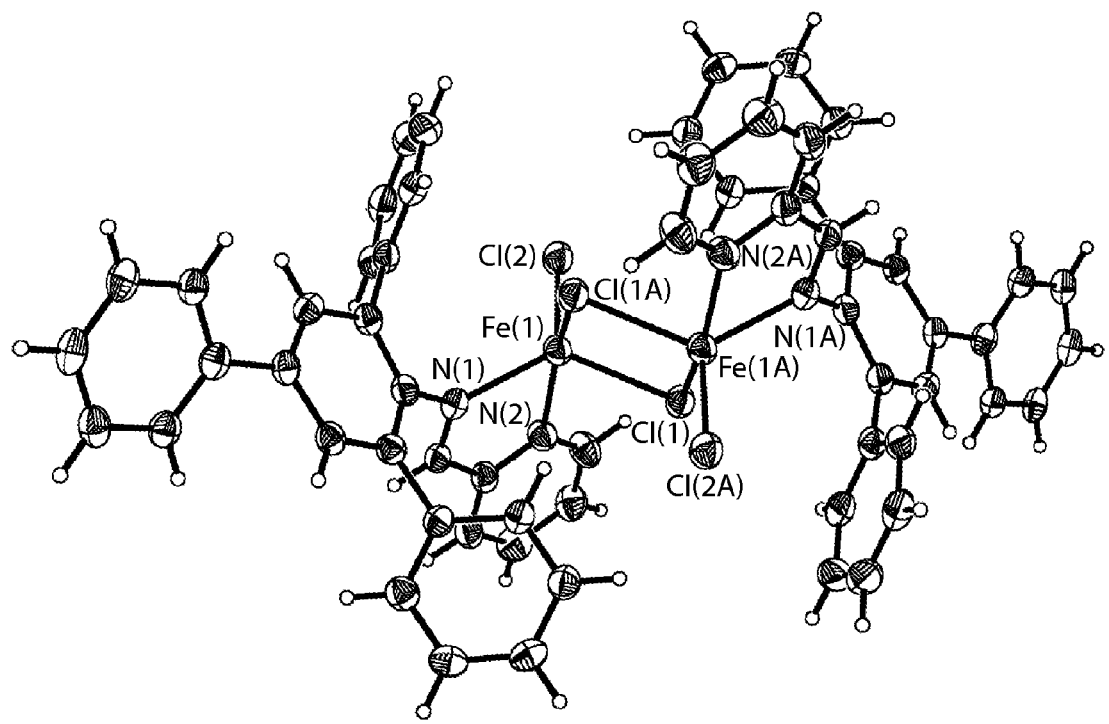
FIG. 6 depicts the X-ray structure of (E)-3,5-diphenyl-N-(pyridin-2-ylmethylene)biphenyl-2-amine iron(II) chloride with hydrogens and with the atom labeling scheme employed for heteroatoms. The nonhydrogen atoms are depicted with 50% probability ellipsoids.
Figure 7:
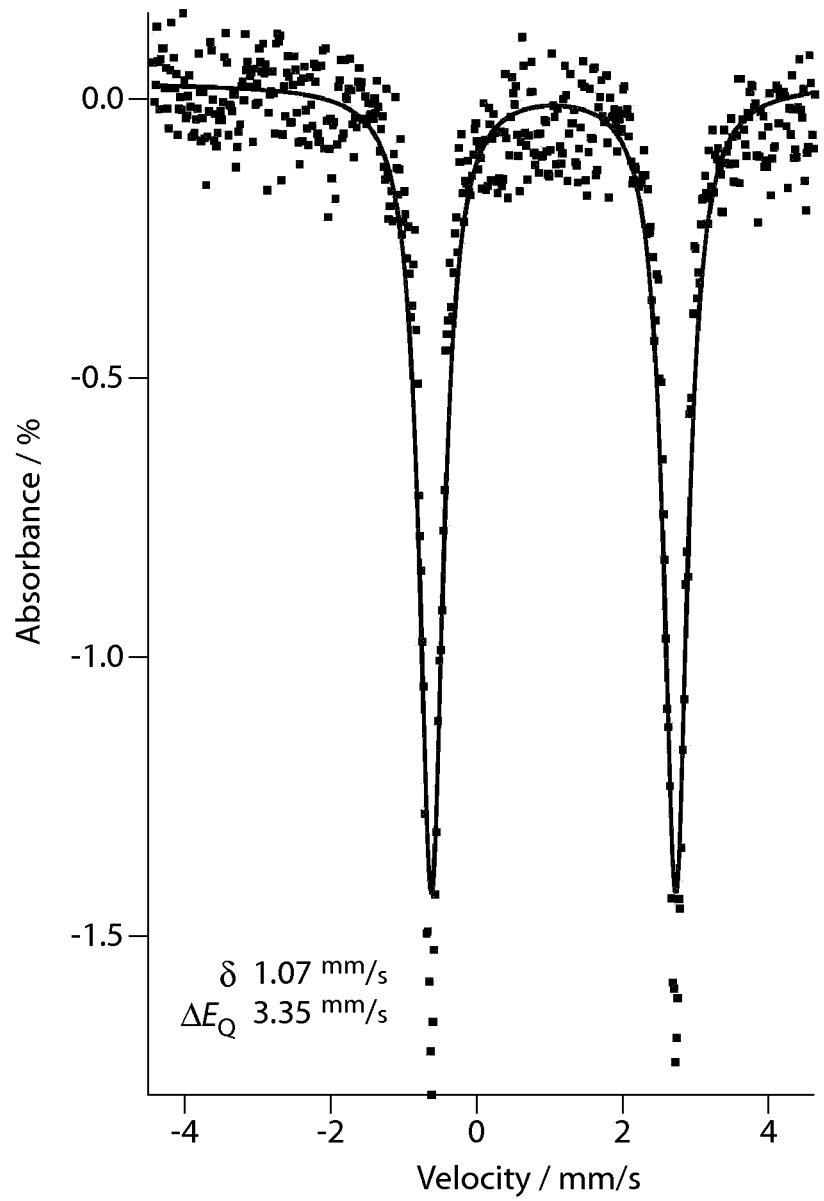
FIG. 7 depicts the Mössbauer spectrum of (E)-3,5-diphenyl-N-(pyridin-2-ylmethylene)biphenyl-2-amine iron(II) chloride at 90 K.

X-Ray data: The title compound crystallized as green needles from a vapor diffusion of diethyl ether into a CH$_2$Cl$_2$ solution at −35° C. Crystal data as well as details of data collection and refinement are summarized in Table 1. Ortep plot is provided in FIG. 6.

TABLE 1

| | |
|---|---|
| Identification code | CCDC 853131 |
| Chemical formula | C$_{60}$H$_{44}$Cl$_4$Fe$_2$N$_4$ |
| M$_r$ | 1074.49 |
| Crystal system, space group | Orthorhombic, Pccn |
| Temperature (K) | 100 |
| a, b, c (Å) | 19.6880 (16), 28.115 (2), 10.4622 (9) |
| V (Å$^3$) | 5791.2 (8) |
| Z | 4 |
| Radiation type | Cu Kα |
| μ (mm$^{-1}$) | 6.01 |
| Crystal size (mm) | 0.05 × 0.01 × 0.01 |
| Diffractometer | Bruker D8 goniometer with CCD area detector diffractometer |
| Absorption correction | Multi-scan, SADABS (Sheldrick, 2008) |
| T$_{min}$, T$_{max}$ | 0.753, 0.942 |
| No. of measured, independent and observed [I > 2σ(I)] reflections | 69244, 5053, 3940 |
| R$_{int}$ | 0.131 |
| R[F$^2$ > 2σ(F$^2$)], wR(F$^2$), S | 0.062, 0.151, 1.10 |
| No. of reflections | 5053 |
| No. of parameters | 316 |
| No. of restraints | 0 |
| H-atom treatment | H-atom parameters constrained |
| Δρ$_{max}$, Δρ$_{min}$ (e Å$^{-3}$) | 0.92, −0.50 |

Iron-(L-97) Complex

Synthesis of Fe(II)chloride complex, (E)-2,4,4-Trimethyl-N-(pyridin-2-ylmethylene)pentan-2-amine Iron(II) Chloride, from ligand (L-97)

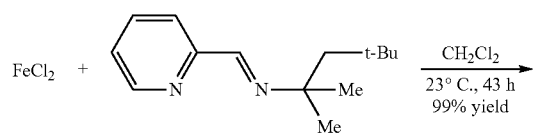

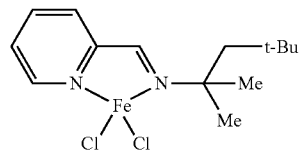

A solution of (E)-2,4,4-trimethyl-N-(pyridin-2-ylmethylene)propan-2-amine (L-97) (0.300 g, 1.37 mmol, 1.00 equiv) in CH$_2$Cl$_2$ (8 mL) was added to iron(II) chloride (174 mg, 1.37 mmol, 1.00 equiv). The reaction mixture was stirred at 23° C. for 43 h. The reaction mixture was filtered over a celite pad, eluting with CH$_2$Cl$_2$, and concentrated under reduced pressure. The residue was washed with Et$_2$O (2×5 mL) and dried under reduced pressure to afford the title compound as an orange solid (0.471 g, 99% yield). X-Ray quality crystals were grown from vapor diffusion of pentane into a solution of the title compound in CH$_2$Cl$_2$ at 23° C.

Magnetic susceptibility (500 MHz, CD$_2$Cl$_2$): $\mu_{eff}$=5.45$\mu_B$ (8.43 mg/mL). NMR Spectroscopy: $^1$H NMR (500 MHz, CD$_2$Cl$_2$, 25° C., δ): 82.92 ($\Delta v_{1/2}$=258 Hz), 64.16 ($\Delta v_{1/2}$=702 Hz), 57.30 ($\Delta v_{1/2}$=77 Hz), 52.50 ($\Delta v_{1/2}$=61 Hz), 3.23 ($\Delta v_{1/2}$=82 Hz), 15.99 ($\Delta v_{1/2}$=334 Hz), 17.94 ($\Delta v_{1/2}$=39 Hz), 24.21 ($\Delta v_{1/2}$=550 Hz). $^{13}$C NMR (125 MHz, CD$_2$Cl$_2$, 25° C., δ): 298.8 ($\Delta v_{1/2}$=296 Hz), 246.7 ($\Delta v_{1/2}$=89 Hz), 245.4 ($\Delta v_{1/2}$=84 Hz), 142.6 ($\Delta v_{1/2}$=97 Hz), 111.7 ($\Delta v_{1/2}$=252 Hz), 107.5 ($\Delta v_{1/2}$=208 Hz), 78.5 ($\Delta v_{1/2}$=153 Hz), 36.6 ($\Delta v_{1/2}$=143 Hz), 29.6 ($\Delta v_{1/2}$=187 Hz), 27.4 ($\Delta v_{1/2}$=78 Hz), 17.5 ($\Delta v_{1/2}$=29 Hz). Mössbauer Spectroscopy (95 K): δ=0.9 mm/s, $\Delta E_Q$=2.8 mm/s. Anal Calcd for C$_{14}$H$_{22}$Cl$_2$FeN$_2$: C, 48.73; H, 6.43; N, 8.12. Found: C, 48.81; H, 6.15; N, 8.00.

Figure 8:
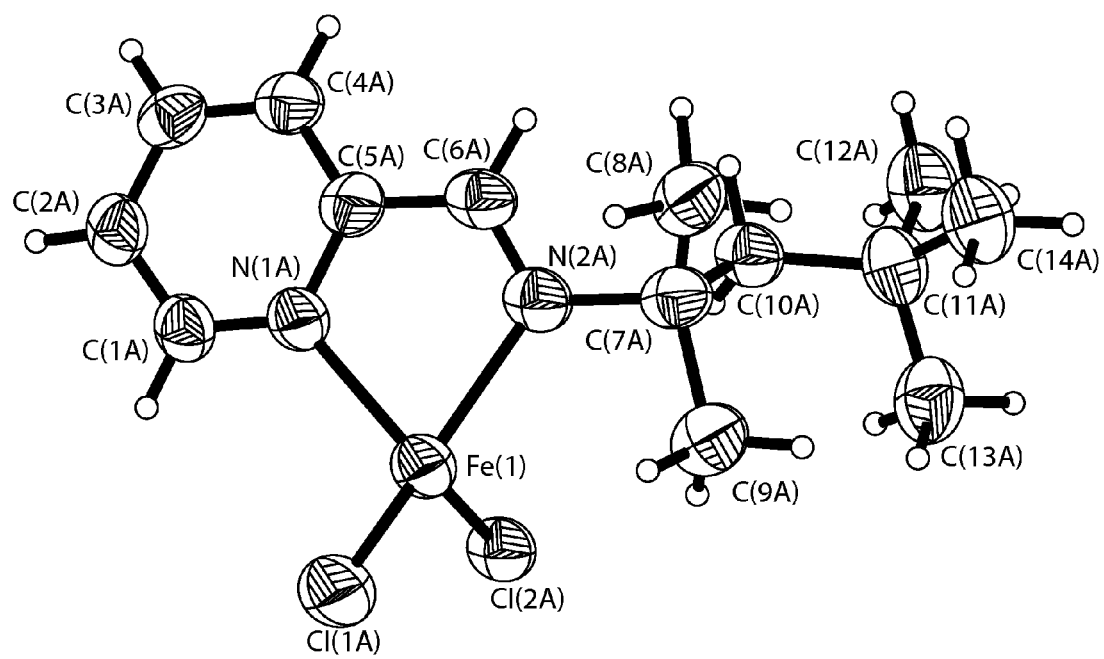
FIG. 8 depicts the X-ray structure of (E)-2,4,4-trimethyl-N-(pyridin-2-ylmethylene)pentan-2-amine iron(II) chloride with hydrogens and with the atom labeling scheme employed. The nonhydrogen atoms are depicted with 50% probability ellipsoids.
Figure 9:
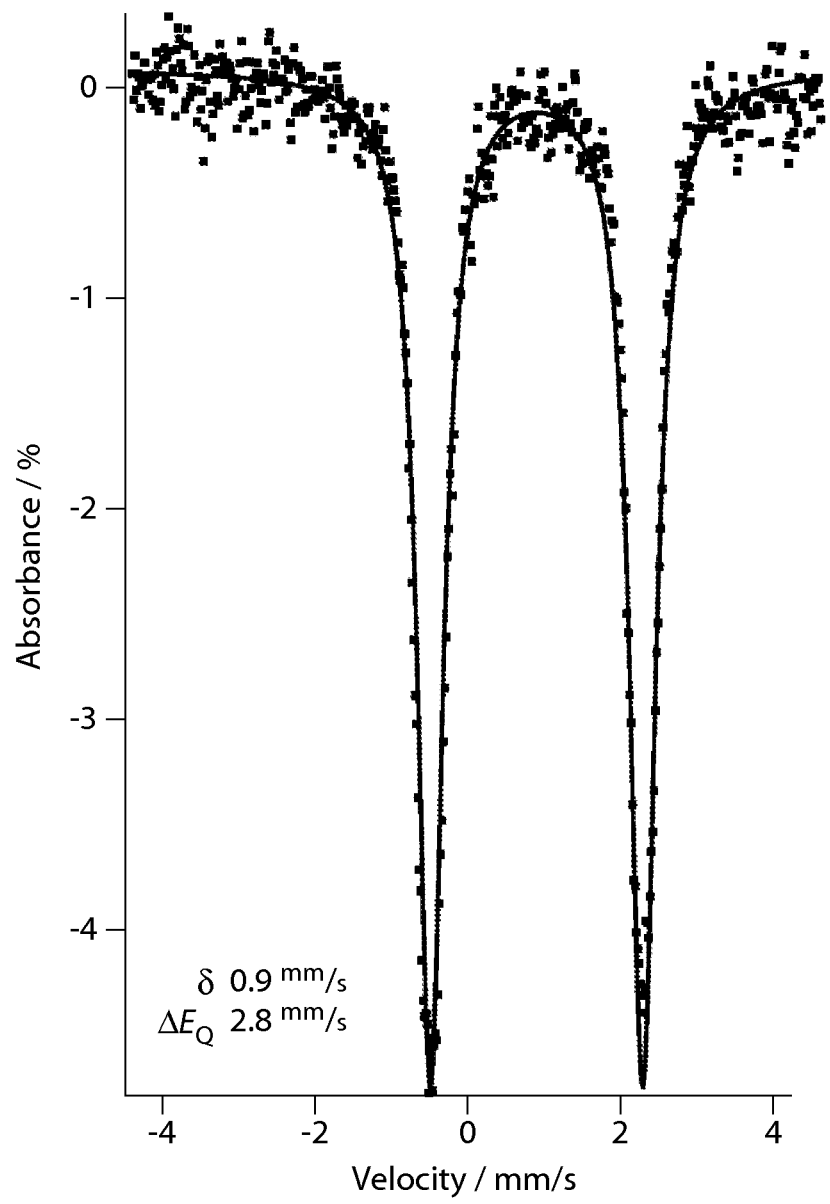
FIG. 9 depicts the Mössbauer spectrum of (E)-2,4,4-trimethyl-N-(pyridin-2-ylmethylene)pentan-2-amine iron(II) chloride at 90 K.

X-Ray data. The title compound crystallized as orange plates from a vapor diffusion of pentane into a CH$_2$Cl$_2$ solution at 23° C. Crystal data as well as details of data collection and refinement are summarized in Table 2. Ortep plot is provided in FIG. 8.

TABLE 2

| | |
|---|---|
| Identification code | CCDC 853130 |
| Chemical formula | C$_{14}$H$_{22}$Cl$_2$FeN$_2$ |
| Molecular weight | 345.09 |
| Crystal system, space group | Triclinic, P-1 |
| Temperature (K) | 100 |
| a, b, c (Å) | 8.0412 (4), 12.8066 (7), 16.8314 (10) |
| α, β, γ (°) | 99.106 (3), 97.796 (3), 97.609 (4) |
| V (Å$^3$) | 1674.53 (16) |
| Z | 4 |
| Radiation type | Cu Kα |
| μ (mm$^{-1}$) | 10.06 |
| Crystal size (mm) | 0.10 × 0.05 × 0.01 |
| Diffractometer | Bruker D8 goniometer with CCD area detector diffractometer |
| Absorption correction | Multi-scan, SADABS (Sheldrick, 2008) |
| T$_{min}$, T$_{max}$ | 0.036, 0.633 |
| No. of measured, independent and observed [I > 2σ(I)] reflections | 26716, 5572, 3897 |
| R$_{int}$ | 0.085 |
| R[F$^2$ > 2σ(F$^2$)], wR(F$^2$), S | 0.079, 0.204, 1.07 |
| No. of reflections | 5572 |
| No. of parameters | 353 |
| No. of restraints | 0 |
| H-atom treatment | H-atom parameters constrained |
| Δρ$_{max}$, Δρ$_{min}$ (e Å$^{-3}$) | 1.12, −0.62 |

General Polymerization Methods
Polymerization Method I

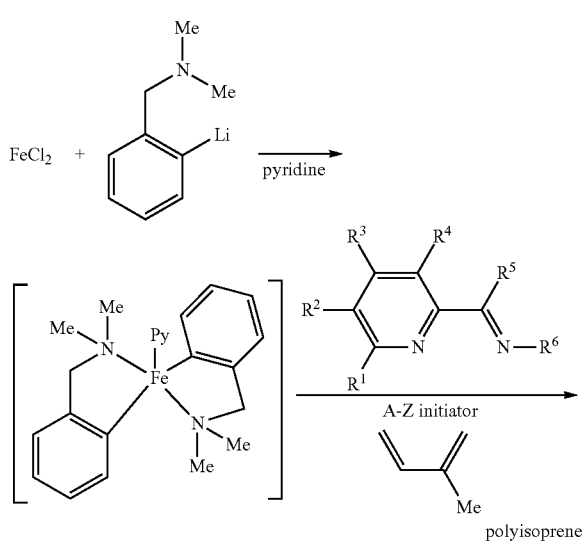

polyisoprene

Generation of a precatalyst from $FeCl_2$, pyridine, n-BuLi, and N,N-dimethylbenzylamine (i.e., to provide [2-(N,N-dimethylaminomethyl)phenyl]lithium) is described in Wu et al., J. Am. Chem. Soc. (2010) 132:13214-13216, incorporated herein by reference in its entirety.

To a 20 mL scintillation vial is added the precatalyst (10.0 mg, 24.8 µmol) and THF (1 mL). To this precatalyst mixture is added 1 equivalent (24.8 µmol) of a ligand in THF. The reaction mixture is stirred for approximately 3 to 5 minutes, and then 1 equiv. of an initiator is added to the solution. The mixture was again stirred for 3 to 5 minutes. Isoprene (monomer) is added (100 to 10,000 equivalents), and the polymerization is allowed to proceed for 24 to 48 hours at room temperature.

Polymerization Method II

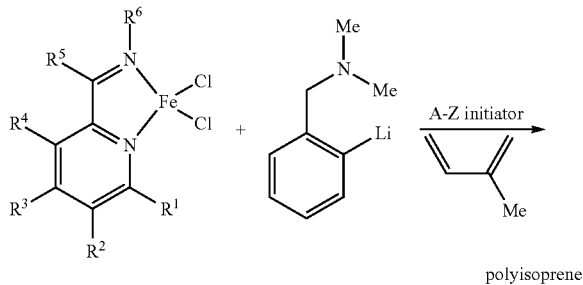

polyisoprene

To a $N_2$-filled inert atmosphere box, a vial is charged with the Fe(II)chloride complex (0.25 mol %). To the vial is added [2-(N,N-dimethylaminomethyl)phenyl]lithium (0.50 mol %) in 1.5 mL THF. The reaction mixture is allowed to mix for 2 minutes in order to form a precatalyst.

To the reaction mixture of the precatalyst, an initiator (0.42 mol %) in 1.5 mL THF is added. The reaction mixture is allowed to mix for about 15 minutes and then isoprene (monomer) is added (1 equiv.) and the polymerization is allowed to proceed for 65 to 75 hours at room temperature. Reactions are conducted with 1.00 g (14.7 mmol) of isoprene in 3 mL THF and 0.25 mol % catalyst.

Polymerization Method III

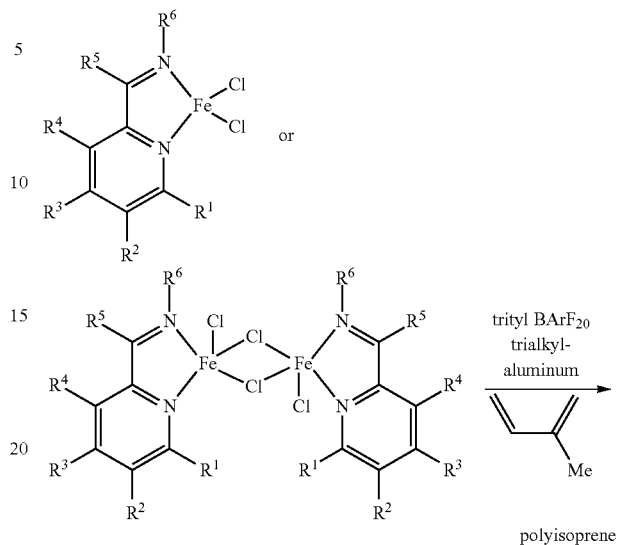

polyisoprene

Standard polymerization conditions involve the use of a trialkylaluminum derivative as alkylating reagent (e.g., triisobutylaluminum, triethylaluminum) and of trityl tetrakis (pentafluorophenyl)borate (trityl $BArF_{201}$=$Ph_3C$ $B(C_6F_5)_4$) as de-alkylating reagent in apolar solvents for less than 5 hours. Typical ratio: [Fe]/[Al]/[trityl $BArF_{20}$]/[isoprene]=1/3/1/1000-5000. Solvent: toluene, methylcyclohexane, heptane, or mixture thereof.

To a 20 mL scintillation vial was added the iminopyridine-based Fe(II)chloride complex (9.3 µmol) and 2-3 mL of toluene (or heptane or Me-cyclohexane), followed by 3 equivalents (27.9 µmol) of triisobutylaluminum as a solution in 1 mL toluene (or heptane or Me-cyclohexane). The reaction mixture was allowed to stir for 2-5 minutes. To this reaction mixture was added 1 equivalent (8.6 mg, 9.3 µmol) of trityl tetrakis(pentafluorophenyl)borate as a solution in 2 mL toluene (or as a dispersion in heptane or Me-cyclohexane). The reaction mixture was allowed to stir for 2-5 minutes and isoprene was added (10-50 mmol). The reaction mixture was allowed to stir for 2-5 hours at 23° C., or at a temperature ranging from −100 to 50° C. The reaction mixture was quenched with DCM (10 mL) from the squirtbottle. The polymer polyisoprene (PI) was obtained by precipitation in cold methanol to yield a white chewing gum (quantitative).

Characterization of Polyisoprene

The microstructure of the polyisoprene can be analyzed by $^1H$ and $^{13}C$ NMR spectroscopy after filtration (to remove the iron residue) and concentration in vacuo. For high molecular masses, the polyisoprene is precipitated twice in methanol prior to analysis.

Spectroscopy for polystyrene generated: $^1H$ NMR (500 MHz, $CDCl_3$, 23° C., δ, relaxation time 10 s): olefinic H atoms for 1,4-motif: 5.12 (s, $\Delta v_{1/2}$=35-50 Hz, 1H); 3,4-motif: 4.73 (d, br, J~20 Hz, 1H), 4.66 (d, br, J~20 Hz, 1H); aliphatic H atoms for 1,4-motif: 2.07 (s, br, 2H), 1.99 (d, br, J~5 Hz, 2H), 1.60 (s, 3H), 3,4-motif: 2.20 (s, br, 2H), 1.86 (m, br, 2H), 1.68 (s, br, 3H). $^{13}C$ NMR (125 MHz, $CDCl_3$, 25° C., δ, relaxation time 5 s): olefinic C atoms for 1,4-motif: 135.1, 124.4; 3,4-motif: 147.8, 111.4, aliphatic C atoms for trans-1,4-motif: 39.9, 26.9, 16.2; for cis-1,4-motif: 30.8, 28.5 (m), 26.1 (m), 23.7; 3,4-motif: 45.0 (m), 37.6 (m), 32.3 (m), 18.5

(m) (or 3,4-motif: 45.4 (m), 36.8 (m), 33.2 (m), 18.5 (m)). SEC chromatography (eluent: THF, Polystyrene standards, RI detection, 3-column set).

The polymer number-average molar mass ($M_n$) and corresponding dispersity (D) of the prepared polyisoprenes were determined by size exclusion chromatography (SEC) (a.k.a. gel permeation chromatography) equipped with a UV detector at 212 nm, and a refractive index detector, using THF as eluent, and polystyrene (PS) standards for calibration. A correction factor was applied to account for the difference in hydrodynamic volumes between identical molar mass of PS and PI.

The following equations were used to determine selectivities:

$$[\%1,4\text{-motif}] = \frac{A(CH=CMe\text{-}1,4\text{-motif})}{A(CH=CMe\text{-}1,4\text{-motif}) + \frac{A(CH_2=CMe\text{-}3,4\text{-motif})}{2}}$$

$$[\%1,4\text{-motif}] = \frac{A(5.12\text{ ppm})}{A(5.12\text{ ppm}) + \frac{A(4.5-4.9\text{ ppm})}{2}}$$

$$[\% \text{ trans-}1,4\text{-motif}] =$$
$$\frac{A(CH_3\text{-}trans\text{-}1,4\text{-motif})}{A(CH_3\text{-}trans\text{-}1,4\text{-motif}) + A(CH_3\text{-}cis\text{-}1,4\text{-motif})}$$

$$[\% \text{ trans-}1,4\text{-motif}] = \frac{A(16.2\text{ ppm})}{A(16.2\text{ ppm}) + A(23.7\text{ ppm})}$$

$$[\% \text{ cis-}1,4\text{-motif}] =$$
$$\frac{A(CH_3\text{-}cis\text{-}1,4\text{-motif})}{A(CH_3\text{-}cis\text{-}1,4\text{-motif}) + A(CH_3\text{-}trans\text{-}1,4\text{-motif})}$$

$$[\% \text{ cis-}1,4\text{-motif}] = \frac{A(23.7\text{ ppm})}{A(23.7\text{ ppm}) + A(16.2\text{ ppm})}$$

Polymerization Example 1

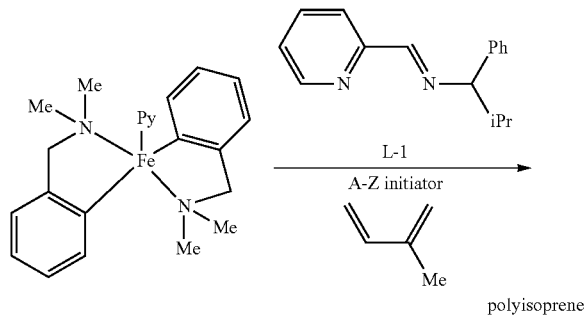

Following General Method I.

To a 20 mL scintillation vial was added the precatalyst (10.0 mg, 24.8 µmol) and THF (1 mL), followed by 1 equivalent (24.8 µmol) of an iminopyridine ligand (L-1) in THF. The reaction mixture was stirred for 3 to 5 min. To this reaction mixture was added 1 equiv. of dimethyl(phenyl)(4,4,5,5-tetramethyl-1,3,2-dioxaborolan-2-yl)silane was then added to the solution. The initiating mixture was again stirred for 3 to 5 min. Isoprene was added (100-10,000 equiv.) and the polymerization was allowed to proceed for 24 hours at room temperature to provide the polyisoprene (PI) as a brown viscous oil, 30% yield. Number average molar mass (Mn) (as determined by SEC): Mn=55,000 g/mol; Dispersity (as determined by SEC)=1.8.

| Example 1 PI microstructure | | | |
|---|---|---|---|
| 1,4-cis-PI (%) | 1,4-trans-PI (%) | 3,4-PI (%) | 1,2-PI (%) |
| 70 | <1 | 29 | None detected |

Polymerization Example 2

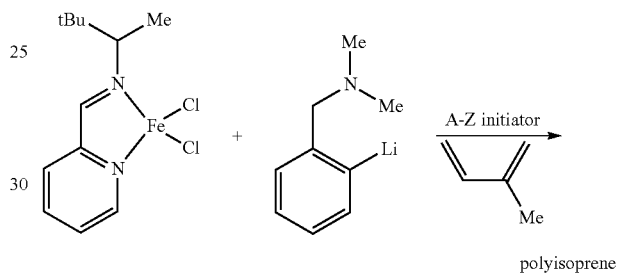

Following General Method II.

To a 20 mL scintillation vial was added the (L-4)-Fe(II) chloride complex (11.8 mg, 37.2 µmol), followed by 2 equivalents (10.5 mg, 74.4 µmol) of (2-((dimethylamino)methyl)-phenyl)lithium as a solution in 1.5 mL THF. The reaction mixture was allowed to mix for 2 minutes. Following the above described General Method, to the reaction mixture of precatalyst (2a), 0.42 mol % of hexamethyldisilane in 1.5 mL THF was added. The reaction mixture was allowed to mix for about 15 minutes and isoprene was added (100-10,000 equiv.). The reaction mixture was allowed to mix for 68 hours at 23° C. The reaction mixture was concentrated and the residue dissolved in wet THF (5 mL). The mixture was filtered through a 0.45 µm PTFE Acrodisc syringe filter and concentrated to give the polyisoprene (PI) as a light yellow oil (35% yield).

| Example 2 PI microstructure | | | |
|---|---|---|---|
| 1,4-cis-PI (%) | 1,4-trans-PI (%) | 3,4-PI (%) | 1,2-PI (%) |
| 90 | 2 | 8 | None detected |

Polymerization Example 3

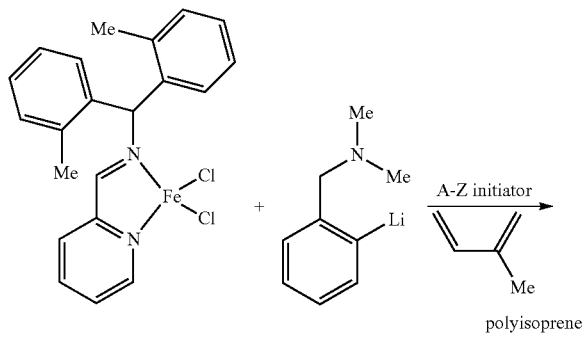

Following General Method II.

To a 20 mL scintillation vial was added the (L-3)-Fe(II) chloride complex (15.9 mg, 37.2 μmol), followed by 2 equivalents (10.5 mg, 74.4 μmol) of (2-((dimethylamino)methyl)-phenyl)lithium as a solution in 1.5 mL THF. The reaction mixture was allowed to mix for 2 minutes. To this reaction mixture 0.42 mol % of hexamethyldisilane in 1.5 mL THF was added. The reaction mixture was allowed to mix for about 15 minutes and isoprene was added (1 equivalent). The reaction mixture was allowed to mix for 68 hours at 23° C. The reaction mixture was concentrated and the residue dissolved in wet THF (5 mL). The mixture was filed through a 0.45 μm PTFE Acrodisc syringe filter and concentrated to give the polyisoprene (PI) as a translucent brown oil (0.638 g, 64% yield).

| Example 3 PI microstructure | | | |
|---|---|---|---|
| 1,4-cis-PI (%) | 1,4-trans-PI (%) | 3,4-PI (%) | 1,2-PI (%) |
| 96 | 2.5 | 1.5 | None detected |

Polymerization Example 4

(trans-1,4-Polyisoprene (in Toluene))

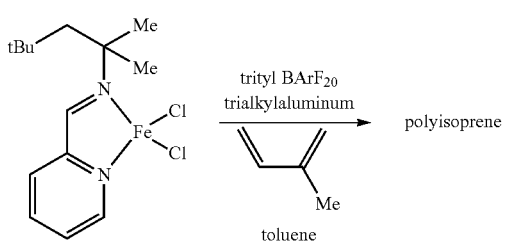

Following General Method III.

To a 20 mL scintillation vial was added (E)-2,4,4-trimethyl-N-(pyridin-2-ylmethylene)pentyl-2-amine (or tert-octyl-iminopyridine) iron(II) chloride complex (3.2 mg, 9.3 μmol, 1.0 equiv) and 2 mL of toluene, followed by triisobutylaluminum (5.5 mg, 28 μmol, 3.0 equiv) in 1 mL toluene at 23° C. The reaction mixture was stirred for 2 min and trityl tetrakis(pentafluorophenyl)borate (8.6 mg, 9.3 μmol, 1.0 equiv) was added as a solution in 2 mL toluene at 23° C. The reaction mixture was stirred for 2 min and isoprene (0.681 g, 1.00 mL, 10.0 mmol, 1.08×10³ equiv) was added. The reaction mixture was stirred for 2 hours at 23° C. The reaction mixture was quenched by opening to air and diluting with DCM from the squirtbottle (10 mL). The title compound was isolated by precipitation in cold methanol to yield a colorless gum (yield >99% 700 mg).

NMR Spectroscopy: $^1$H NMR (500 MHz, CDCl$_3$, 23° C., δ, relaxation time 10 s): olefinic H atoms for 1,4-motif: 5.12 (s, Δv$_{1/2}$=35 Hz, 1H); 3,4-motif: 4.73 (d, b, J~20 Hz, 1H), 4.66 (d, b, J~20 Hz, 1H); aliphatic H atoms for 1,4-motif: 2.07 (s, b, 2H), 1.99 (d, b, J~5 Hz, 2H), 1.60 (s, 3H), 3,4-motif: 2.20 (s, b, 2H), 1.86 (m, b, 2H), 1.68 (s, b, 3H). $^{13}$C NMR (125 MHz, CDCl$_3$, 25° C., δ, relaxation time 5 s): olefinic C atoms for 1,4-motif: 135.1, 124.4; 3,4-motif: 147.8, 111.4, aliphatic C atoms for 1,4-motif: 39.9, 26.9, 16.2; 3,4-motif: 45.0 (m), 37.6 (m), 32.3 (m), 18.5 (m). SEC chromatography (eluent: THF, Polystyrene standards): $M_w$=125,000 g/mol, D=2.0. Selectivity: 1,4/3,4=12:1 and trans-1,4/cis-1,4>99:1 (92% of trans-1,4-polyisoprene in the bulk).

| Example 4 PI microstructure | | | |
|---|---|---|---|
| 1,4-cis-PI (%) | 1,4-trans-PI (%) | 3,4-PI (%) | 1,2-PI (%) |
| <1 | 92 | 7-8 | None detected |

Polymerization Example 5 trans-1,4-Polyisoprene (in Me-cyclohexane/Toluene 5:1)

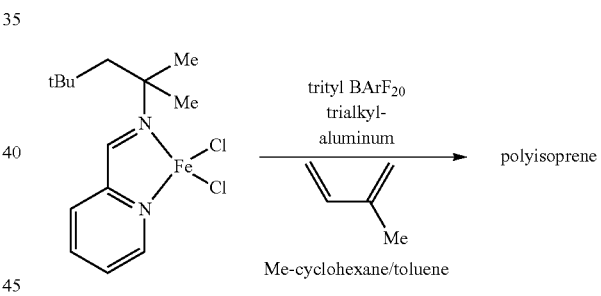

Following General Method III.

To a 20 mL scintillation vial was added (E)-2,4,4-trimethyl-N-(pyridin-2-ylmethylene)pentyl-2-amine (or tert-octyl-iminopyridine) iron(II) chloride complex (3.2 mg, 9.3 μmol, 1.0 equiv) and 5 mL of Me-cyclohexane, followed by triisobutylaluminum (5.5 mg, 28 μmol, 3.0 equiv) in 1 mL of Me-cyclohexane at 23° C. The reaction mixture was stirred for 2 min and trityl tetrakis(pentafluorophenyl)borate (8.6 mg, 9.3 μmol, 1.0 equiv) was added as a solution in 3 mL of a 1:1 mixture of Me-cyclohexane and toluene at 23° C. The reaction mixture was stirred for 2 min and isoprene (1.362 g, 2.00 mL, 20.0 mmol, 2.15×10³ equiv) was added. The reaction mixture was stirred for 4 hours at 23° C. The reaction mixture was quenched by opening to air and diluting with DCM from the squirtbottle (10 mL). The title compound was isolated by precipitation in cold methanol to yield a colorless gum (yield >99% 1.4 g). NMR Spectroscopy: NMR (500 MHz, CDCl$_3$, 23° C., δ, relaxation time 10 s): olefinic H atoms for 1,4-motif: 5.12 (s, Δv$_{1/2}$=50 Hz, 1H); 3,4-motif: 4.73 (d, b, 1H), 4.66 (d, b, 1H); aliphatic H atoms for 1,4-motif: 2.07 (s, b, 2H), 1.99 (d, b, J~5 Hz, 2H), 1.60 (s, 3H), 3,4-motif: 2.20 (s, b, 2H), 1.86 (m, b, 2H), 1.68 (s, b, 3H). $^{13}$C NMR (125 MHz, CDCl$_3$, 25° C., δ, relaxation time 5 s): olefinic C atoms for 1,4-motif: 135.1, 124.4; 3,4-motif: 147.8, 111.4, aliphatic C atoms for 1,4-motif: 39.9, 26.9, 16.2; 3,4-motif: 45.0 (m), 37.6 (m), 32.3 (m), 18.5 (m). SEC chromatography (eluent: THF, Polystyrene standards): M$_w$=600,000 g/mol, D=2.5. Selectivity: 1,4/3,4>12:1 and trans-1,4/cis-1,4>99:1 (93% of trans-1,4-polyisoprene in the bulk).

| Example 5 PI microstructure | | | |
|---|---|---|---|
| 1,4-cis-PI (%) | 1,4-trans-PI (%) | 3,4-PI (%) | 1,2-PI (%) |
| <1 | 93 | 7 | None detected |

Polymerization Example 6 trans-1,4-Polyisoprene (in Heptane/Toluene 5:1)

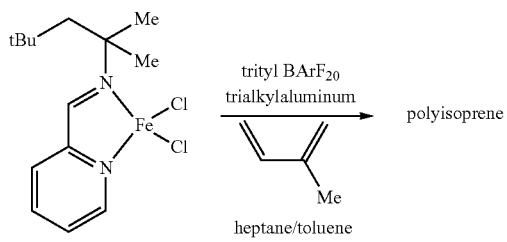

To a 20 mL scintillation vial was added (E)-2,4,4-trimethyl-N-(pyridin-2-ylmethylene)pentyl-2-amine (or tert-octyl-iminopyridine) iron(II) chloride complex (3.2 mg, 9.3 µmol, 1.0 equiv) and 5 mL of heptane, followed by triisobutylaluminum (5.5 mg, 28 µmol, 3.0 equiv) in 1 mL of heptane at 23° C. The reaction mixture was stirred for 2 min and trityl tetrakis(pentafluorophenyl)borate (8.6 mg, 9.3 µmol, 1.0 equiv) was added as a solution in 3 mL of a 1:1 mixture of heptane and toluene at 23° C. The reaction mixture was stirred for 2 min and isoprene (1.362 g, 2.00 mL, 20.0 mmol, 2.15× 10$^3$ equiv) was added. The reaction mixture was stirred for 4 hours at 23° C. The reaction mixture was quenched by opening to air and diluting with DCM from the squirtbottle (10 mL). The title compound was isolated by precipitation in cold methanol to yield a colorless gum (yield >99% 1.4 g). NMR Spectroscopy: $^1$H NMR (500 MHz, CDCl$_3$, 23° C., δ, relaxation time 10 s): olefinic H atoms for 1,4-motif: 5.12 (s, Δν$_{1/2}$=45 Hz, 1H); 3,4-motif: 4.73 (d, b, 1H), 4.66 (d, b, 1H); aliphatic H atoms for 1,4-motif: 2.07 (s, b, 2H), 1.99 (d, b, J~5 Hz, 2H), 1.60 (s, 3H), 3,4-motif: 2.20 (s, b, 2H), 1.86 (m, b, 2H), 1.68 (s, b, 3H). $^{13}$C NMR (125 MHz, CDCl$_3$, 25° C., δ, relaxation time 5 s): olefinic C atoms for 1,4-motif: 135.1, 124.4; 3,4-motif: 147.8, 111.4, aliphatic C atoms for 1,4-motif: 39.9, 26.9, 16.2; 3,4-motif: 45.0 (m), 37.6 (m), 32.3 (m), 18.5 (m). SEC chromatography (eluent: THF, Polystyrene standards): M$_w$=600,000 g/mol, D=2.5. Selectivity: 1,4/3,4>12:1 and trans-1,4/cis-1,4>99:1 (92.5% of trans-1,4-polyisoprene in the bulk).

| Example 6 PI microstructure | | | |
|---|---|---|---|
| 1,4-cis-PI (%) | 1,4-trans-PI (%) | 3,4-PI (%) | 1,2-PI (%) |
| <1 | 92.5 | 7.5 | None detected |

Polymerization Example 7 trans-1,4-Polyisoprene (10 g Scale)

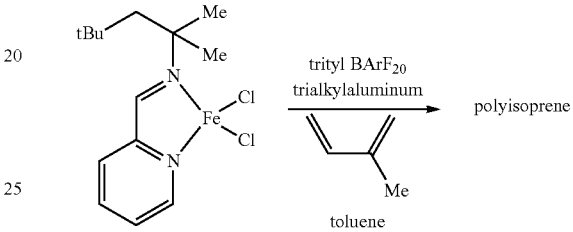

To a 500 mL round-bottom flask was added (E)-2,4,4-trimethyl-N-(pyridin-2-ylmethylene)pentyl-2-amine (or tert-octyl-iminopyridine) iron(II) chloride complex (9.6 mg, 28 lima 1.0 equiv) and 10 mL of toluene, followed by triisobutylaluminum (16.5 mg, 84 µmol, 3.0 equiv) in 5 mL toluene at 23° C. The reaction mixture was stirred for 3 min and trityl tetrakis(pentafluorophenyl)borate (25.8 mg, 28 µmol, 1.0 equiv) was added as a solution in 5 mL toluene at 23° C. The reaction mixture was stirred for 2 min and 50 mL of Me-cyclohexane was added to bring the total volume to 70 mL, and then isoprene (10.0 g, 14.7 mL, 147 mmol, 5.25×10$^3$ equiv) was added. The reaction mixture was stirred for 5 hours at 23° C. The reaction mixture was quenched by opening to air and diluting with DCM from the squirtbottle (50 mL). The title compound was isolated by precipitation in cold methanol to yield a colorless gum (yield >99% 10.1 g after drying overnight under vacuum). NMR Spectroscopy: $^1$H NMR (500 MHz, CDCl$_3$, 23° C., δ, relaxation time 10 s): olefinic protons for 1,4-motif: 5.12 (s, 1H, Δν$_{1/2}$=45 Hz); 3,4-motif: 4.73 (d, b, 1H), 4.66 (d, b, 1H); aliphatic protons for 1,4-motif: 2.07 (s, b, 2H), 1.99 (d, b, J~5 Hz, 2H), 1.60 (s, 3H), 3,4-motif: 2.20 (s, b, 2H), 1.86 (m, b, 2H), 1.68 (s, b, 3H). $^{13}$C NMR (125 MHz, CDCl$_3$, 25° C., δ, relaxation time 5 s): olefinic carbons for 1,4-motif: 135.1, 124.4; 3,4-motif: 147.8, 111.4, aliphatic carbons for 1,4-motif: 39.9, 26.9, 16.2; 3,4-motif: 45.0 (m), 37.6 (m), 32.3 (m), 18.5 (m). SEC chromatography (eluent: THF, Polystyrene standards): M$_w$=650,000 g/mol, D=3.9. Selectivity 1,4/3,4=12:1 and trans-1,4/cis-1,4>99:1 (92.5% of trans-1,4-polyisoprene in the bulk).

| Example 7 PI microstructure | | | |
|---|---|---|---|
| 1,4-cis-PI (%) | 1,4-trans-PI (%) | 3,4-PI (%) | 1,2-PI (%) |
| <1 | 92.5 | 7.5 | None detected |

Polymerization Example 8 cis-1,4-Polyisoprene (in Toluene)

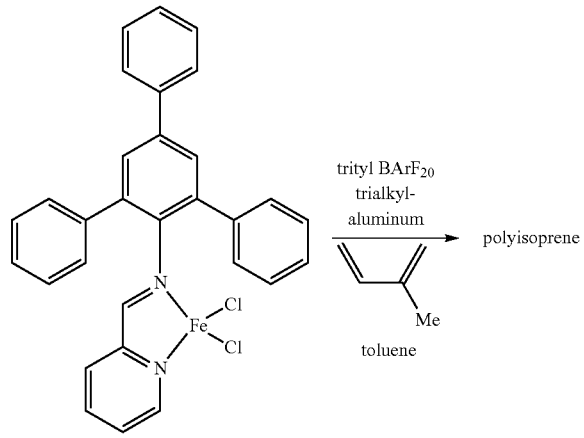

To a 20 mL scintillation vial was added (E)-2,4,6-triphenyl-N-(pyridin-2-ylmethylene)aniline (or supermesityl-iminopyridine) iron(II) chloride complex (5.0 mg, 9.3 µmol, 1.0 equiv) and 2 mL of toluene, followed by triethylaluminum (3.2 mg, 28 µmol, 3.0 equiv) in 1 mL toluene at 23° C. The reaction mixture was stirred for 2 min and trityl tetrakis(pentafluorophenyl)borate (8.6 mg, 9.3 µmol, 1.0 equiv) was added as a solution in 2 mL toluene at 23° C. The reaction mixture was stirred for 5 min at −78° C. and cold isoprene (0.681 g, 1.00 mL, 10.0 mmol, 1.08×10$^3$ equiv) was added. The reaction mixture was stirred for 4 hours at −78° C. The reaction mixture was quenched by opening to air and diluting with DCM from the squirtbottle (10 mL). The title compound was isolated by precipitation in cold methanol to yield a colorless gum (yield >99% 700 mg). NMR Spectroscopy: $^1$H NMR (500 MHz, CDCl$_3$, 23° C., δ): olefinic H atoms for 1,4-motif: 5.12 (s, 1H, $\Delta v_{1/2}$=50 Hz); 3,4-motif: 4.72 (br, 1H), 4.68 (br, 1H); aliphatic H atoms for 1,4-motif: 2.03 (br, 4H), 1.70 (s, 3H), 3,4-motif: 2.22 (br, 1H), 1.80 (m, b, 2H), 1.32 (s, b, 3H). $^{13}$C NMR (125 MHz, CDCl$_3$, 25° C., δ): olefinic C atoms for 1,4-motif: 135.6 (m), 134.0 (m), 126.5 (m), 125.3 (m); 3,4-motif: 147.7, 111.5, aliphatic C atoms for 1,4-motif: 30.8, 28.5 (m), 26.1 (m), 23.7; 3,4-motif: 45.4 (m), 36.8 (m), 33.2 (m), 18.5 (m). SEC chromatography (eluent: THF, Polystyrene standards): $M_w$=140,000 g/mol, D=1.7. Selectivity 1,4/3,4=6:1 and cis-1,4/trans-1,4>99:1 (85% of cis-1,4-polyisoprene in the bulk).

Polymerization Example 9 cis-1,4-Polyisoprene (in Me-cyclohexane at Room Temperature)

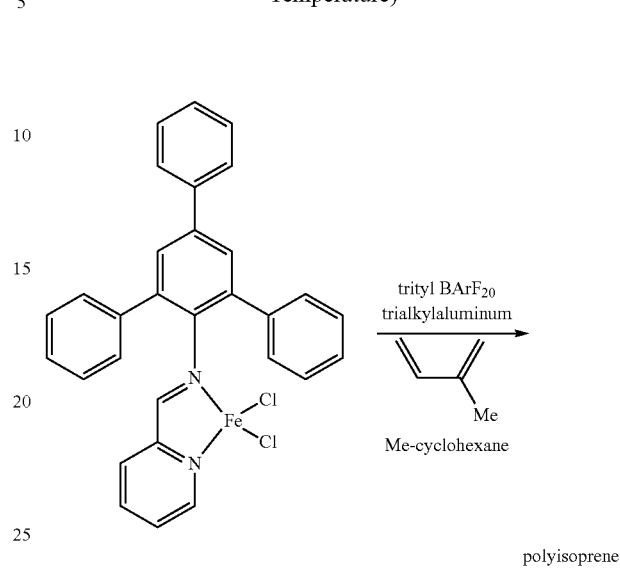

To a 20 mL scintillation vial was added (E)-2,4,6-triphenyl-N-(pyridin-2-ylmethylene)aniline (or supermesityl-iminopyridine) iron(11) chloride complex (5.0 mg, 9.3 µmol, 1.0 equiv) and 2 mL of Me-cyclohexane, followed by triethylaluminum (3.2 mg, 28 µmol, 3.0 equiv) in 1 mL Me-cyclohexane at 23° C. The reaction mixture was stirred for 5 min and trityl tetrakis(pentafluorophenyl)borate (8.6 mg, 9.3 µmol, 1.0 equiv) was added as a dispersion in 2 mL Me-cyclohexane at 23° C. The reaction mixture was stirred for 5 min and isoprene (0.681 g, 1.00 mL, 10.0 mmol, 1.08×10$^3$ equiv) was added. The reaction mixture was stirred for 2 hours at 23° C. The reaction mixture was quenched by opening to air and diluting with DCM from the squirtbottle (10 mL). The title compound was isolated by precipitation in cold methanol to yield a colorless gum (yield >99% 700 mg). NMR Spectroscopy: $^1$H NMR (500 MHz, CDCl$_3$, 23° C., δ): olefinic H atoms for 1,4-motif: 5.12 (s, 1H, $\Delta v_{1/2}$=40 Hz); 3,4-motif: 4.72 (br, 1H), 4.68 (br, 1H); aliphatic H atoms for 1,4-motif: 2.03 (br, 4H), 1.70 (s, 3H), 3,4-motif: 2.22 (br, 1H), 1.80 (m, b, 2H), 1.32 (s, b, 3H). $^{13}$C NMR (125 MHz, CDCl$_3$, 25° C., 5): olefinic C atoms for 1,4-motif: 135.6 (m), 134.0 (m), 126.5 (m), 125.3 (m); 3,4-motif: 147.7, 111.5, aliphatic C atoms for 1,4-motif: 30.8, 28.5 (m), 26.1 (m), 23.7; 3,4-motif: 45.4 (m), 36.8 (m), 33.2 (m), 18.5 (m). SEC chromatography (eluent: THF, Polystyrene standards): $M_w$=100,000 g/mol, D=2.3. Selectivity 1,4/3,4=3:1 and cis-1,4/trans-1,4>99:1 (75% of cis-1,4-polyisoprene in the bulk).

| Example 8 PI microstructure | | | |
|---|---|---|---|
| 1,4-cis-PI (%) | 1,4-trans-PI (%) | 3,4-PI (%) | 1,2-PI (%) |
| 85 | <1 | 15 | None detected |

| Example 9 PI microstructure | | | |
|---|---|---|---|
| 1,4-cis-PI (%) | 1,4-trans-PI (%) | 3,4-PI (%) | 1,2-PI (%) |
| 75 | <1 | 25 | None detected |

Polymerization Example 10 cis-1,4-Polyisoprene (in Toluene at Room Temperature)

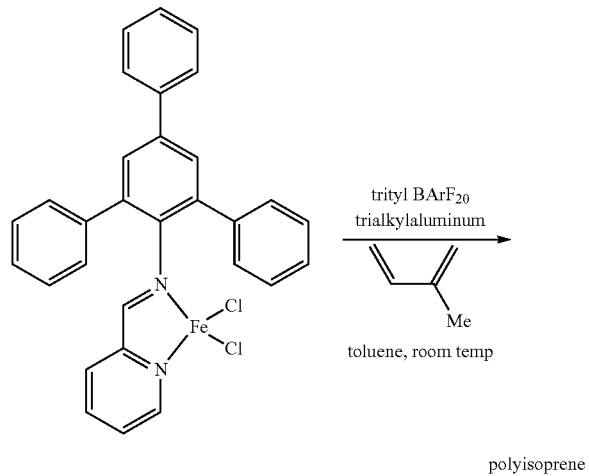

To a 20 mL scintillation vial was added (E)-2,4,6-triphenyl-N-(pyridin-2-ylmethylene)aniline (or supermesityl-iminopyridine) iron(II) chloride complex (5.0 mg, 9.3 μmol, 1.0 equiv) and 2 mL of toluene, followed by triethylaluminum (3.2 mg, 28 μmol, 3.0 equiv) in 1 mL toluene at 23° C. The reaction mixture was stirred for 2 min and trityl tetrakis (pentafluorophenyl)borate (8.6 mg, 9.3 μmol, 1.0 equiv) was added as a solution in 2 mL toluene at 23° C. The reaction mixture was stirred for 2 min and isoprene (0.681 g, 1.00 mL, 10.0 mmol, 1.08×10³ equiv) was added. The reaction mixture was stirred for 1 hour at 23° C. The reaction mixture was quenched by opening to air and diluting with DCM from the squirtbottle (10 mL). The title compound was isolated by precipitation in cold methanol to yield a colorless gum (yield >99% 700 mg). NMR Spectroscopy: $^1$H NMR (500 MHz, $CDCl_3$, 23° C., δ): olefinic H atoms for 1,4-motif: 5.12 (s, 1H, $\Delta v_{1/2}$=40 Hz); 3,4-motif: 4.72 (br, 1H), 4.68 (br, 1H); aliphatic H atoms for 1,4-motif: 2.03 (br, 4H), 1.70 (s, 3H), 3,4-motif: 2.22 (br, 1H), 1.80 (m, b, 2H), 1.32 (s, b, 3H). $^{13}$C NMR (125 MHz, $CDCl_3$, 25° C., 8): olefinic C atoms for 1,4-motif: 135.6 (m), 134.0 (m), 126.5 (m), 125.3 (m); 3,4-motif: 147.7, 111.5, aliphatic C atoms for 1,4-motif: 30.8, 28.5 (m), 26.1 (m), 23.7; 3,4-motif: 45.4 (m), 36.8 (m), 33.2 (m), 18.5 (m). SEC chromatography (eluent: THF, Polystyrene standards): $M_w$=150,000 g/mol, Đ=1.9. Selectivity 1,4/3,4=2:1 and cis-1,4/trans-1,4>99:1 (66% of cis-1,4-polyisoprene in the bulk).

Example 10 PI microstructure

| 1,4-cis-PI (%) | 1,4-trans-PI (%) | 3,4-PI (%) | 1,2-PI (%) |
|---|---|---|---|
| 66 | <1 | 34 | None detected |

Polymerization Example 11 cis-1,4-Polyisoprene (10 g Scale)

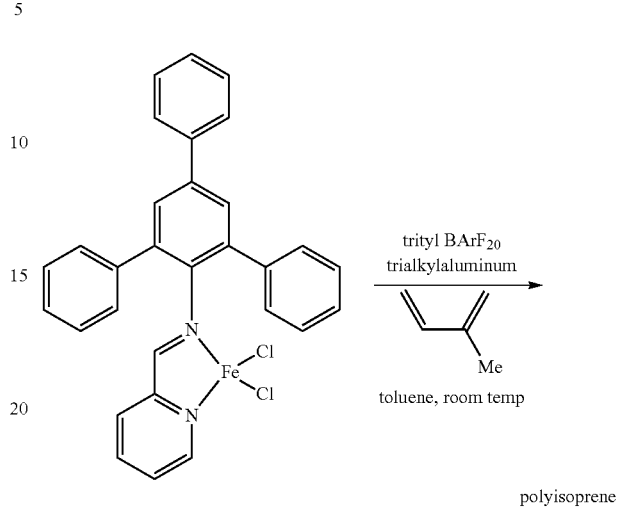

To a 500 mL round-bottom flask was added (E)-2,4,6-triphenyl-N-(pyridin-2-ylmethylene)aniline (or supermesityl-iminopyridine) iron(II) chloride (15.0 mg, 28 μmol, 1.0 equiv) and 10 mL of toluene, followed by triethylaluminum (9.6 mg, 84 μmol, 3.0 equiv) in 5 mL toluene at 23° C. The reaction mixture was stirred for 5 min and trityl tetrakis (pentafluorophenyl)borate (25.8 mg, 28 μmol, 1.0 equiv) was added as a solution in 5 mL toluene at 23° C. The reaction mixture was mixed for 5 min at −78° C. and 50 mL of Me-cyclohexane was added to bring the total volume to 70 mL, and then isoprene (10.0 g, 14.7 mL, 147 mmol, 5.25×10³ equiv) was added at −78° C. The reaction mixture was stirred for 5 hours at −78° C. The reaction mixture was quenched by opening to air and diluting with DCM from the squirtbottle (50 mL). The title compound was isolated by precipitation in cold methanol to yield a colorless gum (yield >99% 10.1 g after drying overnight under vacuum). NMR Spectroscopy: $^1$H NMR (500 MHz, $CDCl_3$, 23° C., 8): olefinic H atoms for 1,4-motif: 5.12 (s, 1H, $\Delta v_{1/2}$=50 Hz); 3,4-motif: 4.72 (br, 1H), 4.68 (br, 1H); aliphatic H atoms for 1,4-motif: 2.03 (br, 4H), 1.70 (s, 3H), 3,4-motif: 2.22 (br, 1H), 1.80 (m, b, 2H), 1.32 (s, b, 3H). $^{13}$C NMR (125 MHz, $CDCl_3$, 25° C., 8): olefinic C atoms for 1,4-motif: 135.6 (m), 134.0 (m), 126.5 (m), 125.3 (m); 3,4-motif: 147.7, 111.5, aliphatic C atoms for 1,4-motif: 30.8, 28.5 (m), 26.1 (m), 23.7; 3,4-motif: 45.4 (m), 36.8 (m), 33.2 (m), 18.5 (m). SEC chromatography (eluent: UV, Polystyrene standards): $M_w$=800,000 g/mol, Đ=3.5. Selectivity 1,4/3,4=5:1 and cis-1,4/trans-1,4>99:1 (83% of cis-1,4-polyisoprene in the bulk).

Example 11 PI microstructure

| 1,4-cis-PI (%) | 1,4-trans-PI (%) | 3,4-PI (%) | 1,2-PI (%) |
|---|---|---|---|
| 83 | <1 | 17 | None detected |

Discussion

Polymerizations Following General Method I or II.

All of the ligands studied demonstrate a preferred regioselectivity for 1,4-cis-PI. These selectivities are comparable to known lanthanide-catalyzed isoprene polymerization reactions (Li et al., *Organometallics* (2010) 29:2186-2193, incorporated by reference). Of note is ligand (L-29), which gave greater than 99% regioselectivity for the desired 1,4-cis-polyisoprene and in excellent yield.

TABLE 3

Summary of the regioselective generation of 1,4-cis-PI*

| Ligand | 1,4-cis-PI to [sum of 1,4-trans-, 3,4- and 1,2-]PI | 1,4-cis-PI to 1,4-trans-PI | Percent yield |
|---|---|---|---|
| L-1 | 71:29 | 98:2 | 30% |
| L-2 | 65:35 | 80:20 | 37% |
| L-3 | 96:4 | 98:2 | 64% |
| L-4 | 90:10 | 97:3 | 35% |
| L-5 | 86:14 | 95:5 | 45% |
| L-6 | 83:17 | 94:6 | 60% |
| L-7 | 70:30 | 85:15 | 5% |
| L-8 | 83:17 | 92:8 | 60% |
| L-9 | 82:18 | 94:6 | 12% |
| L-10 | 60:40 | 75:25 | 58% |
| L-11 | 55:45 | 70:30 | 9% |
| L-12 | 75:25 | 85:15 | 30% |
| L-13 | 82:18 | 94:6 | 10% |
| L-14 | 60:40 | 70:30 | 5% |
| L-15 | 74:26 | 86:14 | 16% |
| L-16 | 80:20 | 92:8 | 40% |
| L-17 | 83:17 | 94:6 | 12% |
| L-18 | 79:21 | 91:9 | 11% |
| L-19 | 97:3 | 98:2 | 66% |
| L-20 | 91:9 | 95:5 | 22% |
| L-21 | 80:20 | 89:11 | 14% |
| L-22 | 76:24 | 88:12 | 16% |
| L-23 | 94:6 | 97:3 | 31% |
| L-24 | 81:19 | 91:9 | 34% |
| L-25 | 77:23 | 89:11 | 31% |
| L-26 | 66:34 | 85:15 | 9% |
| L-27 | 59:41 | 78:22 | 5% |
| L-28 | 68:32 | 88:12 | 8% |
| L-29 | 98:2 | 99.5:0.5 | 93% |
| L-30 | 96:4 | 99:1 | 72% |
| L-31 | 95:5 | 97:3 | 30% |
| L-32 | 71:29 | 77:23 | 5% |
| L-33 | 69:31 | 75:25 | 5% |
| L-34 | 80:20 | 86:14 | 15% |
| L-35 | 79:21 | 85:15 | 18% |
| L-36 | 78:22 | 92:8 | 16% |
| L-37 | 81:19 | 93:7 | 69% |
| L-38 | 86:14 | 94:6 | 38% |
| L-39 | 80:20 | 91:9 | 35% |
| L-40 | 83:17 | 94:6 | 70% |
| L-41 | 60:40 | 80:20 | 5% |
| L-42 | 80:20 | 92:8 | 35% |
| L-43 | 87:13 | 93:7 | 38% |
| L-44 | 79:21 | 93:7 | 40% |
| L-45 | 78:22 | 91:9 | 30% |
| L-46 | 80:20 | 92:8 | 33% |
| L-47 | 82:18 | 94:6 | 49% |
| L-48 | 82:18 | 93:7 | 15% |
| L-49 | 60:40 | 77:23 | 8% |
| L-50 | 78:22 | 88:12 | 95% |
| L-51 | 81:19 | 89:11 | 33% |
| L-52 | 85:15 | 92:8 | 58% |
| L-53 | 85:15 | 91:9 | 33% |
| L-54 | 86:14 | 93:7 | 28% |
| L-56 | 88:12 | 94:6 | 42% |
| L-57 | 65:35 | 84:16 | 37% |
| L-58 | 69:31 | 85:15 | 21% |
| L-59 | 89:11 | 95:5 | 63% |
| L-60 | 46:54 | 63:37 | 52% |
| L-61 | 49:51 | 61:39 | 23% |
| L-62 | 71:29 | 83:17 | 15% |
| L-63 | 75:25 | 90:10 | 43% |

*as determined by $^1$H-NMR (500 MHz, CDCl$_3$, 25° C.) and $^{13}$C-NMR (125 MHz, CDCl$_3$, 25° C.)

Polymerizations Following General Method III.

Iron catalysts with iminopyridine ligands provide the opportunity to control regio- and stereoselectivity in 1,3-dienes functionalization reactions. When treated with triisobutylaluminum or triethylaluminum and trityl BArF$_{20}$ (Ph$_3$C$^+$B(C$_6$F$_5$)$_4^-$), (L-97)- and (L-70)-iron complexes polymerize the 1,3-diene isoprene with control over the double bond geometry of the 1,4-polyisoprene formed. The (L-97)-iron complex affords the trans-1,4-polyisoprene microstructure in over 99:1 selectivity, and the (L-70)-iron complex affords the cis-1,4-polyisoprene microstructure in over 99:1 selectivity.

Polymerization proceeds in apolar solvents such as toluene, heptane, or methylcyclohexane and produces polyisoprene with molar masses of >10$^5$ g/mol and controlled dispersity (D=2). In addition to the 1,4-microstructure, 1,2- and 3,4-insertion of isoprene afford polymer with 1,2- and 3,4-polyisoprene microstructures, respectively. Polymer derived from (L-97)- and (L-70)-iron complexes contain 15% and 8% of the polymer derived from 3,4-insertion, respectively; the 1,2-microstructure was not observed. Iminopyridine-based iron catalysts provide a new opportunity for isoprene polymerization with molecular control of the polymer microstructure. The (L-97)-iron complex provides the best selectivity at 23° C., whereas the (L-70)-iron complex provides the best selectivity at 78° C.

TABLE 4

Summary of the regioselective generation of 1,4-cis-PI*and 1,4-trans-PI

| Ligand | 1,4-PI to 3,4-PI | 1,4-cis-PI to 1,4-trans-PI | Percent yield |
|---|---|---|---|
| L-57 | 40:60 | 67:33 | 99% |
| L-70 | 85:15 | 99:1 | 99% |
| L-71 | 55:45 | 60:40 | 19% |
| L-72 | 60:40 | 97:3 | 99% |
| L-73 | 70:30 | 98:2 | 22% |
| L-74 | 65:35 | 98:2 | 43% |
| L-75 | 60:40 | 97:3 | 99% |
| L-76 | 60:40 | 88:12 | 99% |
| L-77 | 55:45 | 85:15 | 99% |
| L-78 | 50:50 | 50:50 | 18% |
| L-79 | 60:40 | 94:6 | 99% |
| L-80 | 70:30 | 97:3 | 89% |
| L-81 | 83:17 | 92:8 | 69% |
| L-82 | 82:18 | 94:6 | 12% |
| L-83 | 70:30 | 97:3 | 53% |
| L-84 | 60:40 | 70:30 | 39% |
| L-85 | 50:50 | 60:40 | 27% |
| L-87 | 70:30 | 84:16 | 99% |
| L-88 | 83:17 | 25:75 | 99% |
| L-89 | 90:10 | 4:96 | 63% |
| L-90 | 88:12 | 5:95 | 25% |
| L-91 | 91:9 | 4:96 | 61% |
| L-92 | 65:35 | 94:6 | 99% |
| L-93 | 85:15 | 65:35 | 96% |
| L-94 | 50:50 | 50:50 | 99% |
| L-95 | 55:45 | 70:30 | 99% |
| L-96 | 60:40 | 65:35 | 99% |
| L-97 | 93:7 | 1:99 | 99% |
| L-98 | 89:11 | 9:91 | 99% |
| L-99 | 83:17 | 29:71 | 95% |
| L-100 | 75:25 | 40:60 | 99% |
| L-101 | 75:25 | 34:55 | 99% |
| L-102 | 88:12 | 17:83 | 99% |
| L-103 | 50:50 | 80:20 | 99% |
| L-104 | 71:29 | 72:27 | 99% |
| L-105 | 80:20 | 25:75 | 99% |
| L-106 | 50:50 | 60:40 | 90% |
| L-107 | 90:10 | 9:91 | 62% |
| L-108 | 50:50 | 50:50 | 99% |
| L-109 | 89:11 | 2:98 | 87% |
| L-110 | 86:14 | 18:82 | 99% |

*as determined by $^1$H-NMR (500 MHz, CDCl$_3$, 25° C.) and $^{13}$C-NMR (125 MHz, CDCl$_3$, 25° C.)

Polymerization of Other Dienes

The inventors envision that other dienes structurally and electronically similar to isoprene, such as 1,3-pentadiene, cyclohexa-1,3-diene, penta-1,3-diene, buta-1,3-diene, cyclohexa-1,3-diene, trans-β-farnesene, and β-myrcene, will efficiently polymerize following the above described methods. See, e.g., Ricci et al., *Coord. Chem. Rev.* (2010) 254: 661-676.

EQUIVALENTS AND SCOPE

Those skilled in the art will recognize or be able to ascertain using no more than routine experimentation many equivalents to the specific embodiments described herein. The scope of the present embodiments described herein is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim.

Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps.

Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Each of the foregoing patents, patent applications, and references is hereby incorporated by reference, particularly for the teaching referenced herein.

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A method of preparing a polymer, the method comprising polymerizing one or more alkenes in the presence of an iron complex, wherein the iron complex comprises a ligand of the Formula (BI-a):

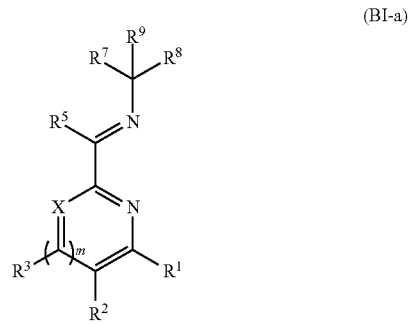

wherein:

m is 0 or 1, provided that when m is 0, X is selected from N—$R^4$; and when m is 1, X is selected from N or C—$R^4$;

each instance of $R^1$, $R^2$, $R^3$, $R^4$, and $R^5$ is independently selected from the group consisting of hydrogen, halogen, —CN, —$NO_2$, —$N_3$, —$SO_2H$, —$SO_3H$, —OH, —SH, —$NH_2$, substituted hydroxyl, substituted thiol, monosubstituted amino, disubstituted amino, trisubstituted amino, sulfonyl, sulfinyl, carbonyl, silyl, phosphino, boronyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^1$ and $R^2$, or $R^2$ and $R^3$, or $R^2$ and $R^4$, or $R^3$ and $R^4$, are optionally joined to form a ring selected from the group consisting of optionally substituted carbocyclyl, optionally substituted heterocyclyl, optionally substituted aryl, and optionally substituted heteroaryl ring;

$R^7$ is optionally substituted aryl or optionally substituted —$CH_2$aryl;

$R^8$ and $R^9$ are each independently selected from the group consisting of hydrogen, halogen, —CN, —$NO_2$, —$N_3$, —$SO_2H$, —$SO_3H$, —OH, —SH, —$NH_2$, substituted hydroxyl, substituted thiol, monosubstituted amino, disubstituted amino, trisubstituted amino, sulfonyl, sulfinyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl, and the one or more alkenes are independently an optionally substituted 1,3-diene of formula (i):

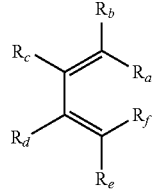

(i)

wherein:
each instance of $R_a$, $R_b$, $R_c$, $R_d$, $R_e$, and $R_f$ is independently selected from the group consisting of hydrogen, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;
or $R_a$ and $R_f$ are joined to form an optionally substituted heterocyclyl or optionally substituted carbocyclyl ring.

2. The method according to claim 1, wherein the ligand is of the Formula (BI-b):

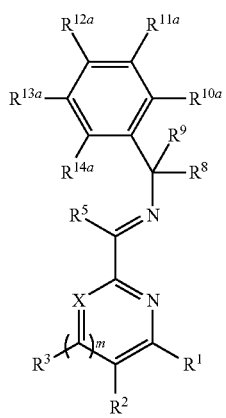

(BI-b)

wherein:
each instance of $R^{10a}$, $R^{11a}$, $R^{12a}$, $R^{13a}$, and $R^{14a}$ is independently selected from the group consisting of hydrogen, halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl.

3. A method of preparing polyisoprene, the method comprising polymerizing isoprene in the presence of an iron complex, wherein the iron complex comprises a ligand of Formula (BI-a):

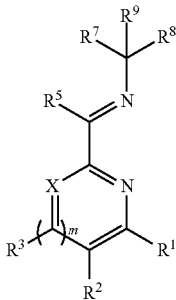

(BI-a)

wherein:
m is 0 or 1, provided that when m is 0, X is selected from N—R$^4$; and when m is 1, X is selected from N or C—R$^4$;
each instance of R$^1$, R$^2$, R$^3$, R$^4$, and R$^5$ is independently selected from the group consisting of hydrogen, halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, phosphino, boronyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or R$^1$ and R$^2$, R$^2$ and R$^3$, R$^2$ and R$^4$, or R$^3$ and R$^4$ are optionally joined to form a ring selected from the group consisting of optionally substituted carbocyclyl, optionally substituted heterocyclyl, optionally substituted aryl, and optionally substituted heteroaryl ring;
R$^7$ is optionally substituted aryl or optionally substituted —CH$_2$aryl; and
R$^8$ and R$^9$ are each independently selected from the group consisting of hydrogen, halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl.

4. The method according to claim 3, wherein the ligand is of the Formula (BI-b):

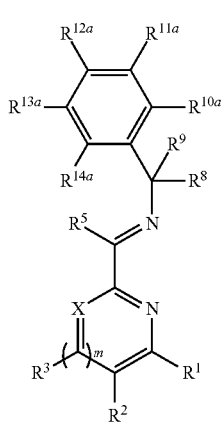

(BI-b)

wherein:

each instance of $R^{10a}$, $R^{11a}$, $R^{12a}$, $R^{13a}$, and $R^{14a}$ is independently selected from the group consisting of hydrogen, halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl.

5. The method according to claim 4, wherein the ligand is of the Formula (BI-c):

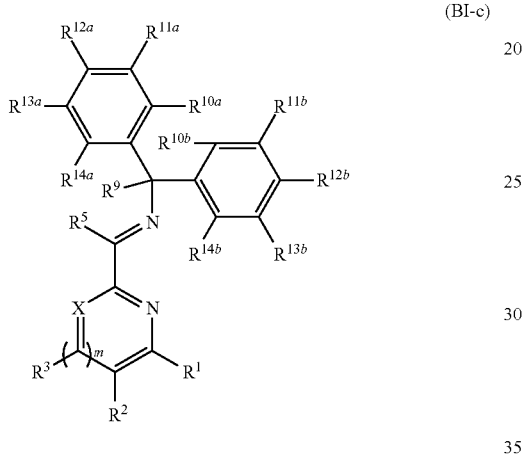

(BI-c)

wherein:

each instance of $R^{10b}$, $R^{11b}$, $R^{12b}$, $R^{13b}$, and $R^{14b}$ is independently selected from the group consisting of hydrogen, halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; and $R^9$ is hydrogen or optionally substituted alkyl.

6. The method according to claim 3, wherein the ligand is selected from the group consisting of:

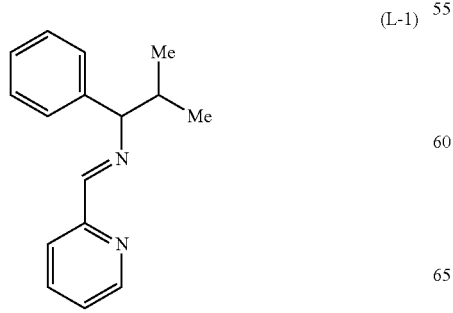

(L-1)

-continued

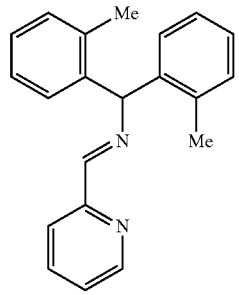

(L-3)

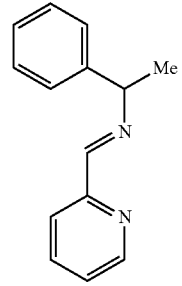

(L-5)

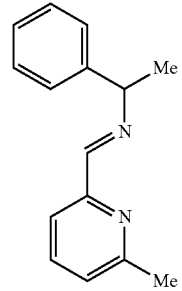

(L-6)

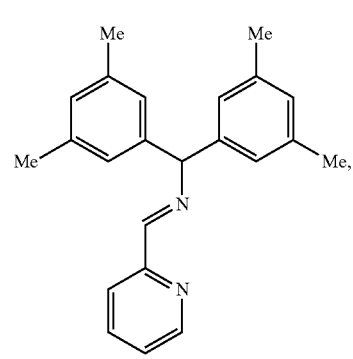

(L-7)

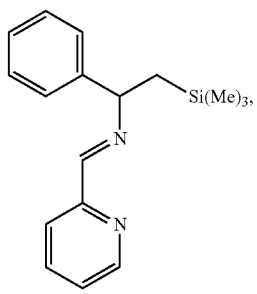

(L-8)

-continued
(L-9)
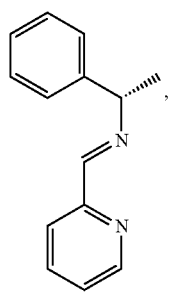
(L-13)
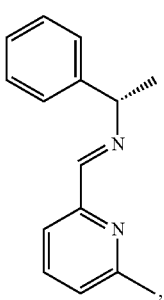
(L-14)
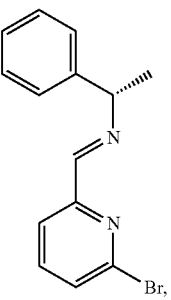
(L-15)
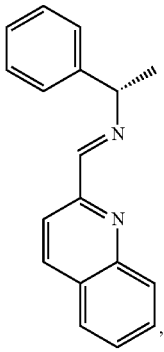
(L-16)
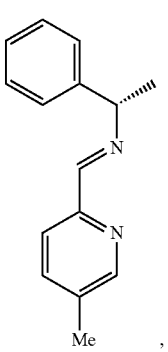
(L-17)
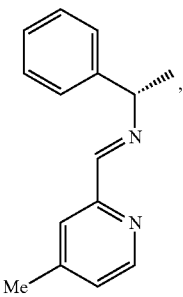
(L-18)
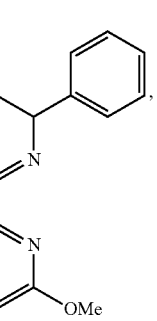
(L-19)
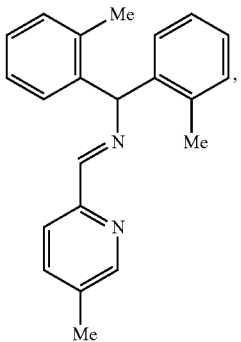
(L-20)
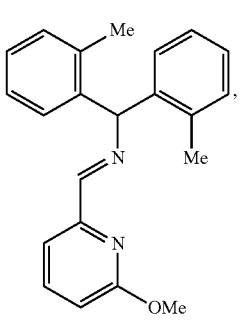
(L-22)
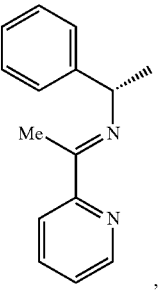

-continued
(L-23)
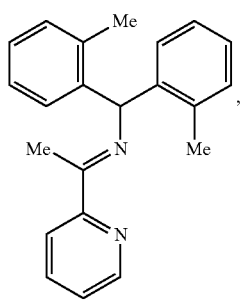
(L-24)
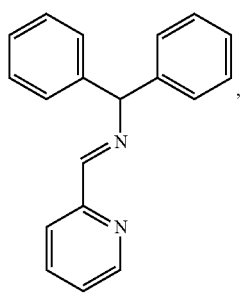
(L-25)
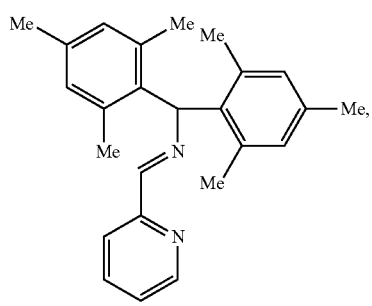
(L-26)
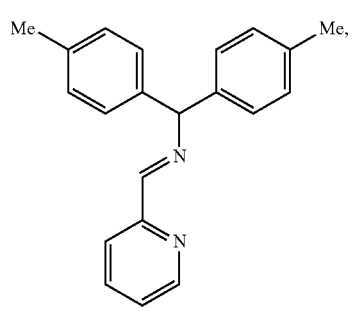
(L-27)
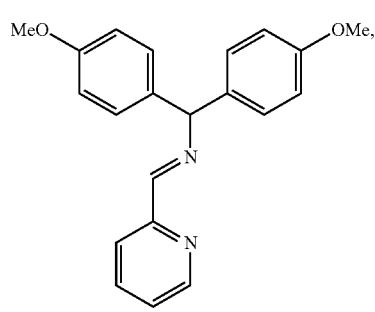
-continued
(L-28)
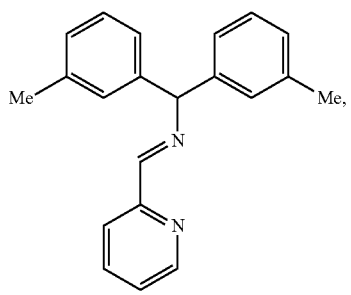
(L-29)
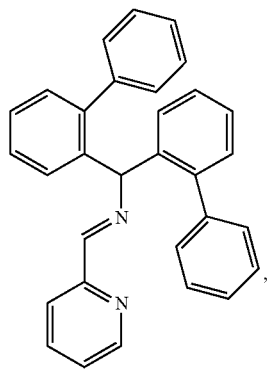
(L-30)
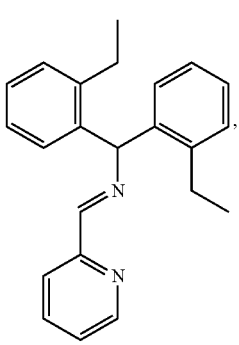
(L-31)
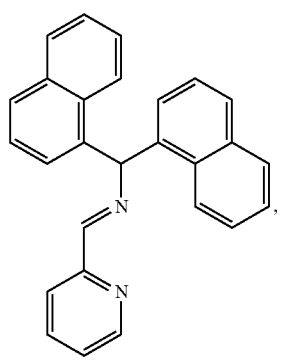

-continued
(L-32)
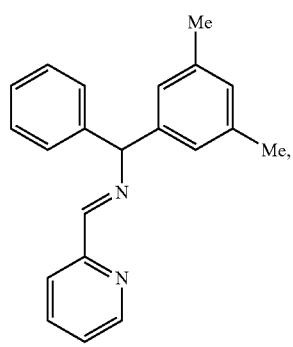
(L-33)
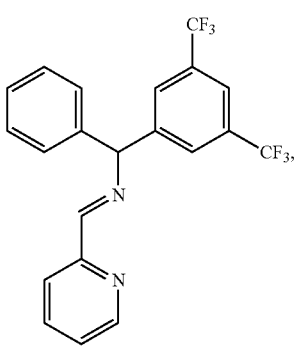
(L-34)
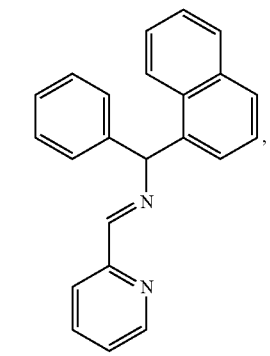
(L-35)
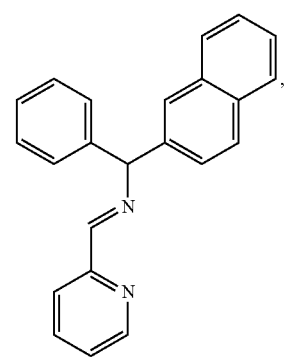
-continued
(L-36)
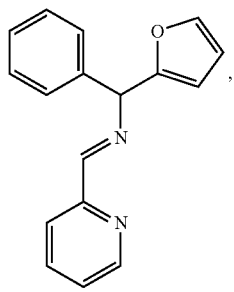
(L-37)
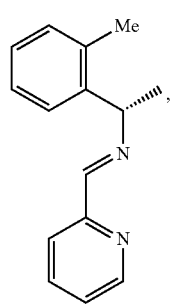
(L-38)
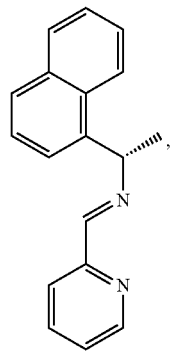
(L-39)
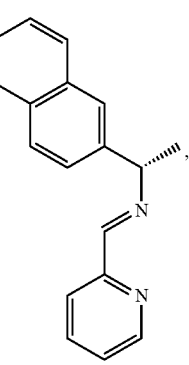
(L-40)
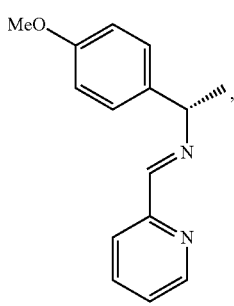

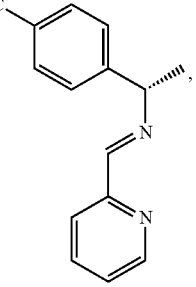 (L-41)
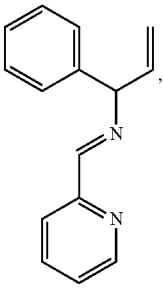 (L-42)
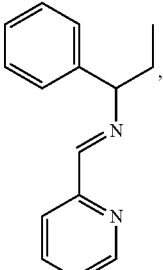 (L-43)
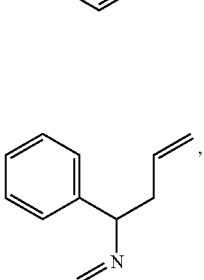 (L-44)
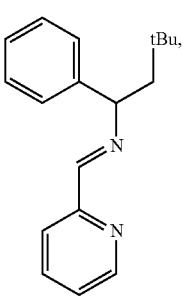 (L-45)
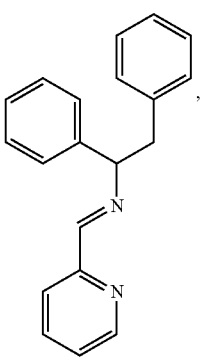 (L-46)
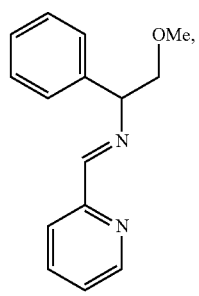 (L-47)
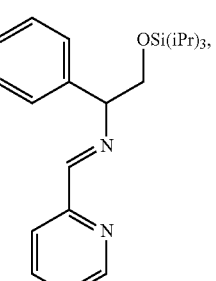 (L-48)
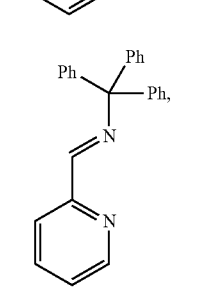 (L-54)
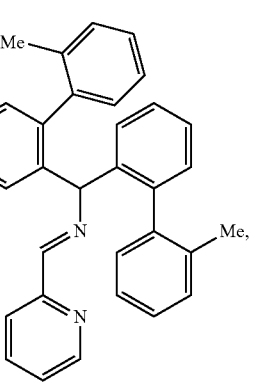 (L-55)

-continued
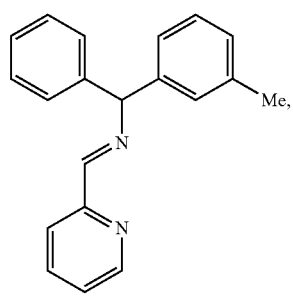 (L-59)
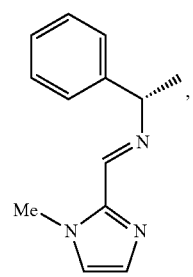 (L-62)
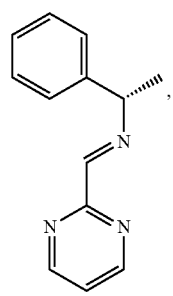 (L-63)
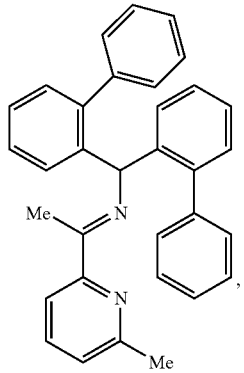 (L-64)
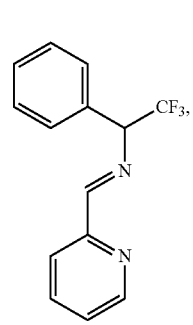 (L-65)
-continued
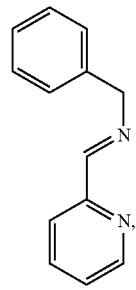 (L-66)
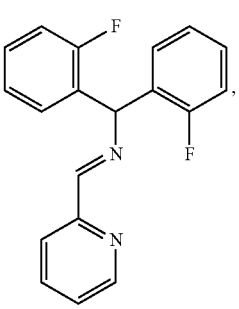 (L-69)
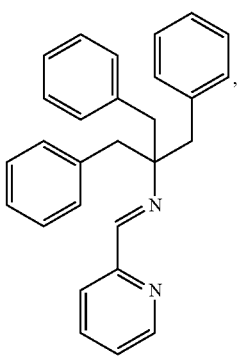 (L-90)
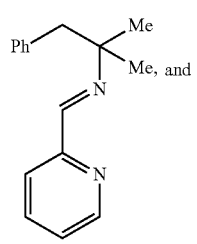 (L-102)
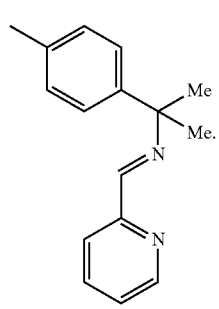 (L-105)

7. The method according to claim 6, wherein the ligand is:

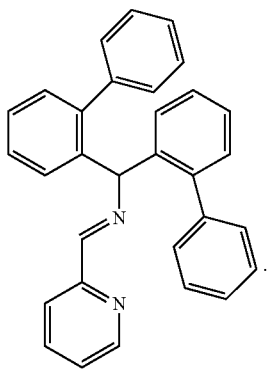

(L-29)

8. The method of claim 7, wherein the polyisoprene is between about 50% to about 100% 1,4-cis-polyisoprene.

9. The method according to claim 3, wherein the iron complex is of the Formula (BII-a):

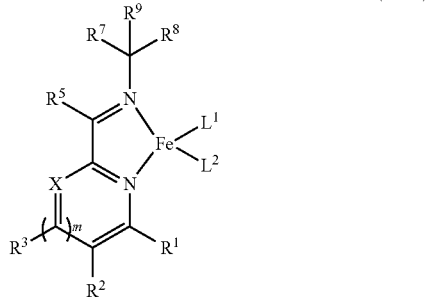

(BII-a)

wherein:
  $L^1$ and $L^2$ are monodentate ligands independently selected from the group consisting of hydrogen, $H_2O$, —$NH_3$, —SCN, —$N_3$, —$N_2$, —$ONO_3$, —$NO_2$, —ONO, —$NCCH_3$, —NC, —CN, —CO, halogen, amino, monosubstituted amino, disubstituted amino, trisubstituted amino, hydroxyl, substituted hydroxyl, thiol, substituted thiol, phosphino, phosphono, phosphoramido, silyl, boronyl, stannyl, germyl, arsenyl, carbonyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or
  $L^1$ and $L^2$ are a bidentate ligand independently selected from the group consisting of —$NH_2$, monosubstituted amino, disubstituted amino, phosphino, silyl, boronyl, —OH, —O—, —CN, optionally substituted alkyl, optionally substituted alkenyl, optionally substituted alkynyl, optionally substituted carbocyclyl, optionally substituted heterocyclyl, optionally substituted aryl, and optionally substituted heteroaryl, wherein $L^1$ and $L^2$ are joined by one or more bonds or by divalent groups selected from the group consisting of divalent alkyl, divalent alkenyl, divalent alkynyl, divalent carbocyclyl, divalent heterocyclyl, divalent aryl, and divalent heteroaryl.

10. The method according to claim 9, wherein $L^1$ and $L^2$ are both chloro.

11. The method according to claim 9, wherein the iron complex is of the Formula (BII-b):

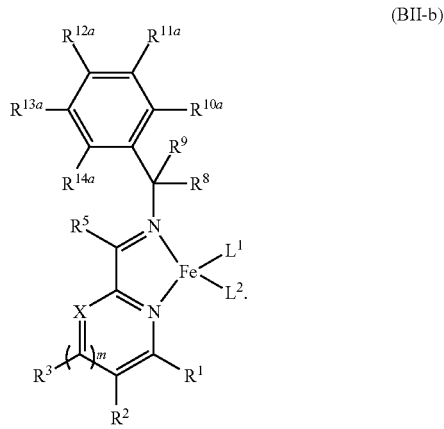

(BII-b)

wherein each instance of $R^{10a}$, $R^{11a}$, $R^{12a}$, $R^{13a}$, and $R^{14a}$ is independently selected from the group consisting of hydrogen, halogen, —CN, —$NO_2$, —$N_3$, —$SO_2H$, —$SO_3H$, —OH, —SH, —$NH_2$, substituted hydroxyl, substituted thiol, monosubstituted amino, disubstituted amino, trisubstituted amino, sulfonyl, sulfonyl, carbonyl, silyl, optionally substituted alkyl, optionally substituted alkenyl, optionally substituted alkynyl, optionally substituted carbocyclyl, optionally substituted heterocyclyl, optionally substituted aryl, and optionally substituted heteroaryl.

12. The method according to claim 3, wherein the polyisoprene is between about 50% to about 100% 1,4-cis-polyisoprene.

13. The method according to claim 3, wherein the polyisoprene is less than 5% 1,4-trans-polyisoprene.

14. The method according to claim 3, wherein the polyisoprene comprises 1,4-cis-polyisoprene and 1,4-trans-polyisoprene in a ratio of between about 95:5 to about 100:0 1,4-cis-polyisoprene to 1,4-trans-polyisoprene.

15. The method according to claim 3, wherein the polyisoprene is between about 50% to about 100% 1,4-trans-polyisoprene.

16. The method according to claim 3, wherein the polyisoprene is less than 5% 1,4-cis-polyisoprene.

17. The method according to claim 3, wherein the polyisoprene comprises 1,4-trans-polyisoprene and 1,4-cis-polyisoprene in a ratio of between about 95:5 to about 100:0 1,4-trans-polyisoprene to 1,4-cis-polyisoprene.

18. The method according to claim 3, wherein the polyisoprene is less than 30% 3,4-polyisoprene.

19. The method according to claim 3, wherein the polyisoprene is less than 5% 1,2-polyisoprene.

20. The method according to claim 3, wherein the method comprises polymerizing isoprene in the presence of an initiator.

21. The method according to claim 3, wherein the method comprises polymerizing isoprene in the presence of an alkylating agent and a dealkylating agent.

22. The method according to claim 3, wherein the number-average molar mass (Mn) of the polyisoprene is between about 2,000 g/mol to about 5,000,000 g/mol.

23. The method according to claim 3, wherein the dispersity of the polyisoprene is between about 1 to about 20.

24. A method of preparing polyisoprene, the method comprising polymerizing isoprene in the presence of an iron complex, wherein the iron complex comprises a ligand of the Formula (D-I):

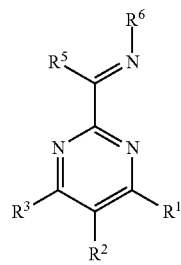

(D-I)

wherein:
each instance of $R^1$, $R^2$, $R^3$, and $R^5$ is independently selected from the group consisting of hydrogen, halogen, —CN, —NO$_2$, —N$_3$, —SO$_2$H, —SO$_3$H, —OH, —SH, —NH$_2$, substituted hydroxyl, substituted thiol, monosubstituted amino, disubstituted amino, trisubstituted amino, sulfonyl, sulfinyl, carbonyl, silyl, phosphino, boronyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^1$ and $R^2$, or $R^2$ and $R^3$ are optionally joined to form a ring selected from the group consisting of optionally substituted carbocyclyl, optionally substituted heterocyclyl, optionally substituted aryl, and optionally substituted heteroaryl ring; and $R^6$ is optionally substituted alkyl, optionally substituted carbocyclyl, or optionally substituted heterocyclyl.

25. A method of preparing polyisoprene, the method comprising polymerizing isoprene in the presence of an iron complex, wherein the iron complex comprises a ligand of the Formula (C-I):

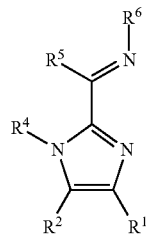

(C-I)

wherein:
each instance of $R^1$, $R^2$, $R^4$, and $R^5$ is independently selected from the group consisting of hydrogen, halogen, —CN, —NO$_2$, —N$_3$, —SO$_2$H, —SO$_3$H, —OH, —SH, —NH$_7$, substituted hydroxyl, substituted thiol, monosubstituted amino, disubstituted amino, trisubstituted amino, sulfonyl, sulfinyl, carbonyl, silyl, phosphino, boronyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^1$ and $R^2$, or $R^2$ and $R^4$ are optionally joined to form a ring selected from the group consisting of optionally substituted carbocyclyl, optionally substituted heterocyclyl, optionally substituted aryl, and optionally substituted heteroaryl ring; and $R^6$ is optionally substituted alkyl, optionally substituted carbocyclyl, or optionally substituted heterocyclyl.

26. A method of preparing polyisoprene, the method comprising polymerizing isoprene in the presence of an iron complex, wherein the iron complex comprises a ligand of formula:

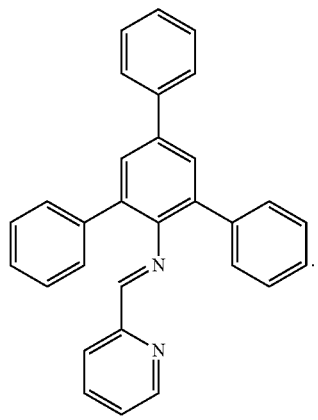

(L-70)

27. The method of claim 26, wherein the polyisoprene is between about 50% to about 100% 1,4-cis-polyisoprene.

28. A method of preparing polyisoprene, the method comprising polymerizing isoprene in the presence of an iron complex, wherein the iron complex comprises a ligand of formula:

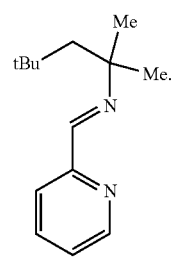

(L-97)

29. The method of claim 28, wherein the polyisoprene is between about 50% to about 100% 1,4-trans-polyisoprene.

30. An iron complex comprising a ligand of formula:

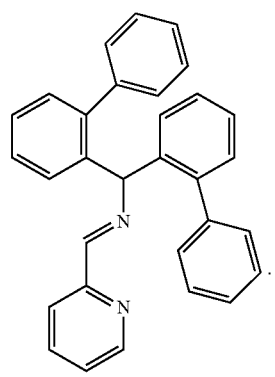

(L-29)

31. An iron complex comprising a ligand of formula:
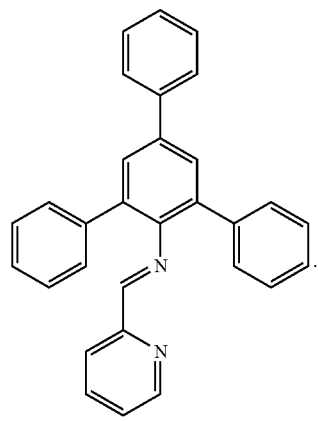
(L-70)
32. An iron complex comprising a ligand of formula:
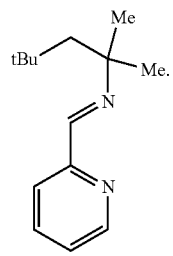
(L-97)
* * * * *